(12) United States Patent
Miyagawa et al.

(10) Patent No.: US 6,423,869 B1
(45) Date of Patent: Jul. 23, 2002

(54) POLYOL-AMINO ACID COMPOUNDS HAVING ANTI-HELICOBACTER PYLORI ACTIVITY

(75) Inventors: Ken-ichiro Miyagawa; Shigetoshi Tsubotani, both of Osaka; Masafumi Nakao, Ikoma; Yoshitaka Nakano, Settsu; Keiji Kamiyama, Ibaraki; Motoo Izawa, Amagasaki; Yohko Akiyama, Ohmihachiman; Yuji Nishikimi, Nishinomiya, all of (JP)

(73) Assignee: Takeda Chemical Industries, Inc., Osaka (JP)

( * ) Notice: Subject to any disclaimer, the term of this patent is extended or adjusted under 35 U.S.C. 154(b) by 0 days.

(21) Appl. No.: 09/423,118

(22) PCT Filed: Jul. 8, 1998

(86) PCT No.: PCT/JP98/03066

§ 371 (c)(1),
(2), (4) Date: Nov. 1, 1999

(87) PCT Pub. No.: WO99/02549

PCT Pub. Date: Jan. 21, 1999

(30) Foreign Application Priority Data

Jul. 9, 1997 (JP) ............................................. 9-184086

(51) Int. Cl.⁷ ........................................... C07C 229/00
(52) U.S. Cl. ....................... 562/553; 562/567; 562/587; 514/18; 514/19; 530/331; 435/252.1; 435/252.5
(58) Field of Search ............................ 530/331; 514/18, 514/19; 562/567, 553; 435/252.1, 252.5

(56) References Cited

FOREIGN PATENT DOCUMENTS

CA          2146414 A      10/1995

OTHER PUBLICATIONS

Phillips Helicobacter 6, 151, 2001.*
Pilotto Digestive and Liver Disease 32 (8) 667–72, 2000.*
Leung Expert Opin Pharmacother 1 (3) 507–14, 2000.*
T. Haskell et al., "The Preparation and Biological Activity of . . . " *Carbohydrate Research*, 28 (1973) pp. 263–280.

K. Leontein et al., "Formation of 1,5–Dideoxy–1,5–iminohexitols on . . . " *Acta Chemica Scandinavica* B 36 (1982) pp. 515–518.
J. Yoshimura et al., "Aminosugars XXVI. Synthesis of Amido–Bonded . . . " *Bulletin of the Chemical Society of Japan*, vo. 49, No. 9, Sep. 1976, pp. 2511–2514.
Wotherspoon et al. "Regression of primary low–grade B–cell gastric lymphoma of mucosa–associated lymphoid tissue type after eradication of Helicobacter pylori " The Lancet 342:575–577 (1993).
Uemura et al. "Effect of Helicobacter pylori Eradication on subsequent development of cancer after endoscopic resection of early gastric cancer" Cancer Epidemiology 6:639–642 (1997).
Shimizu et al. "Eradication diminishes enhancing effects of Helicobacter pylori infection on glandular stomach carcinogenesis in Mongolian gerbils" Cancer Res. 60:1512–1514 (2000).

* cited by examiner

Primary Examiner—Christopher S. F. Low
Assistant Examiner—David Lukton
(74) Attorney, Agent, or Firm—Mark Chao; Elaine M. Ramesh

(57) ABSTRACT

A compound of the formula (I):

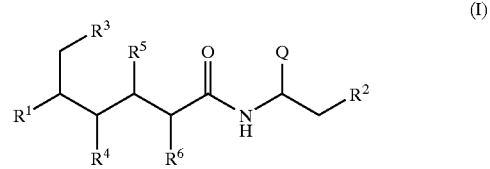

(I)

wherein $R^1$ represents an amino group which may be substituted; $R^2$ represents a carboxy group which may be esterified or amidated; $R^3$, $R^4$, $R^5$ and $R^6$ each represent a hydroxy group which may be protected; Q represents an aryl group which may be substituted; or a salt thereof is disclosed. The compound (I) possesses ant-*Helicobacter pylori* activity, and is useful in the prevention or treatment of various diseases associated with Helicobacter bacteria, such as duodenal ulcer, gastric ulcer, chronic gastritis and cancer of the stomach.

38 Claims, 3 Drawing Sheets

POLYOL-AMINO ACID COMPOUNDS HAVING ANTI-HELICOBACTER PYLORI ACTIVITY

TECHNICAL FIELD

The present invention relates to a polyol, a method of producing it, and use thereof. More particularly, the invention relates to a bioactive compound of use as a medicine, for example as a prophylactic and therapeutic drug for diseases such as gastric ulcer and duodenal ulcer, and an anti-*Helicobacter pylori* (hereinafter may be referred to as *H. pylori* or HP) agent comprising said compound.

BACKGROUND ART

Being a member of the group of bacteria doing harm in the gastrointestinal tract, *Helicobacter pylori* is a gram-negative microaerophile belonging to the genus Helicobacter and, as suggested, may be a major factor in the recurrences of gastritis, duodenal ulcer and stomach ulcer.

For the treatment of various diseases associated with *Helicobacter pylori* infection, chemotherapy such as a two-drug combined therapy using a bismuth drug and an antibiotic or a three-drug combined therapy using a bismuth drug, metronidazole (U.S. Pat. No. 2,944,061), and either tetracycline (e.g. U.S. Pat. No. 2,712,517) or amoxicillin (U.S. Pat. No. 3,192,198) is being practiced today. The ternary therapy consisting of a gastric proton pump inhibitor, amoxicillin, and clarithromycin has also been found to be effective (Gut, 1995, 37 (Supplement 1): A365) (Gastroenterology, 1996, 110: A171). Such drugs as bismuth drugs, antibiotics, and metronidazole are all administered by the oral route.

Referring to polyols, PCT International Patent Application Publication No. WO93/06838 and Acta Chemical Scandinavica B 36, 515–518 (1982) disclose

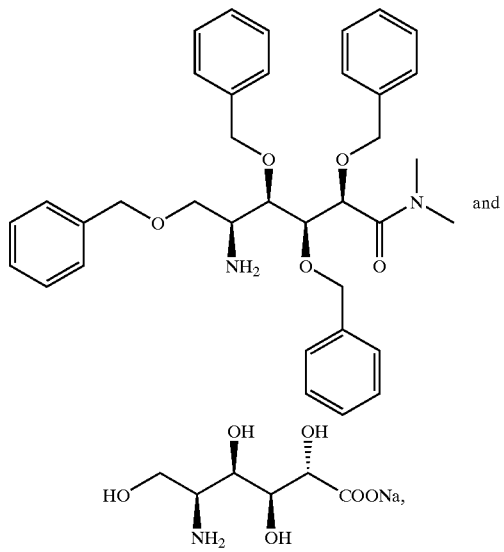

respectively, as synthetic intermediates, and Carbohyd. Res., 28 (2), 263–280 (1973) states that

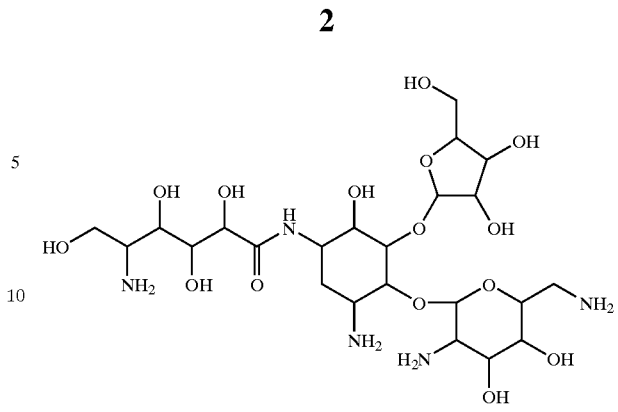

is active against gram-negative bacteria.

For an improved expression of the efficacy of an active ingredient and a reduced risk for side effects, an attempt was made to formulate amoxicillin, for instance, into a gastric mucosa-adhesive composition to prolong its intragastric residence time and let amoxicillin be released at a controlled rate and with consequent improved availability of active ingredients (WO 94/00112). It has been demonstrated that the rate of clearance of *Helicobacter pylori* can be improved by causing an anti-*Helicobacter pylori* substance to stay in the stomach longer to ensure prolonged exposure of the bacteria to the active substance [Scand. J. Gastroenterol., 29, 16–42 (1994)].

However, in order that a sufficient growth-inhibitory concentration may be maintained in the habitat of *Helicobacter pylori*, said bismuth drugs, antibiotics, or metronidazole must be administered daily in massive doses and such therapeutics entail various troubles, for example, the onset of adverse reactions such as vomiting and diarrhea. Under the circumstances, the present invention has for its object to provide a novel medicinal agent having high antibacterial activity, particularly against *Helicobacter pylori* and other bacteria of the genus Helicobacter, and producing clinically rewarding prophylactic and therapeutic responses with a reduced incidence of adverse reactions.

DISCLOSURE OF INVENTION

Under the circumstances, the present invention has for its object to provide a novel medicinal agent having high antibacterial activity, particularly against *Helicobacter pylori* and other bacteria of the genus Helicobacter, and producing clinically rewarding prophylactic and therapeutic responses with a reduced incidence of adverse reactions.

The present invention has for its object to provide a pharmaceutical composition which has enhanced mucosa-adherent activity compared with other gastric mucosa-adherent preparations, and consequently, an extremely improved efficacy of the active ingredient, in particular, an anti-*Helicobacter pylori* composition and a pharmaceutical preparation, for the prophylaxis, treatment or prevention of relapse of gastroduodenal ulcers, which is very satisfactory and favorable in having anti-*Helicobacter pylori* effect, low risk for side effects, sustained effect, and safety.

As the result of their intensive research, the inventors of the present invention synthesized a novel polyhydric alcohol (polyol) of the following general formula

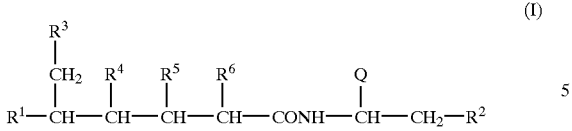

(I)

[wherein $R^1$ represents amino which may be substituted; $R^2$ represents carboxy which may be esterified or amidated; $R^3$, $R^4$, $R^5$, and $R^6$ each represent hydroxy which may be protected; Q represents aryl which may be substituted], which is structurally distinct in that the following defined group:

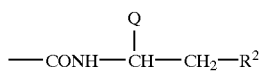

[Q and $R^2$ are the same meaning as defined above] is directly bound to a carbon atom, and discovered that, because of this unique chemical structure, the above compound displays remarkable inhibitory activity against the bacteria doing harm in the gastrointestinal tract, particularly high anti-Helicobacter activity, with clinically favorable pharmacological characteristics such as a low risk for adverse effects. The present invention has been developed on the basis of the above finding.

In view of the above state of the art, the inventors of the present invention have discovered that the effectiveness of active ingredients (e.g. anti Helicobacter pylori effect) can be potentiated by incorporating an agent (e.g. a curdlan and/or a low-substituted hydroxypropylcellulose) which swells a viscogenic agent, in the objective gastric mucosa adhesive composition containing an active ingredient (e.g. anti Helicobacter pylori substance), and that the composition has favorable safety characteristics and an enhanced adhesion to the mucosa.

The present invention, therefore, relates to:

(1) a compound of the formula (I):

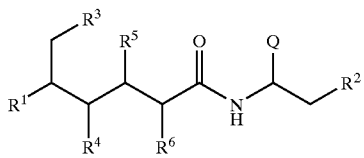

wherein $R^1$ represents amino which may be substituted; $R^2$ represents carboxy which may be esterified or amidated; $R^3$, $R^4$, $R^5$, and $R^6$ each represent hydroxy which may be protected; Q represents aryl which may be substituted; or a salt thereof, (2) the compound according to (1), wherein $R^1$ is an acylamino group or an amino group substituted by a hydrocarbon group which may be substituted, (3) the compound according to (2), wherein the acylamino group is an amino group substituted by an amino acid residue, (4) the compound according to (3), wherein the amino acid residue is an α-amino acid residue, (5) the compound according to (1), wherein $R^1$ is an amino group or a group represented by the formula:

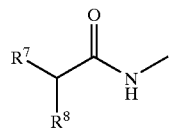

wherein $R^7$ is an amino which may be substituted with a α-L-amino acid residue which may be substituted with a α-L-amino acid residue, $R^8$ is a hydrocarbon group which may be substituted; $R^2$ represents a carboxy group; $R^3$, $R^4$, $R^5$, and $R^6$ each represents a hydroxy group; Q represents a phenyl group, (6) the compound according to (5), which is represented by the formula (V):

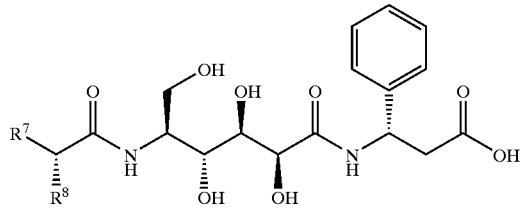

wherein $R^7$ and $R^8$ are of the same meaning as defined in (5), (7) the compound according to (5), wherein $R^8$ is a $C_{1-10}$ alkyl group, a $C_{6-14}$ aryl-$C_{1-6}$ alkyl group, a $C_{2-10}$ alkenyl group or a $C_{2-10}$ alkynyl group, each of which may be substituted, (8) the compound according to (7), wherein $R^8$ is a $C_{1-6}$ alkyl group or a $C_{2-6}$ alkenyl group, (9) the compound according to (7), wherein $R^7$ is an amino group which may be substituted with a valyl group, a valylvalyl group, a valylisoleucyl group or a valylleucyl group,

(10) the compound according to (8), wherein $R^8$ is an isobutyl group or an allyl group,

(11) the compound according to (1), wherein $R^1$ is an amino group,

(12) a compound according to (1), which is (S)-3-[(2S, 3R,4R,5S)-2,3,4,6-tetrahydroxy-5-(L-valyl-L-valyl-L-leucyl)aminohexanoyl]amino-3-phenylpropionic acid,

(13) a compound according to (1), which is (S)-3-[(2S, 3R,4R,5S)-2,3,4,6-tetrahydroxy-5-(L-valyl-L-isoleucyl-L-leucyl)aminohexanoyl]amino-3-phenylpropionic acid,

(14) a compound according to (1), which is (S)-3-[(2S, 3R,4R,5S)-2,3,4,6-tetrahydroxy-5-(L-valyl-L-leucyl-L-leucyl)aminohexanoyl]amino-3-phenylpropionic acid,

(15) a compound according to (1), which is (S)-3-[(2S, 3R,4R,5S)-2,3,4,6-tetrahydroxy-5-(L-valyl-L-leucyl)aminohexanoyl]amino-3-phenylpropionic acid,

(16) a compound according to (1), which is (S)-3-[(2S, 3R,4R,5S)-2,3,4,6-tetrahydroxy-5-(L-leucyl)aminohexanoyl]amino-3-phenylpropionic acid,

(17) a compound according to (1), which is (S)-3-[(2S, 3R,4R,5S)-5-((S)-2-amino-4-pentenoyl)amino-2,3,4,6-tetrahydroxyhexanoyl]amino-3-phenylpropionic acid,

(18) a compound according to (1), which is (S)-3-[(2S, 3R,4R,5S)-5-((S)-2-aminobutyryl)amino-2,3,4,6-tetrahydroxyhexanoyl]amino-3-phenylpropionic acid,

(19) a compound according to (1), which is (S)-3-[(2S,3R,4R,5S)-2,3,4,6-tetrahydroxy-5-(L-isoleucyl-L-leucyl)aminohexanoyl]amino-3-phenylpropionic acid,

(20) a compound according to (1), which is (S)-3-[(2S,3R,4R,5S)-2,3,4,6-tetrahydroxy-5-(L-methionyl-L-leucyl)aminohexanoyl]amino-3-phenylpropionic acid,

(21) a compound according to (1), which is (S)-3-[(2S,3R,4R,5S)-2,3,4,6-tetrahydroxy-5-((S)-2-(L-norvalyl)amino-4-pentenoyl)aminohexanoyl]amino-3-phenylpropionic acid,

(22) a pharmaceutical composition comprising the compound according to (1),

(23) the composition according to (22), which is an anti-*Helicobacter pylori* agent,

(24) the *Helicobacter pylori* agent according to (23), which is a prophylactic and therapeutic drug for a disease associated with *Helicobacter pylori* infection,

(25) the *Helicobacter pylori* agent according to (24), wherein the disease associated with *Helicobacter pylori* infection is gastric or duodenal ulcer, gastritis, gastric cancer or gastric MALT lymphoma,

(26) a *Helicobacter pylori* agent comprising a combination of the compound according to (1) and at least one other antibacterial or/and antiulcerative agent,

(27) the composition according to (22), which is a gastric mucosa adhesive pharmaceutical composition,

(28) the composition according to (27), which comprises (a) the compound according to (1), (b) a lipid and/or a polyglycerol fatty acid ester and (c) a viscogenic agent capable of being viscous with water,

(29) the composition according to (28), wherein (c) the viscogenic agent is an acrylic polymer or a salt thereof,

(30) the composition according to (28), which comprises (d) a material which swells the viscogenic agent,

(31) the composition according to (30), wherein the material which swells the viscogenic agent is a curdlan and/or a low-substituted hydroxypropylcellulose,

(32) a method of producing the compound according to (1), which comprises reacting a carboxylic acid of the formula (II):

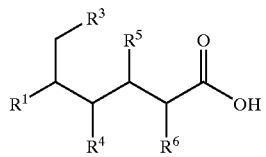

wherein $R^1$ represents an amino which may be substituted; $R^3$, $R^4$, $R^5$, and $R^6$ each represent a hydroxy group which may be protected, or a salt thereof, or a reactive derivative thereof; with a compound of the formula (III):

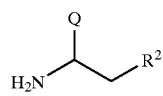

wherein $R^2$ represents a carboxy group which may be esterified or amidated; Q represents an aryl group which may be substituted, or a salt thereof,

(33) a method of producing the compound according to (1), which comprises reacting a compound of the formula (IV):

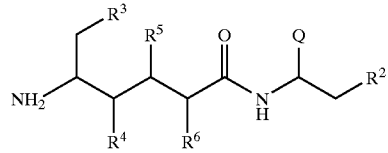

wherein $R^2$ represents a carboxyl group which may be esterified or amidated; $R^3$, $R^4$, $R^5$, and $R^6$ each represent a hydroxy group which may be protected, Q represents an aryl group which may be substituted, or a salt thereof, or a reactive derivative thereof; with a compound of the formula: $R^9$-X wherein $R^9$ represents an acyl group, or hydrocarbon group which may be substituted; X represents a leaving group or a salt thereof, or a reactive derivative thereof,

(34) a method of producing the compound according to (5), which comprises growing a strain of microorganism of the genus Bacillus which is capable of producing the compound according to (5) in a culture medium to let the strain produce and accumulate the compound in the fermentation broth and harvesting the same,

(35) the method according to (34), wherein the strain of microorganism is Bacillus sp. HC-70 or *Bacillus insolitus* HC-72,

(36) Bacillus sp. HC-70 or *Bacillus insolitus* HC-72 which is capable of producing the compound according to (5),

(37) a method for prevention or treatment of a disease associated with *Helicobacter pylori* infection in a mammal which comprises administering to the mammal in need an effective amount of a compound of the formula (I):

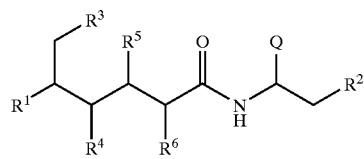

wherein $R^1$ represents amino which may be substituted; $R^2$ represents carboxy which may be esterified or amidated, $R^3$, $R^4$, $R^5$, and $R^6$ each represents hydroxy which may be protected; Q represents aryl which may be substituted; or a salt thereof, and

(38) use of a compound of the formula (I):

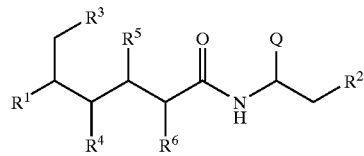

wherein $R^1$ represents amino which may be substituted; $R^2$ represents carboxy which may be esterified or amidated; $R^3$, $R^4$, $R_5$, and $R^6$ each represents hydroxy which may be protected; Q represents aryl which may be substituted; or a salt thereof, for the preparation of an anti-*Helicobacter pylori* agent.

DETAILED DESCRIPTION OF THE INVENTION

Figure 1:
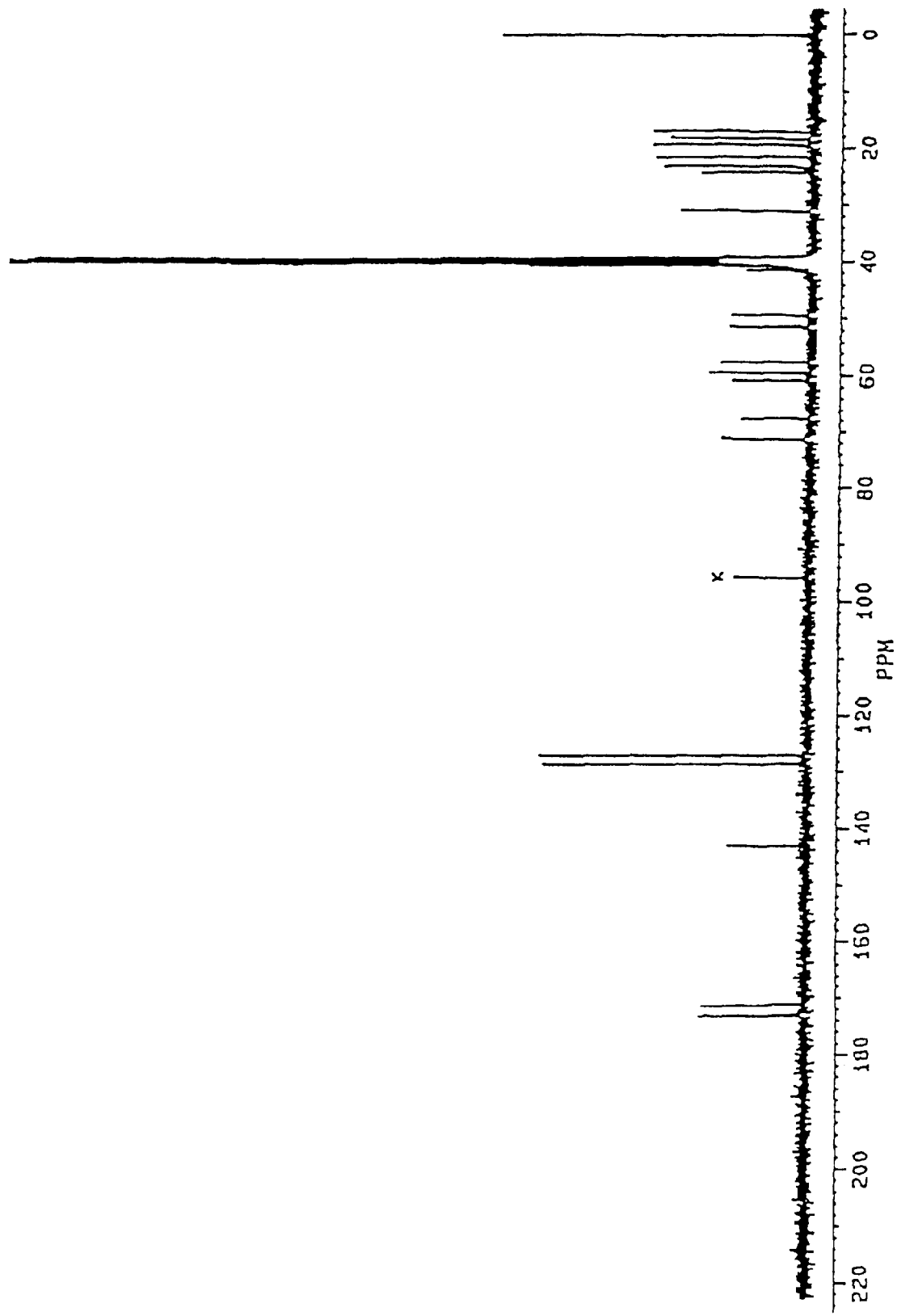
FIG. 1 is a $^{13}$C-NMR spectrum of HC-70I obtained in Example 2.

The "amino which may be substituted", as mentioned for $R^1$, includes amino, acylamino, and amino substituted by a hydrocarbon group which may be substituted.

The "acyl" of the "acylamino" for $R^1$ includes not only any one or a sequence of two or more of the "amino acid residues" to be mentioned hereinafter as an "amino acid residue" for $R^a$, $R^b$ or $R^c$ but also alkanoyl which may be substituted, aroyl which may be substituted, heterocycle-carbonyl which may be substituted, carbamoyl which may be substituted, thiocarbamoyl which may be substituted, alkylsulfonyl which may be substituted, arylsulfonyl which may be substituted, sulfamoyl which may be substituted, alkoxycarbonyl which may be substituted, and aryloxycarbonyl which may be substituted, among other acyl groups.

Among them, the sequence of two or more of the "amino acid residues" is particularly preferred.

The "alkanoyl" of said "alkanoyl which may be substituted" includes but is not limited to $C_{1-20}$ alkanoyl (e.g. formyl, acetyl, propionyl, isopropionyl, butyryl, pentanoyl, hexanoyl, heptanoyl, octanoyl, nonanoyl, lauroyl, undecanoyl, myristoyl, palmitoyl, stearoyl, etc.), and $C_{1-6}$ alkanoyl (e.g. formyl, acetyl, propionyl, isopropionyl, butyryl, pentanoyl, and hexanoyl) are particularly preferred.

The "aroyl" of said "aroyl which may be substituted" includes but is not limited to $C_{7-16}$ aroyl (e.g. benzoyl, 1-naphthoyl, 2-naphthoyl, etc.).

The "heterocycle-carbonyl" of said "heterocycle-carbonyl which may be substituted" includes 5- or 6-membered heterocycle-carbonyl groups or condensed heterocycle-carbonyl groups each of which contains 1 to 4 hetero atoms (e.g. nitrogen, oxygen, and sulfur) in addition to carbon as ring members (e.g. 3-pyrrolylcarbonyl, 1-imidazolylcarbonyl, 1-pyrazolylcarbonyl, 3-isothiazolylcarbonyl, 3-isoxazolylcarbonyl, pyrazinylcarbonyl, 2-pyrimidinylcarbonyl, 3-pyrazinylcarbonyl, 2-indolizinylcarbonyl, 2-isoindolylcarbonyl, 1-indolylcarbonyl, 2-furoyl, 2-thenoyl, nicotinoyl, isonicotinoyl, morpholinocarbonyl, piperidinocarbonyl, piperazinocarbonyl, etc.).

The "alkylsulfonyl" of said "alkylsulfonyl which may be substituted" includes but is not limited to $C_{1-20}$ alkylsulfonyl (e.g. methylsulfonyl, ethylsulfonyl, propylsulfonyl, isopropylsulfonyl, etc.).

The "carbamoyl which may be substituted" includes not only carbamoyl but also mono-substituted carbamoyl and di-substituted carbamoyl, where the substituent or substituents may be selected from among, for example, $C_{1-6}$ alkyl (e.g. methyl, ethyl, propyl, isopropyl, butyl, isobutyl, etc.), $C_{6-14}$ aryl (e.g. phenyl, 1-naphthyl, 2-naphthyl, etc.), $C_{7-16}$ aralkyl (e.g. benzyl etc.), $C_{1-6}$ alkanoyl (e.g. acetyl, propionyl, isopropionyl, butyryl, etc.), $C_{7-16}$ aroyl (e.g. benzoyl, 1-naphthoyl, 2-naphthoyl, etc.), 5- or 6-membered heterocycle-carbonyl (e.g. 3-pyrrolylcarbonyl, 2-imidazolylcarbonyl, 1-pyrazolylcarbonyl, 3-isothiazolylcarbonyl, 3-isoxazolylcarbonyl, pyrazinylcarbonyl, 2-pyrimidinylcarbonyl, 3-pyrazinylcarbonyl, 2-indolizinylcarbonyl, 2-isoindolylcarbonyl, 1-indolylcarbonyl, 2-furoyl, 2-thenoyl, nicotinoyl, isonicotinoyl, morpholinocarbonyl, piperidinocarbonyl, piperazinocarbonyl, etc.).

The "thiocarbamoyl which may be substituted" includes not only thiocarbamoyl but also mono-substituted thiocarbamoyl and di-substituted thiocarbamoyl, where the substituent or substituents may be selected from among, for example, $C_{1-6}$ alkyl (e.g. methyl, ethyl, propyl, isopropyl, butyl, isobutyl, etc.), $C_{6-14}$ aryl (e.g. phenyl, 1-naphthyl, 2-naphthyl, etc.), $C_{7-16}$ aralkyl (e.g. phenyl-$C_{1-5}$ alkyl such as benzyl etc.), $C_{1-6}$ alkanoyl (e.g. acetyl, propionyl, isopropionyl, butyryl, etc.), $C_{7-16}$ aroyl (e.g. benzoyl, 1-naphthoyl, 2-naphthoyl, etc.), 5- or 6-membered heterocycle-carbonyl (e.g. 5- or 6-membered heterocycle-carbonyl groups or condensed heterocycle-carbonyl groups each of which contains 1 to 4 hetero atoms (e.g. nitrogen, oxygen, and sulfur) in addition to carbon as ring members such as 3-pyrrolylcarbonyl, 2-imidazolylcarbonyl, 1-pyrazolylcarbonyl, 3-isothiazolylcarbonyl, 3-isoxazolylcarbonyl, pyrazinylcarbonyl, 2-pyrimidinylcarbonyl, 3-pyrazinylcarbonyl, 2-indolizinylcarbonyl, 2-isoindolylcarbonyl, 1-indolylcarbonyl, 2-furoyl, 2-thenoyl, nicotinoyl, isonicotinoyl, morpholinocarbonyl, piperidinocarbonyl, piperazinocarbonyl, etc.).

The "arylsulfonyl", of said "arylsulfonyl which may be substituted" includes but is not limited to $C_{6-14}$ arylsulfonyl (e.g. benzenesulfonyl, 1-naphthylsulfonyl, 2-naphthylsulfonyl, etc.).

The "sulfamoyl which may be substituted" includes not only sulfamoyl but also mono-substituted sulfamoyl and di-substituted sulfamoyl, where the substituent or substituents may be selected from among, for example, $C_{1-6}$ alkyl (e.g. methyl, ethyl, propyl, isopropyl, butyl, isobutyl, etc.), $C_{6-14}$ aryl (e.g. phenyl, 1-naphthyl, 2-naphthyl, etc.), and $C_{7-16}$ aralkyl (e.g. phenyl-$C_{1-5}$ alkyl such as benzyl etc.).

The "alkoxycarbonyl" of said "alkoxycarbonyl which may be substituted" includes but is not limited to $C_{1-20}$ alkoxy-carbonyl (e.g. methoxycarbonyl, ethoxycarbonyl, propoxycarbonyl, isopropoxycarbonyl, butoxycarbonyl, isobutoxycarbonyl, etc.).

The "aryloxycarbonyl" of said "aryloxycarbonyl which may be substituted" includes but is not limited to $C_{6-14}$ aryloxy-carbonyl (e.g. phenoxycarbonyl, 1-naphthyloxycarbonyl, 2-naphthyloxycarbonyl, etc.).

The "hydrocarbon group" of said "hydrocarbon group which may be substituted" may for example be an aliphatic hydrocarbon group or a cyclic hydrocarbon group. The "aliphatic hydrocarbon group" mentioned above includes but is not limited to $C_{1-20}$ aliphatic hydrocarbon groups (e.g. alkyl, alkenyl, and alkynyl). The "cyclic hydrocarbon group" includes $C_{3-20}$ cyclic hydrocarbon groups (e.g. cycloalkyl, cycloalkenyl, aryl, etc.).

The "alkyl" mentioned above is a $C_{1-10}$ alkyl group such as methyl, ethyl, propyl, 2-propyl, 1-ethylpropyl, butyl, 1-methylpropyl, 2-methylpropyl, 1,1-dimethylethyl, 1,1-dimethylbutyl, 2,2-dimethylbutyl, pentyl, 3-methylbutyl, 2,2-dimethylpropyl, hexyl, and so on.

The "alkenyl" is a $C_{2-10}$ alkenyl group such as ethenyl, 2-propenyl, 1-methylethenyl, butenyl, 2-methyl-1-propenyl, 2-methyl-2-propenyl, 1-methyl-2-propenyl, 2-pentenyl, 3-pentenyl, 4-pentenyl, 2-hexenyl, 3-hexenyl, 5-hexenyl, and so on.

The "alkynyl" is a $C_{2-10}$ alkynyl group such as ethynyl, 2-propynyl, 2-butyn-1-yl, 3-butyn-2-yl, 1-pentyn-3-yl, 3-pentyn-1-yl, 4-pentyn-2-yl, 3-hexyn-1-yl, and so on.

The "cycloalkyl" is a $C_{3-10}$ cycloalkyl group such as cyclopropyl, cyclobutyl, cyclopentyl, cyclohexyl, and so on.

The "cycloalkenyl" is a $C_{3-10}$ cycloalkenyl group such as cyclobutenyl, cyclopentenyl, cyclohexenyl, cyclohexadienyl, and so on.

The "aryl" is a $C_{6-14}$ aryl group such as phenyl, 1-naphthyl, 2-naphthyl, and so on.

Referring to the "hydrocarbon group" of said "hydrocarbon group which may be substituted" and the "acyl" of said "acylamino" for $R^1$, the substituent group that may optionally be present on said "alkanoyl, aroyl, heterocycle-carbonyl, alkylsulfonyl, arylsulfonyl, alkoxycarbonyl or aryloxycarbonyl" is not particularly restricted unless contary to the object of the invention, thus including amino, mono- or di-$C_{1-6}$ alkylamino (e.g. methylamino, ethylamino, propylamino, isopropylamino, dimethylamino, diethylamino, etc.), mono- or di-$C_{6-10}$ arylamino (e.g. phenylamino, diphenylamino, etc.), mono- or di-$C_{7-11}$ aralkylamino (e.g. phenyl-$C_{1-5}$ alkylamino such as benzylamino, di(phenyl-$C_{1-5}$ alkyl)amino such as dibenzylamino, etc.), azido, nitro, halogen (e.g. fluorine, chlorine, bromine, iodine), hydroxy, $C_{1-6}$ alkoxy (e.g. methoxy, ethoxy, propoxy, isopropoxy, butoxy, etc.), $C_{6-10}$ aryloxy (phenoxy, 1-naphthyloxy, 2-naphthyloxy, etc.), $C_{7-11}$ aralkyloxy (e.g. phenyl-$C_{1-5}$ alkoxy such as benzyloxy etc.), formyloxy, $C_{1-6}$ alkyl-carbonyloxy (e.g. acetoxy, propionyloxy, etc.), $C_{6-10}$ aryl-carbonyloxy (e.g. benzoyloxy etc.), $C_{7-11}$ aralkyl-carbonyloxy (e.g. phenyl-$C_{1-5}$ alkylcarbonyloxy such as benzylcarbonyloxy etc.), sulfonyloxy, $C_{1-6}$ alkylsulfonyloxy (e.g. methylsulfonyloxy etc.), mercapto, $C_{1-6}$ alkylthio (e.g. methylthio, ethylthio, propylthio, isopropylthio, etc.), $C_{6-10}$ arylthio (e.g. phenylthio, 1-naphthylthio, 2-naphthylthio, etc.), $C_{7-11}$ aralkylthio (e.g. phenyl-$C_{1-5}$ alkylthio such as benzylthio etc.), phosphonoxy, cyano, carbamoyl, mono- or di-$C_{1-6}$ alkyl-carbamoyl (e.g. methylcarbamoyl, ethylcarbamoyl, dimethylcarbamoyl, diethylcarbamoyl, etc.), mono- or di-$C_{6-10}$ aryl-carbamoyl (e.g. phenylcarbamoyl, diphenylcarbamoyl, etc.), mono- or di-$C_{7-11}$ aralkyl-carbamoyl (e.g. (phenyl-$C_{1-5}$ alkyl) carbamoyl such as benzylcarbamoyl, di(phenyl-$C_{1-5}$ alkyl) carbamoyl such as dibenzylcarbamoyl, etc.), carboxy, $C_{1-6}$ alkoxy-carbonyl (e.g. methoxycarbonyl, ethoxycarbonyl, etc.), $C_{6-10}$ aryloxy-carbonyl (e.g. phenoxycarbonyl, 1-naphthyloxycarbonyl, 2-naphthyloxycarbonyl, etc.), $C_{7-11}$ aralkyloxy-carbonyl (e.g. phenyl-$C_{1-5}$ alkyloxycarbonyl such as benzyloxycarbonyl etc.), formyl, $C_{1-6}$ alkyl-carbonyl (e.g. acetyl, propionyl, isopropionyl, butyryl, pentanoyl, hexanoyl, etc.), $C_{6-10}$ aryl-carbonyl (e.g. benzoyl, 1-naphthoyl, 2-naphthoyl, etc.), $C_{7-11}$ aralkyl-carbonyl (e.g. phenyl-$C_{1-5}$ alkylcarbonyl such as benzylcarbonyl etc.), sulfo, $C_{1-6}$ alkylsulfinyl (e.g. methylsulfinyl, ethylsulfinyl, etc.), $C_{6-10}$ arylsulfinyl (e.g. Benzenesulfonyl, 1-naphthylsulfinyl, 2-naphthylsulfinyl, etc.), $C_{1-6}$ alkylsulfonyl (e.g. methylsulfonyl, ethylsulfonyl, etc.), $C_{6-10}$ arylsulfonyl (e.g. benzenesulfonyl, 1-naphthylsulfonyl, 2-naphthylsulfonyl, etc.), $C_{1-6}$ alkyl (e.g. methyl, ethyl, propyl, isopropyl, butyl, isobutyl, sec-butyl, etc.), $C_{2-6}$ alkenyl (e.g. vinyl, allyl, 2-butenyl, etc.), $C_{2-6}$ alkynyl (e.g. ethynyl, propargyl, etc.), $C_{3-6}$ cycloalkyl (e.g. cyclopropyl, cyclobutyl, cyclopentyl, cyclohexyl, etc.), $C_{3-6}$ cycloalkenyl (e.g. cyclobutenyl, cyclopentenyl, cyclohexenyl, cyclohexadienyl, etc.), $C_{6-10}$ aryl (e.g. phenyl, 1-naphthyl, 2-naphthyl, etc.), mono- through tricyclic heterocyclic groups (e.g. heterocyclic groups consisting of one to three rings containing at least one 5- or 6-membered rings containing 1 to 4 hetero atoms selected from among nitrogen, oxygen, and sulfur: pyridyl, pyrazyl, pyrimidyl, quinolyl, isoquinolyl, indolyl, isoindolyl, indazolyl, pyridazinyl, imidazolyl, pyrazolyl, pyrrolyl, furyl, benzofuranyl, thienyl, benzothienyl, benzimidazolyl, quinazolyl, pyrrolidinyl, pyrrolinyl, imidazolidinyl, imidazolinyl, pyrazolidinyl, pyrazolinyl, piperidyl, piperazinyl, indolizinyl, isoindolizinyl, morpholinyl, etc.), and mono- through tricyclic heterocycle-thio (e.g. groups formed as thio is bound to the above-mentioned heterocyclic groups, such as 4-pyridylthio, 2-pyrimidylthio, 1,3,4-thiadiazol-2-ylthio, 5-tetrazolylthio, 2-benzothiazolylthio, 8-quinolylthio, etc.). Those substituent groups may be present on said "hydrocarbon group" and on said "alkanoyl, aroyl, heterocyclecarbonyl, alkylsulfonyl, arylsulfonyl, alkoxycarbonyl and aryloxycarbonyl" within the chemically permissible range and, in each instance, the number of substituents may range from 1 to 5, preferably 1~3. It should be understood that when the number of substituents is 2 or more, the substituent groups may be similar or dissimilar. Provided chemically permissible, those substituents, in turn, may each be substituted by 1 to 3 substituent groups selected from the class consisting of amino, mono- or di-$C_{1-6}$ alkylamino, nitro, halogen, hydroxy, $C_{1-6}$ alkoxy, $C_{1-6}$ alkyl-carbonyloxy, sulfonyloxy, $C_{1-6}$ alkylsulfonyloxy, mercapto, $C_{1-6}$ alkylthio, phosphonoxy, cyano, carbamoyl, mono- or di-$C_{1-6}$ alkyl-carbamoyl, carboxy, $C_{1-6}$ alkoxy-carbonyl, formyl, $C_{1-6}$ alkyl-carbonyl, sulfo, and $C_{1-6}$ alkylsulfinyl.

$R^1$ further includes groups of the formula $R^a$—$R^b$—$R^c$—NH—[$R^a$ represents hydrogen or an amino acid residue which may be substituted; $R^b$ and $R^c$ may be the same or different and each represents a bond, an amino acid residue which may be substituted, or Y—$R^d$—($R^d$ represents the group available upon elimination of imino from an amino acid residue which may be substituted; Y represents —O—, —S—, or —$NR^e$—($R^e$ represents hydrogen or lower alkyl))].

Provided that $R^a$, $R^b$, and/or $R^c$ is an amino acid residue, they are preferably joined together by an amide bondage.

The "amino acid" mentioned above with reference to the "amino acid residue" for $R^a$, $R^b$, and $R^c$ and to the "group available upon elimination of imino from an amino acid residue" for $R^d$ and to the "amino group substituted with an amino acid residue" for $R^1$ generally means a group available upon substitution of amino for at least one hydrogen atom of the nuclear structure of a carboxylic acid and includes α-, β-, γ- and δ-amino acids having a nucleic structure of 2 to 20 carbon atoms. Preferred among such amino acids are α-amino acids (especially α-L-amino acids) such as alanine, arginine, asparagine, aspartic acid, cysteine, glutamic acid, glutamine, glycine, histidine, leucine, isoleucine, lysine, methionine, phenylalanine, proline, serine, threonine, tryptophan, tyrosine, valine, etc. and such other amino acids as norvaline, norleucine, 2-aminoadipic acid, 2-aminobutyric acid, 2-aminoisobutyric acid, 2-amino-4-pentenoic acid, 1-aminocyclbpropanecarboxylic acid, 1-aminocyclopentanecarboxylic acid, 1-aminocyclohexanecarboxylic acid, thyronine, ornithine, hydroxyproline, hydroxylysine, (2-naphthyl)alanine, azaglycine, and so on.

The amino acid mentioned above includes cyclic imino acids. The "cyclic imino acid" means a compound available upon substitution of imino for at least one methylene group of a cycloalkanecarboxylic acid or cycloalkenecarboxylic acid, thus including proline, hydroxyproline, 3,4-dehydroproline, pipecolic acid

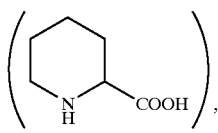

aziridinecarboxylic acid, and 2-azetidinecarboxylic acid

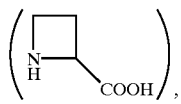

among others. Preferred are proline, hydroxyproline, and pipecolic acid.

The amino acid residue as the term is used in this specification may be any amino acid residue that is used generally in peptide chemistry and may for example be the residue of any of the amino acids mentioned hereinbefore.

The "group available upon elimination of imino (—NH—) from an amino acid residue", for $R^d$, may be a group available upon elimination of imino from the amino acid residue defined above, thus including groups derived from carboxylic acids having the following groups as the nuclear structure: straight-chain or branched $C_{1-10}$ alkyl (e.g. methyl, ethyl, propyl, isopropyl, butyl, isobutyl, sec-butyl, tert-butyl, pentyl, isopentyl, neopentyl, tert-pentyl, 1-ethylpropyl, hexyl, isohexyl, heptyl, octyl, decyl, etc.), $C_{2-10}$ alkenyl (e.g. vinyl, allyl, isopropenyl, 1-propenyl, 2-methyl-1-propenyl, 1-, 2- or 3-butenyl, 2-ethyl-1-butenyl, 3-methyl-2-butenyl, 1-, 2-, 3- or 4-pentenyl, 4-methyl-3-pentenyl, 1-, 2-, 3-, 4- or 5-hexenyl, and heptenyl, octenyl, and decenyl each having a double bond in an optional position), $C_{7-20}$ aralkyl (e.g. phenyl-$C_{1-5}$ alkyl such as benzyl, phenethyl, 3-phenylpropyl, naphtyl-$C_{1-5}$ alkyl such as 1-naphthylmethyl, 2-naphthylmethyl, 9-fluorenylmethyl, etc.), $C_{3-7}$ cycloalkyl (e.g. cyclopropyl, cyclobutyl, cyclopentyl, cyclohexyl, cycloheptyl, etc.), $C_{3-7}$ cycloalkenyl (e.g. 2-cyclopenten-1-yl, 3-cyclopenten-1-yl, 2-cyclohexen-1-yl, 3-cyclohexen-1-yl, etc.), $C_{6-15}$ aryl (e.g. phenyl, naphthyl, anthryl, phenanthryl, acenaphthylenyl, fluorenyl, etc.), and monocyclic or fused polycyclic $C_{3-20}$ heterocyclic alkyl groups (e.g. 4-imidazolylmethyl, 3-pyridylmethyl, 4-thiazolylmethyl, 3-indolylmethyl, 3-quinolylmethyl, etc.).

The above-mentioned amino acid residue and the above-mentioned group available upon elimination of imino from the amino acid residue may respectively have 1 or more substituents, preferably 1 to 3 substituents, in suitable positions, and the specific substituent group that may be present includes but is not limited to amino, acyl-substituted amino, guanidino, acylguanidino, acylamidino, amidino, acyl, carbamoyl, N-mono- or di-lower alkyl-carbamoyl, carboxy, lower alkoxy-carbonyloxy, hydroxy, acylhydroxy, lower alkoxy, phenoxy, mercapto, acylmercapto, lower alkyl-thio, phenylthio, sulfo, cyano, azido, nitro, nitroso, and halogen.

Here, the "acyl" of said "acyl-substituted amino, acylguanidino, acylamidino, acylhydroxy, or acylmercapto" includes the same acyl groups as mentioned hereinbefore for the "acyl" of the "acylamino" for $R^1$, especially $C_{1-20}$ alkanoyl (preferably $C_{1-6}$ alkanoyl).

The "lower alkyl" of said "lower alkyl-carbamoyl" includes but is not limited to $C_{1-6}$ alkyl groups such as methyl, ethyl, propyl, isopropyl, butyl, and isobutyl.

The "lower alkoxy-carbonyloxy" includes but is not limited to $C_{1-6}$ alkoxy-carbonyloxy groups such as methoxycarbonyloxy, ethoxycarbonyloxy, propoxycarbonyloxy, isopropoxycarbonyloxy, butoxycarbonyloxy, isobutoxycarbonyloxy, and so forth.

The "lower alkoxy" includes but is not limited to $C_{1-6}$ alkoxy groups such as methoxy, ethoxy, propoxy, isopropoxy, butoxy, isobutoxy, and so forth.

The "lower alkyl-thio" includes but is not limited to $C_{1-6}$ alkylthio groups such as methylthio, ethylthio, propylthio, isopropylthio, and so forth.

The lower alkyl for $R^e$ includes but is not limited to $C_{1-6}$ alkyl groups such as methyl, ethyl, propyl, isopropyl, butyl, pentyl, hexyl, and so forth.

The "α-L-amino acid" in the "amino group which may be substituted with a α-L-amino acid residue which may be substituted with a α-L-amino acid residue, for $R^7$, includes the same "α-L-amino groups" as mentioned hereinbefore for the "α-L-amino group" of the amino acid residue for $R^a$, $R^b$ and $R^c$.

The "hydrocarbon group which may be substituted", for $R^8$, includes the same "hydrocarbon groups which may be substituted" as exemplified hereinbefore for the substituent of the "amino group which may be substituted" for $R^1$. $R^8$ includes, for example, a $C_{1-10}$ alkyl group, a $C_{6-14}$ aryl-$C_{1-6}$ alkyl group, a $C_{2-10}$ alkenyl group, a $C_{2-10}$ alkinyl group and so on, each of which may be substituted. The preferable example for $R^8$ includes a $C_{1-6}$ alkyl group, a $C_{2-6}$ alkenyl group and a cyclopropyl-$C_{1-3}$ alkyl group, especially a isobutyl group and an allyl group.

The carboxy which may be esterified, for $R^2$, includes carboxy, (lower($C_{1-6}$)alkoxy)carbonyl (e.g. methoxycarbonyl, ethoxycarbonyl, propoxycarbonyl, isopropoxycarbonyl, butoxycarbonyl, isobutoxycarbonyl, tert-butoxycarbonyl, sec-butoxycarbonyl, pentyloxycarbonyl, isopentyloxycarbonyl, neopentyloxycarbonyl, tert-pentyloxycarbonyl, hexyloxycarbonyl, etc.), ($C_{6-10}$ aryl)oxycarbonyl (e.g. phenoxycarbonyl, 1-naphthoxycarbonyl, etc.), and ($C_{7-10}$ aralkyl)oxycarbonyl (e.g. (phenyl-$C_{1-4}$ alkyloxy)carbonyl such as benzyloxycarbonyl), diphenylmethyloxycarbonyl, pivaloyloxymethoxycarbonyl, 1-(cyclohexyloxycarbonyloxy)ethoxycarbonyl. Among them, carboxy, methoxycarbonyl, and ethoxycarbonyl are preferred.

The carboxy which may be amidated, for $R^2$, includes carbamoyl and substituted carbamoyl. The substituent group for said substituted carbamoyl includes but is not limited to unsubstituted or substituted lower($C_{1-6}$)alkyl (e.g. methyl, ethyl, propyl, isopropyl, butyl, isobutyl, sec-butyl, tert-butyl, pentyl, isopentyl, neopentyl, hexyl, isohexyl, etc.), unsubstituted or substituted $C_{3-6}$ cycloalkyl (e.g. cyclopropyl, cyclobutyl, cyclopentyl, cyclohexyl, etc.), unsubstituted or substituted $C_{6-10}$ aryl (e.g. phenyl, 1-naphthyl, 2-naphthyl, etc.), unsubstituted or substituted $C_{7-12}$ aralkyl (e.g. phenyl-$C_{1-4}$ alkyl such as benzyl and phenethyl, naphthyl-$C_{1-2}$ alkyl, etc.), and unsubstituted or substituted $C_{6-10}$ arylsulfonyl (e.g. benzenesulfonyl, 1-naphthalenesulfonyl, 2-naphthalenesulfonyl, etc.). One or 2 similar or dissimilar members selected from among the above-mentioned substituent groups may be present. The substituent group for such optionally substituted lower($C_{1-6}$)alkyl, optionally substituted $C_{3-6}$ cycloalkyl, optionally substituted $C_{6-10}$ aryl, optionally substituted $C_{7-12}$ aralkyl, and optionally substituted $C_{6-10}$ arylsulfonyl includes halogen (e.g. fluorine, chlorine, bromine, etc.), alkoxy (e.g. $C_{1-4}$ alkoxy such as methoxy, ethoxy, propoxy, etc.) which may be substituted by 1 to 3 halogen atoms, alkyl (e.g. $C_{1-4}$ alkyl such as methyl, ethyl, propyl, etc.) which may be substituted by 1 to 3 halogen atoms, amino, carboxy and nitro, and of those substituent groups, 1 to 5 members may be present.

The amino which may be substituted may be such that the two substituent groups on the nitrogen atom jointly form a cycloamino group in conjunction with the nitrogen atom, and such cycloamino group includes but is not limited to 1-azetidinyl, 1-pyrrolidinyl, piperidino, morpholino, thiomorpholino, and 1-piperazinyl.

$R^2$ is preferably a carboxyl group.

The "aryl" of the "aryl which may be substituted" for Q includes but is not limited to monocyclic or fused polycyclic $C_{6-14}$ aromatic hydrocarbon groups. The aromatic hydrocarbon groups mentioned above include but are not limited to phenyl, 1- or 2-naphthyl, 1-, 2-, or 9-anthryl, 1-, 2-, 3-, 4-, or 9-phenanthryl, and 1-, 2-, 4-, 5-, or 6-azulenyl. This "aryl" may have 1 to 5 suitable substituent groups, preferably 1 to 3 substituent groups, in substitutable positions, and such substituent groups include but are not limited to alkoxy (e.g. $C_{1-3}$ alkoxy such as methoxy, ethoxy, and propoxy), halogen (e.g. fluorine, chlorine, bromine, iodine), alkyl (e.g. $C_{1-3}$ alkyl such as methyl, ethyl, and propyl), amino, nitro, and cyano.

Q is preferably a phenyl group.

The protective group for the "hydroxy which may be protected" for $R^3$, $R^4$, $R^5$, and $R^6$ includes but is not limited to ether-forming protective groups such as methoxymethyl, benzyloxymethyl, tert-butoxymethyl, 2-methoxyethoxymethyl, 2-(trimethylsilyl)ethoxymethyl, methylthiomethyl, 2-tetrahydropyranyl, 4-methoxy-4-tetrahydropyranyl, 2-tetrahydropyranyl, benzyl, p-methoxybenzyl, p-nitrobenzyl, o-nitrobenzyl, 2,6-dichlorobenzyl, trityl, etc.; silyl ether-forming protective groups such as trimethylsilyl, triethylsilyl, triisopropylsilyl, isopropyldimethylsilyl, diethylisopropylsilyl, tert-butyldimethylsilyl, tert-butyldiphenylsilyl, tribenzylsilyl, triphenylsilyl, methyldiphenylsilyl, etc.; and ester-forming protective groups such as formyl, acetyl, chloroacetyl, dichloroacetyl, trichloroacetyl, pivaloyl, benzoyl, benzyloxycarbonyl, 2-bromobenzyloxycarbonyl, and so on. Aside from the above, the protective group further includes those groups involving two hydroxyl groups among $R^3$, $R^4$, $R^5$, and $R^6$, for example cyclic acetals such as methylene acetal, ethylidene acetal, 4-methoxyphenylethylidene acetal, benzylidene acetal, 2,2,2-trichloroethylidene acetal, etc., cyclic ketals such as isopropylidene ketal, cyclopentylidene ketal, cyclohexylidene ketal, cycloheptylidene ketal, 1-phenylethylidene ketal, 2,4-dimthoxybenzylidene ketal, etc. and cyclic orthoesters such as methoxymethylene acetal, ethoxymethylene acetal, and so on.

The preferable example for $R^3$, $R^4$, $R^5$ and $R^6$ is a hydroxyl group respectively.

The preferable structure of the compound of the formula (I) is exemplified by the sterostructure represented by the formula (V).

The technology for production of the above compound in accordance with the invention is now described.

The compound (I) or salt of the invention can be typically produced by reacting a carboxylic acid of formula (II)

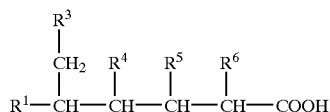

(II)

[wherein the respective symbols have the meanings defined hereinbefore] or a salt thereof, or a reactive derivative thereof, with a compound of formula (III)

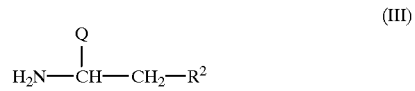

(III)

[wherein the respective symbols have the meanings defined hereinbefore] or a salt thereof.

The reactive derivative of said carboxylic acid for use in the above reaction can be prepared by, for example, the acid halide method, azide method, mixed acid anhydride method (the "counterpart acid" which can be used includes isobutyloxycarbonyl chloride, pivaloyl chloride, etc.), symmetric acid anhydride method, the method using a condensing agent such as N,N'-carbodiimidazole, N,N'-dicyclohexylcarbodiimide, N,N'-diisopropylcarbodiimide, 1-ethyl-3-(3-dimethylaminopropyl)carbodiimide, N-ethoxycarbonyl-2-ethoxy-1,2-dihydroquinoline, diethyl phosphorocyanidate, diphenylphosphoryl azide, 2-(1H-benzotriazol-1-yl)-1,1,3,3-tetramethyluronium tetrafluoroborate, 2-(1H-benzotriazol-1-yl)-1,1,3,3-tetramethyluronium hexafluorophosphate, benzotriazol-1-yloxytris(dimethylamino)phosphonium hexafluorophosphate, benzotriazol-1-yloxytrispyrrolidinophosphonium hexafluorophosphate, bromotrispyrrolidinophosphonium hexafluorophosphate, 2-(5-norbornene-2,3-dicarboximido)tetramethyluronium tetrafluoroborate, or the like, the method which comprises using the above condensing agent in the presence of 4-dimethylaminopyridine, 3-hydroxy-3,4-dihydro-4-oxo-1,2,3-benzotriazole, N-hydroxysuccinimide, N-hydroxy-5-norbornene-2,3-dicarboximide, 1-hydroxybenzotriazole or the like, or the active ester method using them.

The above reaction is generally conducted using 0.5 to 10 molar equivalents of compound (III) relative to compound (II) in a solvent. The solvent which can be used includes aromatic hydrocarbons such as benzene, toluene, xylene, etc.; halogenated hydrocarbons such as dichloromethane, chloroform, etc., saturated hydrocarbons such as hexane, heptane, cyclohexane, etc.; ethers such as diethyl ether, tetrahydrofuran, dioxane, etc.; nitrites such as acetonitrile etc.; sulfoxides such as dimethyl sulfoxide etc.; amides such as N,N-dimethylformamide etc.; esters such as ethyl acetate etc., and water. Those solvents can be used each alone or in a combination of 2 or more species, for example in a ratio of 1:1 through 1:10. The reaction temperature is usually about −80 to 100° C. and preferably about −50 to 50° C. The reaction time may range from about 1 to 96 hours, preferably about 1 to 72 hours.

The compound of formula (II) or salt can be synthesized typically by the method described in Acta Chemica Scandinavica B 36, 515–518 (1982).

The compound of formula (III) can be synthesized by a per se known method. A commercial product can also be used.

The compound (I) or salt of the invention can be synthesized by, for example, introducing a substituent group into the amino group of the compound (I) wherein $R^1 = NH_2$. The substituent group may for example be derived from a carboxylic acid or a salt thereof, or a reactive derivative thereof.

The compound (I) or its salt of the present invention can be produced, for example, by reacting a compound of the formula (IV) [wherein the respective symbols have the meanings defined hereinbefore] or a salt thereof, or a reactive derivative thereof, with a compound of the formula: $R^9$-X [wherein $R^9$ represents an acyl group and a hydrocarbon group which may be substituted and X represents a leaving group] or a salt thereof, or a reactive derivative thereof.

The "acyl" group for $R^9$ includes the same "acyl" groups as mentioned hereinbefore for the "acyl" group of the acylamino group for $R^1$. The preferable example of the acyl group for $R^9$ is any one or a sequence of two or more of the α-L-amino acid residues which may be protected as mentioned before, more preferably L-valyl-L-leucyl group which may be protected and (S)-2-amino-4-pentenoyl group which may be protected.

The "hydrocarbon" group for $R^9$ includes the same "hydrocarbon groups" as mentioned hereinbefore for the "hydrocarbon" group of the amino substituted by a hydrocarbon group which may be substituted for $R^1$.

The leaving group for X includes, for example, a hydroxyl group, halogen atom (e.g. fluorine, chlorine, bromine, especially chlorine), an azido group, a $C_{1-20}$ acyloxy group, a $C_{1-6}$ alkoxy group (e.g., methoxy, ethoxy, propoxy, isopropoxy, butoxy, etc.), a $C_{6-10}$ aryloxy group (e.g., phenoxy, 1-naphtyloxy, 2-naphtyloxy, etc.), a $C_{7-11}$ aralkyloxy group (e.g. benzyloxy, etc.), and so on.

The $C_{1-20}$ acyloxy group as a leaving group for X includes, for example, a $C_{1-20}$ alkanoyloxy group, preferably a $C_{1-6}$ alkanoyloxy group (e.g., formyloxy, acetoxy, propionyloxy, isopropionyloxy, butyryloxy, pentanoyloxy, hexanoyloxy, heptanoyloxy, octanoyloxy, nonanoyloxy, etc.), a $C_{7-16}$ aroyloxy group (e.g. benzoyloxy, 1-naphtoyloxy, 2-naphtoyloxy, etc.), a 5- or 6-membered heterocyclic group-carbonyloxy or a condensed heterocyclic group-carbonyloxy (e.g. 3-pyrrolylcarbonyloxy, 1-imidazolylcarbonyloxy, 1-pyrazolylcarbonyloxy, 3-isothiazolylcarbonyloxy, 3-isoxazolylcarbonyloxy, pyrazinylcarbonyloxy, 2-pyrimidinylcarbonyloxy, 3-pyrazinylcarbonyloxy, 2-indolizinylcarbonyloxy, 2-isoindolylcarbonyloxy, 1-indolylcarbonyloxy, 2-furoyloxy, 2-thenoyloxy, nicotinoyloxy, isonicotinoyloxy, morpholinocarbonyloxy, piperidinocarbonyloxy, piperazinocarbonyloxy, etc.), a carbamoyloxy group, a mono-substituted carbamoyloxy group or a di-substituted carbamoyloxy group (wherein the substituent includes the same substituent as mentioned hereinbefore for the "carbamoyl which may be substituted" as an acyl group of the acylamino group for $R^1$, a thiocarbamoyloxy group, a mono-substituted thiocarbamoyloxy group or a di-substituted thiocarbamoyloxy group (wherein the substituent includes the same substituent as mentioned hereinbefore for the "thiocarbamoyl which may be substituted" as an acyl group of the acylamino group for $R^1$, a $C_{1-20}$ alkylsulfonyloxy group, especially a $C_{1-6}$ alkylsulfonyloxy group (e.g. methylsulfonyloxy, ethylsulfonyloxy, propylsulfonyloxy, etc.), a $C_{6-14}$ arylsulfonyloxy group which may be substituted by one or more $C_{1-3}$ alkyl groups (e.g. benzenesulfonyloxy, 1-naphthylsulfonyloxy, 2-naphthylsulfonyloxy, toluenesulfonyloxy, etc.), a sulfamoyloxy group, a mono-substituted sulfamoyloxy group or a di-substituted sulfamoyloxy group, (wherein the substituent includes the same substituent as mentioned hereinbefore for the "sulfamoyl which may be substituted" as an acyl group of the acylamino group for $R^1$, a $C_{1-20}$ alkoxy-carbonyloxy group, especially a $C_{1-6}$ alkoxy-carbonyloxy group (e.g. methoxycarbonyloxy, ethoxycarbonyloxy, propoxycarbonyloxy, etc.), a $C_{6-14}$ aryloxy-carbonyloxy group (e.g. phenoxycarbonyloxy, 1-naphthyloxycarbonyloxy, 2-naphthyloxycarbonyloxy, etc.), and so on.

The preferable example of the leaving group for X is a hydroxyl group, halogen atom, an azido group, a $C_{1-20}$ acyloxy group, more preferably a hydroxyl group and halogen atom.

The conditions of this reaction and the method of synthesizing said carboxylic acid derivative may for example be the same as those mentioned hereinbefore in connection with the reaction between compound (II) and compound (III).

Whether the bond between the respective units of $R^a$, $R^b$, and $R^c$ in the formula $R^a$—$R^b$—$R^c$ is an amide bond or an ester bond, the carboxyl function of $R^d$ whose other functional group or groups may be suitably protected beforehand can be activated and condensed with the mating amine or alcohol compound which may also be suitably protected beforehand. If necessary, this condensation product is partially purified and deprotected in part. Then, the product may be further subjected to a similar condensation reaction. Or when the condensation product is a protected end product, all the protective groups are eliminated and the product is purified, where necessary, to provide a pure end product.

The following protective groups can be used for the protection of the amino, carboxy, hydroxy, and carbonyl groups used in the above series of synthetic reactions.

The amino-protecting group which can be used includes amide-forming protective groups such as formyl, acetyl, chloroacetyl, dichloroacetyl, trichloroacetyl, trifluoroacetyl, acetoacetyl, o-nitrophenylacetyl, etc.; carbamate-forming protective groups such as tert-butoxycarbonyl, benzyloxycarbonyl, p-methoxybenzyloxycarbonyl, p-nitrobenzyloxycarbonyl, 2-chlorobenzyloxycarbonyl, 2,4-dichlorobenzyloxycarbonyl, benzhydryloxycarbonyl, 2,2,2-trichloroethoxycarbonyl, 2-trimethylsilylethoxycarbonyl, 1-methyl-1-(4-biphenyl)ethoxycarbonyl, 9-fluorenylmethoxycarbonyl, 9-anthrylmethoxycarbonyl, isonicotinyloxycarbonyl, 1-adamantyloxycarbonyl, etc.; trityl, and phthaloyl.

The hydroxy-protecting group which can be used includes ether-forming protective groups such as methoxymethyl, benzyloxymethyl, tert-butoxymethyl, 2-methoxyethoxymethyl, 2-(trimethylsilyl)ethoxymethyl, methylthiomethyl, 2-tetrahydropyranyl, 4-methoxy-4-tetrahydropyranyl, 2-tetrahydropyranyl, benzyl, p-methoxybenzyl, p-nitrobenzyl, o-nitrobenzyl, 2,6-dichlorobenzyl, trityl, etc.; silyl ether-forming protective groups such as trimethylsilyl, triethylsilyl, triisopropylsilyl, isopropyldimethylsilyl, diethylisopropylsilyl, tert-butyldimethylsilyl, tert-butyldiphenylsilyl, tribenzylsilyl, triphenylsilyl, methyldiphenylsilyl, etc.; and ester-forming protective groups such as fcormyl, acetyl, chloroacetyl, dichloroacetyl, trichloroacetyl, pivaloyl, benzoyl, benzyloxycarbonyl, 2-bromobenzyloxycarbonyl, and so on.

The carboxy-protecting group which can be used includes ester-forming protective groups such as methyl, ethyl, methoxymethyl, methoxyethoxymethyl, benzyloxymethyl, tert-butyl, benzyl, p-methoxybenzyl, p-nitrobenzyl, o-nitrobenzyl, benzhydryl, trityl, 2,2,2-trichloroethyl, 2-trimethylsilylethyl, allyl, cyclohexyl, cyclopentyl, phenacyl, etc.; silyl ester-forming protective groups such as trimethylsilyl; triethylsilyl, tert-butyldimethylsilyl, isopropyldimethylsilyl, dimethylphenylsilyl, and so on.

The carbonyl-protecting group includes acetal-, ketal-, dithioacetal-, or dithioketal-forming protective groups, such as dimethyl, diethyl, dibenzyl, diacetyl, etc.; protective groups forming optionally substituted 1,3-dioxane or 1,3-dioxolane, protective groups forming 1,3-dithiane or 1,3-dithiolane, and protective groups forming N,N-dimethyl, 2,4-dinitrophenyl, and other substituted hydrazones.

The technology for removing such amino-protecting, hydroxy-protecting, carbonyl-protecting, and carboxy-protecting groups includes the method using an acid, the method using a base, the reduction method, the ultraviolet method, the hydrazine method, the phehylhydrazine method, the sodium N-methyldithiocarbamate method, the tetrabutylammonium fluoride method, the palladium acetate method, the mercury chloride method, and the Lewis acid method. Those routine methods and/or other known methods can be selectively used.

The method using an acid is one of the common methods for hydrolyzing an amide, ester, silyl ester, or silyl ether, and is applied to elimination of the corresponding type of protective group. For example, the method is commonly used for deprotection of an amino group protected by tert-butoxycarbonyl, p-methoxybenzyloxycarbonyl, benzhydryloxycarbonyl, 9-anthrylmethoxycarbonyl, 1-methyl-1-(4-biphenyl)ethoxycarbonyl, adamantyloxycarbonyl, or trityl and the deprotection of a hydroxyl group protected by methoxymethyl, tert-butoxymethyl, 2-tetrahydropyranyl, 4-methoxy-4-tetrahydropyranyl, 2-tetrahydrofuranyl, or trityl. The preferred acid includes organic acids such as formic acid, trifluoroacetic acid, benzenesulfonic acid, p-toluenesulfonic acid, etc. and inorganic acids such as hydrochloric acid, hydrobromic acid, sulfuric acid, and so on.

The method using a base, like the above method using an acid, is one of the common methods for hydrolyzing an amide, ester, or the like bond and is applied to elimination of the corresponding type of protective group. For example, organic bases can be used with advantage for deprotection of an amino group protected by 9-fluorenylmethoxycarbonyl. The preferred base includes such inorganic bases as alkali metal hydroxides, e.g. lithium hydroxide, sodium hydroxide, potassium hydroxide, etc.; alkaline earth metal hydroxides, e.g. magnesium hydroxide, calcium hydroxide, etc.; alkali metal carbonates, e.g. sodium carbonate, potassium carbonate, etc.; alkaline earth metal carbonates, e.g. magnesium carbonate, calcium carbonate, etc.; alkali metal hydrogencarbonates, e.g. sodium hydrogencarbonate, potassium hydrogencarbonate, etc.; alkali metal acetates, e.g. sodium acetate, potassium acetate, etc.; alkaline earth metal phosphates, e.g. calcium phosphate, magnesium phosphate, etc.; alkali metal hydrogenphosphate, e.g. disodium hydrogenphosphate, dipotassium hydrogenphosphate, etc.; and aqueous ammonia; and such organic bases as trimethylamine, triethylamine, diisopropylethylamine, pyridine, picoline, N-methylpyrrolidine, piperidine, N-methylpiperidine, N-methylmorpholine, 1,5-diazabicyclo[4.3.0]non-5-ene, 1,4-diazabicyclo[2.2.2]octane, 1,8-diazabicyclo[5.4.0]-7-undecene, and so on.

The reduction method is used typically for the deprotection of an amino group protected by trichloroacetyl, trifluoroacetyl, o-nitrophenylacetyl, 2,2,2-trichloroethoxycarbonyl, benzyloxycarbonyl, p-nitrobenzyloxycarbonyl, 2,4-dichlorobenzyloxycarbonyl, isonicotinyloxycarbonyl, trityl, or the like; the deprotection of a hydroxyl group protected by benzyl, p-nitrobenzyl, or the like; and the protection of a carboxyl group protected by benzyloxymethyl, benzyl, p-nitrobenzyl, phenacyl, 2,2,2-trichloroethyl, benzhydryl, or the like. The preferred mode of reduction includes reduction with sodium borohydride, reduction with zinc/acetic acid, and catalytic reduction.

The ultraviolet method is applied typically to the deprotection of a hydroxyl or carboxyl group protected by o-nitrobenzyl.

The hydrazine method is typically applied to the deprotection of an amino group protected by phthaloyl (e.g. phthalimide group).

The phenylhydrazine method is typically applied to the deprotection of an amino group protected by acetoacetyl.

The sodium N-methyldithiocarbamate method is typically applied to the deprotection of a chloroacetyl-protected amino or hydroxyl group.

The tetrabutylammonium fluoride method is typically used for deprotecting a 2-trimethylsilylethylcarbamate, silyl ether, or silyl ester to regenerate an amino group, a hydroxyl group or a carboxyl group as the case may be.

The palladium acetate method is typically used for deprotecting an allyl ester to regenerate a carboxyl group.

The mercury chloride method is typically applied to the deprotection of a hydroxyl group protected by methylthiomethyl.

The Lewis acid method is typically applied to the deprotection of a hydroxyl group protected by 2-methoxyethoxymethyl. The preferred Lewis acid includes zinc bromide and titanium tetrachloride, among other compounds.

The intermediates, reaction products, and end products as produced by the above series of reactions can be isolated and purified as necessary by known purification procedures or procedures analogous thereto, for example by concentration, concentration under reduced pressure, solvent extraction, crystallization, recrystallization, redistribution, and chromatography.

As an alternative method for production, the compound of the invention [for example, the compound of the above items (12), (13), (14), (15) and (16)] can be produced microbiologically.

The microorganism which can be employed in practicing the production method of the invention includes Bacillus sp. HC-70 (hereinafter referred to sometimes as strain HC-70) which was isolated from the soil in Nara Prefecture, Japan and *Bacillus insolitus* HC-72 (hereinafter referred to sometimes as strain HC-72) which was isolated from the soil in Aichi Prefecture, Japan.

The taxonomical investigation of strain HC-70 according to the routine methodology revealed that this microorganism is a gram-positive motile facultatively anaerobic rod and that its cell size is 1.3 to 1.4 $\mu$m×3.0 to 4.2 $\mu$m. Endospore formation is observed. The spore is ellipsoidal and the position of the spore is central of the cell; the sporangium swollen is not observed. As chemotaxonomical characteristics of this strain, its cell wall diaminopimelic acid is meso-diaminopimelic acid (meso-DAP), the main menaquinone is menaquinone-7 (MK-7), and the G+C content of the DNA is 35.0 mol %. The main cellular fatty acid is iso-$C_{15:0}$, $C_{16:0}$, anteiso-$C_{17:0}$. According to the classification criteria given in Bergey's Manual of Systematic Bacteriology Vol. 2, this strain is a microorganism of the genus Bacillus (Bacillus sp.). This strain shows abundant growth on bouillon agar and hydrolyzes casein, gelatin, and starch.

The taxonomical investigation of strain HC-72 carried out in the usual way revealed that this microorganism is a gram-positive motile aerobic rod and that its cell size is 1.3×3.0 to 4.2 $\mu$m. The endospore is spherical and the position of the spore is central of the cell; the sporangium swollen is not observed. As chemotaxonomical characteristics of this strain, meso-diaminopimelic acid (meso-DAP) is not detected as the cell wall component, the isoprenoid quinone is menaquinone-7 (MK-7), and the G+C content of the DNA is 36.8 mol %. The main cellular fatty acid is iso-$C_{15:0}$, anteiso $C_{16:1}$, anteiso-$C_{17:1}$. According to the classification criteria given in Bergey's Manual of Systematic Bacteriology Vol. 2, this strain is an organism belonging to the genus Bacillus (Bacillus sp.). Moreover, none of acid production from sugars, gelatin hydrolysis and sodium chloride requirement was found. Therefore, this microorganism was identified to be *Bacillus insolitus*.

The above Bacillus sp. HC-70 has been deposited with Institute for Fermentation, Osaka (IFO) as of Jun. 20, 1997 under the accession number of IFO 16098. In addition, this microorganism has been deposited with National Institute of Bioscience and Human Technology (NIBH, 1-3, Higashi 1-chome, Yatabe-cho, Tsukuba-shi, Ibaraki, Japan) as of Jul. 2, 1997 under the accession number of FERM BP-6001.

The above *Bacillus insolitus* HC-72 has been deposited with IFO as of Jun. 1, 1998 under the accession number of IFO 16179. In addition, this microorganism has been deposited with NIBH as of Jul. 8, 1998 under the accession number of FERM BP-6385.

As a general trait possessed by microorganisms, Bacillus species also undergo mutation, whether spontaneously or upon mutagenic treatment. Thus, for example, many mutants obtained by irradiation with X-rays, gamma-rays, or ultraviolet light, or obtained after treatment with various mutagens, or obtained from culture grown on media containing various mutagens, or other means as well as spontaneous mutants can all be utilized for the purposes of the invention unless they are devoid of the ability to elaborate HC-70 related substances (e.g. HC-70I, HC-70II, HC-70III, HC-70I-A, HC-70I-B and so on).

The culture medium for use in the method of the invention may be liquid or solid, only if it contains nutrients which the particular strain is able to utilize, although a liquid medium is preferred for high production. Incorporated in the medium are assimilable carbon sources, digestable nitrogen sources, inorganic matter, and trace nutrients. The carbon sources include but are limited to glucose, lactose, sucrose, maltose, dextrin, starch, glycerol, mannitol, sorbitol, myo-inositol, oils and fats (e.g. soybean oil, olive oil, rice bran oil, sesame oil, lard oil, chicken oil, etc.). The nitrogen sources include but are not limited to meat extract, yeast extract, dried yeast, soybean flour, corn steep liquor, peptone, cottonseed flour, cane molasses, urea, and ammonium salts (e.g. ammonium sulfate, ammonium chloride, ammonium nitrate, ammonium acetate, etc.). In addition, salts of sodium, potassium, calcium, magnesium, etc., salts of other metals such as iron, manganese, zinc, cobalt, nickel, etc.), salts of phosphoric acid, boric acid, etc., and salts of organic acids such as acetic acid, propionic acid, etc. are selectively used in suitable amounts. Furthermore, amino acids (e.g. glutamic acid, aspartic acid, alanine, lysine, valine, methionine, proline, etc.), vitamins (e.g. vitamin $B_1$ and $B_2$, nicotinic acid, vitamin $B_{12}$ and C, etc.), and nucleic acids (e.g. purine nucleotide, pyrimidine nucleotide and their derivatives) can also be incorporated. Of course, for the purpose of adjusting the pH of the medium, an inorganic or organic acid, an alkali, or/and a buffer can be added. As an antifoam, an oil or a surfactant can also be added in a suitable amount.

A suitable cultural technique can be selected from among stationary culture, shake culture, and aerated submerged culture. For mass processing, the so-called aerated submerged culture is preferred, of course.

The cultural conditions are of course dependent upon the type and composition of the medium used, the particular strain, and the cultural method chosen but the incubation temperature is usually 15 to 37° C. and the initial pH is around 5 to 9. Particularly, the culture mid-phase temperature is preferably 20 to 30° C. and the initial pH is preferably about 6 to 8. The incubation time is also dependent on the above-mentioned conditions but cultivation should be continued until the accumulation of the objective compound would reach a maximal level. The necessary incubation time is generally about 1 to 10 days for shake or aeration culture in a liquid medium.

Under the above cultural conditions, the compounds HC-70I, II, and III, which will be described hereinafter, are produced and accumulated and the respective compounds can then be extracted and purified according to their specific chemical properties. The objective HC-70I, II, and III can be harvested from the culture broth by suitable techniques selected from among the techniques which are generally used for harvesting microbial metabolites from culture broths. For example, since HC-70I, II, and III are water-soluble amphoteric compounds and occur for the most part in the culture supernatant, the cells are first removed from the broth by filtration or centrifugation.

The culture supernatant thus separated can be further purified by well-known chromatographic methods to provide pure HC-70I, II, and III. The chromatographic stationary phase which can be used for this purpose includes those stationary phases which utilize a differential adsorptive affinity for substrate compounds, such as activated carbon [e.g. active charcoal for chromatography, granular carbon "Shirasagi" (Takeda Chemical Industries, Ltd.), etc.], adsorbent resin [e.g. DIAION HP-20, HP-20S, or HP-20SS, SEPABEADS SP-207 or SP-850 (Mitsubishi Chemical Co., Ltd.), Amberlite XAD-I or XAD-II (Rohm & Haas Co., U.S.A.), etc.], microcrystalline cellulose [e.g. Avicel (Asahi Chemical Industry Co., Ltd.), Funacel (Funakoshi Co., Ltd.), etc.], and silica gel [e.g. Kieselguhr 60 (Merck &. Co., Germany) etc.]; those stationary phases which utilize specific functional groups such as cation exchange resin [e.g. Amberlite IR-120, IRC-50, or CG-50 (Rohm & Haas Co., U.S.A.), Dowex 50W (Dow Chemical Co., U.S.A.), DIAION PK-216 or UBK-510L (Mitsubishi Chemical Co.), and CNP-80 (Bayer, Germany) etc.], anion exchange resin [e.g. Amberlite IRA-402, IRA-67 or IRA-68 (Rohm & Haas Co., U.S.A.), Dowex 1 (Dow Chemical Co., U.S.A.), DIAION SA-21A, PA-406, PA-412, or WA-30 (Mitsubishi Chemical) etc.], ion exchange cellulose [CM-cellulose (Pharmacia, Sweden) etc.], ion exchange Sephadex [e.g. QAE-Sephadex or CM-Sephadex (Pharmacia, Sweden) etc.]; and those utilizing a molecular weight differential, such as molecular sieves [e.g. Sephadex G10 or LH-20 (Pharmacia, Sweden) etc.].

The solvent for use as a chromatographic mobile phase is dependent upon the type and properties of solid phase and may for example be any one or a suitable mixture of such solvents as water, aqueous solutions of alkalies (e.g. sodium hydroxide, potassium hydroxide, sodium hydrogencarbonate, ammonia, etc.), aqueous solutions of acids (e.g. hydrochloric acid, sulfuric acid, acetic acid, formic acid, phosphoric acid, etc.), salt-containing aqueous solutions (e.g. sodium chloride solution, acetate buffer, phosphate buffer, etc.) and water-miscible organic solvents (e.g. methanol, ethanol, isopropyl alcohol, acetone, acetonitrile, etc.).

For the purification of the objective compound in the practice of the invention, preparative high-performance liquid chromatography (HPLC) can also be utilized with advantage. When this method is used, the stationary phase is preferably one in the octadecylsilane (ODS) series, the polymer series, or the silica gel series. As an ODS series stationary phase, YMC gel (YMC) or TSK gel (Tosoh), for instance, can be typically mentioned. As a polymer series stationary phase, ODP (Asahi Chemical Industry Co., Ltd.) which is an octadecylated polymer or NH2P (Asahi Chemical Industry Co., Ltd.) which is a polyamine-modified polymer, for instance, can be selected. As to the mobile phase, water, an acidic aqueous solution, a salt-containing aqueous solution, methanol, acetonitrile, etc. can be used each alone or as a suitable mixture.

For the purification of the objective compound of the invention, crystallization is also a useful technique. As the crystallization solvent, water, methanol, ethanol, isopropyl alcohol, acetone, acetonitrile, etc. can be used each alone or as a suitable mixture.

HC-70I-A and HC-70I-B also can be obtained and purified from the culture (fermentation) broth according to the same method mentioned above.

The physicochemical properties of HC-70I, II, and III as obtained in Examples 1 and 2 which appear hereinafter, are as follows. Those compounds are sometimes designated as Compound 1, Compound 2, and Compound 3, respectively.

HC-70I (Compound 1)
1) Appearance: colorless crystals
2) Optical rotation: −89° (c=0.53, 0.1N HCl, 24° C.)
3) Molecular weight: FAB-MS m/z 654 (M+H)
4) Elemental analysis: (%) (calcd. as containing 1 mol of $H_2O$) Found : C, 55.23; H, 8.03; N, 10.47 Calcd.: C, 55.43; H, 7.95; N, 10.42
5) Molecular formula: $C_{31}H_{51}N_5O_{10}$
6) UV spectrum: λmax (ε) In water, 258 nm (310)
7) IR spectrum: KBr; dominant absorptions (wave-number, $cm^{-1}$): 3300, 2960, 1640, 1540, 1400, 1050, 700
8) $^{13}$C-NMR spectrum: DMSO-$d_6$, chemical shifts (75 MHz, δ ppm; FIG. 1) 172.8, 172.6, 172.4, 172.3, 170.7, 142.6, 128.0, 126.5, 126.5, 71.0, 70.9, 67.2, 60.5, 59.1, 57.2, 51.1, 50.9, 49.0, 41.1, 40.5, 30.9, 30.7, 24.0, 23.0, 21.3, 19.3, 19.1, 18.1, 16.8
9) Amino acid analysis: after 72 hr of hydrolysis in 6N-HCl at 110° C.) Leucine (1 mol), valine (2 mols)
10) Color reactions:
Positive: ninhydrin, Greig-Lieback
Negative: Ehrlich, Sakaguchi
11) High-performance liquid chromatography (HPLC):
Column: YMC-Pack ODS-A, A-312, 150×6.0 mm (YMC)
Mobile phase: 15% (v/v) acetonitrile/0.02 M
phosphate buffer (pH 4.5)
Flow rate: 1.0 mL/min.
Detection: UV absorptiometry, 214 nm
Retention time: 16.8 min.
12) Thin-layer chromatography (TLC):
Stationary phase: silica gel $60F_{254}$, 0.25 mm (Merck, Germany)
Developing solvent: n-butanol/acetic acid/water (12:3:5)
Rf: 0.45

HC-70II (Compound 2)
1) Appearance: colorless crystals
2) Optical rotation: −69° (c=0.50, 0.1N HCl, 24° C.)
3) Molecular weight: FAB-MS m/z 555 (M+H)$^+$
4) Elemental analysis: (%) (calcd. as containing 3 mols of $H_2O$) Found : C, 51.44; H, 7.84; N, 9.32 Calcd.: C, 51.30; H. 7.95; N, 9.20

Figure 2:
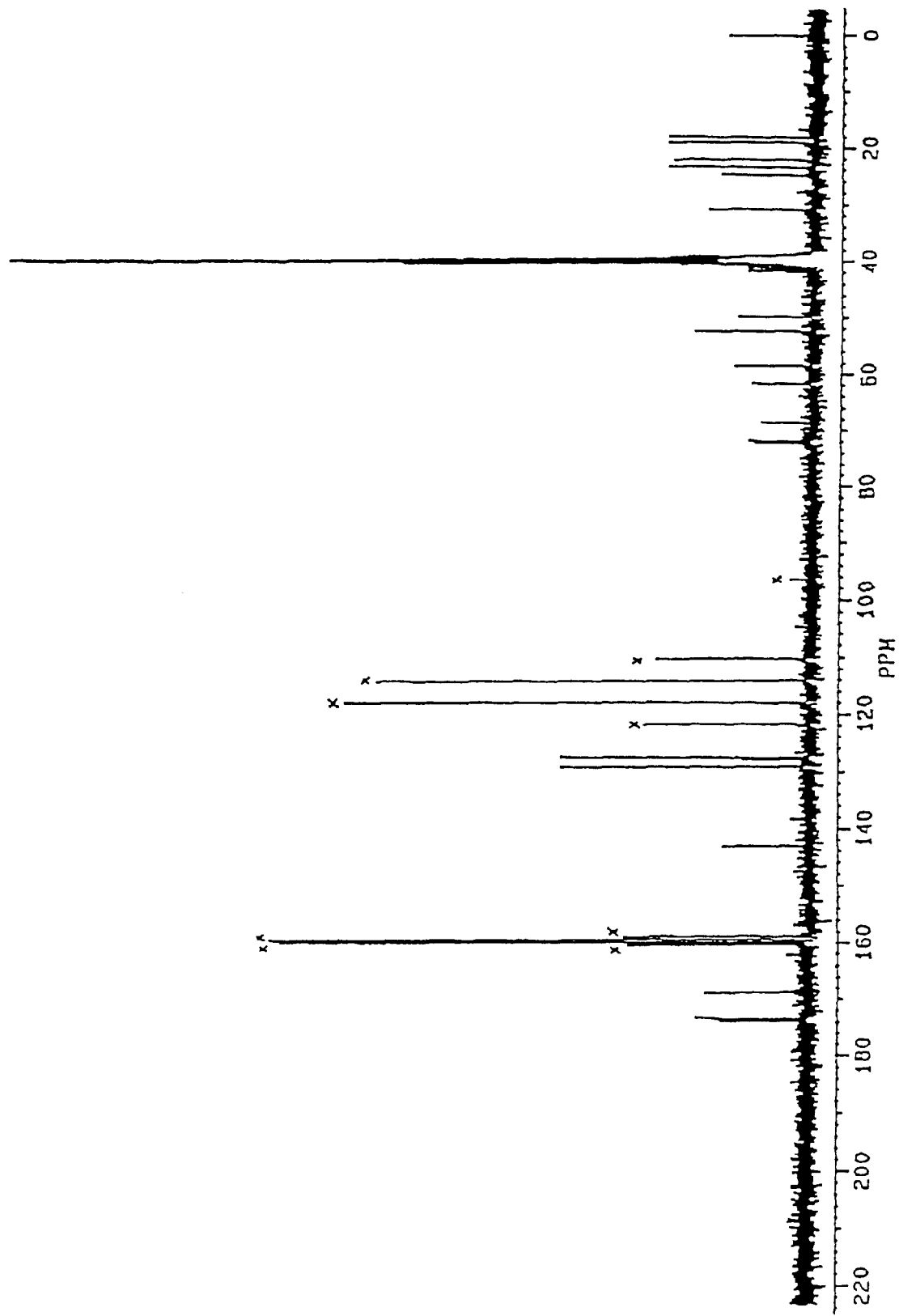
FIG. 2 is a $^{13}$C-NMR spectrum of HC-70II obtained in Example 1.

5) Molecular formula: $C_{26}H_{42}N_4O_9$
6) UV spectrum: λmax (ε) In water, 257nm (270)
7) IR spectrum: KBr, dominant absorptions (wave-number, $cm^{-1}$) 3370, 2970, 2940, 1680, 1630, 1520, 1400, 1050, 690
8) $^{13}$C-NMR spectrum: DMSO-$d_6$/trifluoroacetic acid (9:1), chemical shifts (75 MHz, δ ppm; FIG. 2) 173.3, 173.0, 172.7, 168.3, 142.6, 128.7, 127.4, 127.1, 71.9, 71.5, 68.1, 61.2, 58.0, 52.0, 49.5, 41.5, 40.8, 30.5, 24.6, 23.4, 21.9, 18.8, 17.9
9) Amino acid analysis: after 24 hr of hydrolysis in 6N-HCl at 110° C.) Leucine (1 mol), valine (1 mol)
10) Color reactions:
Positive: ninhydrin, Greig-Lieback
Negative: Ehrlich, Sakaguchi
11) High-performance liquid chromatography (HPLC):
Column: YMC-Pack ODS-A, A-312, 150×6.0 mm (YMC)
Mobile phase: 15% (v/v) acetonitrile/0.02 M
phosphate buffer (pH 4.5)
Flow rate: 1.0 mL/min.
Detection: UV absorptiometry, 214 nm
Retention time: 8.1 min.
12) Thin-layer chromatography (TLC):
Stationary phase: silica gel $60F_{254}$, 0.25 mm (Merck, Germany)
Developing solvent: n-butanol/acetic acid/water (12:3:5)
Rf: 0.41

Figure 3:
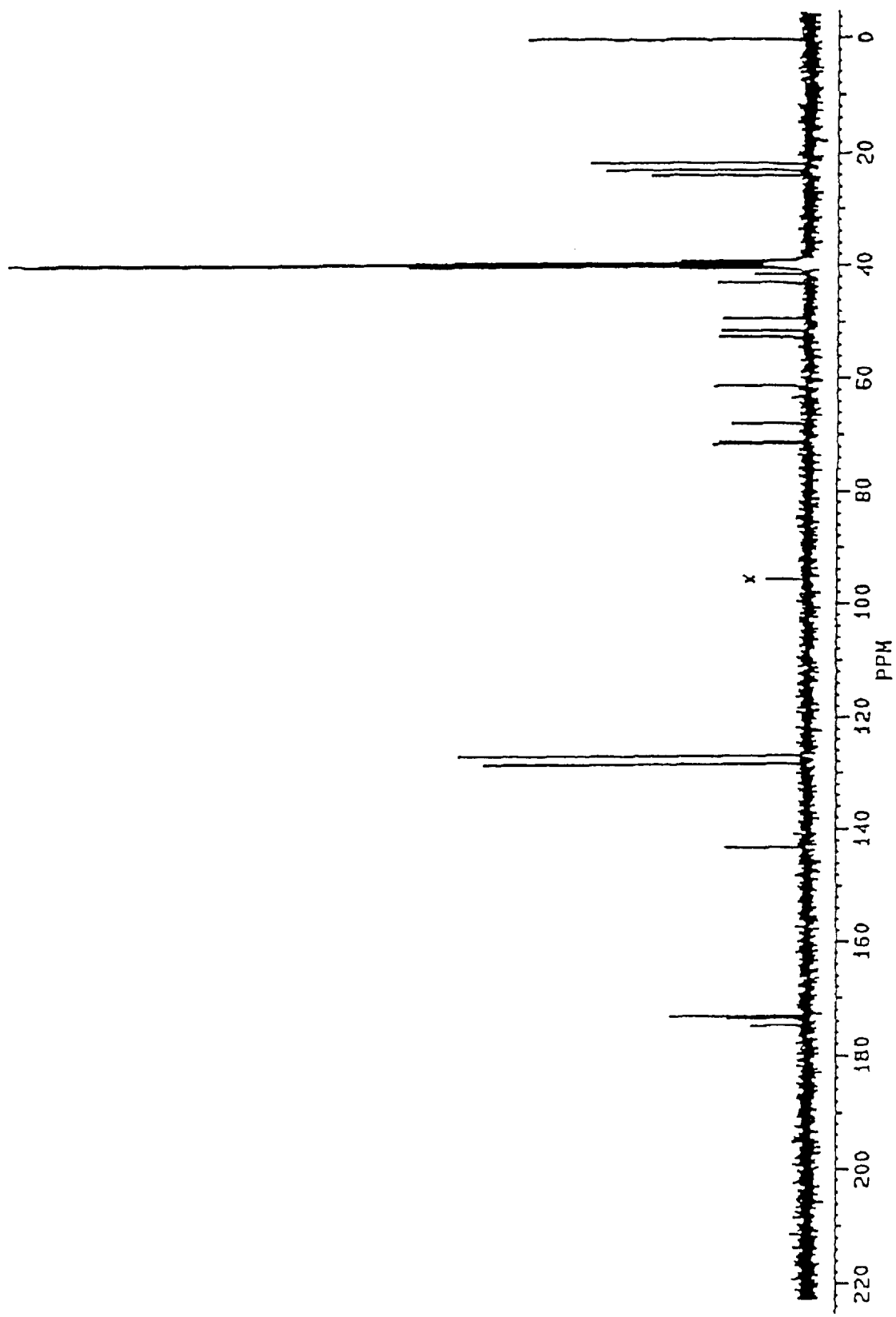
FIG. 3 is a $^{13}$C-NMR spectrum of HC-70III obtained in Example 1.

HC-70III (Compound 3)
1) Appearance: colorless crystals
2) Optical rotation: −67° (c=0.55, 0.1N HCl, 24° C.)
3) Molecular weight: FAB-MS m/z 456 (M+H)$^+$
4) Elemental analysis: (%) (calcd. as containing 1 mol of $H_2O$) Found : C, 53.14; H, 7.14; N, 8.98 Calcd.: C, 53.27; H, 7.45; N, 8.87
5) Molecular formula: $C_{21}H_{33}N_3O_8$
6) UV spectrum: λmax (ε) In water, 257 nm (350)
7) IR spectrum: KBr, dominant absorptions (wave-number, $cm^{-1}$) 3390, 2970, 2930, 1660, 1540, 1400, 1070, 1050, 700
8) $^{13}$C-NMR spectrum: DMSO-$d_6$, chemical shifts (75 MHz, δ ppm; FIG. 3) 174.3, 172.9, 172.4, 142.7, 127.9, 126.5, 71.2, 70.8, 67.6, 60.9, 52.3, 51.2, 49.0, 42.8, 41.3, 23.9, 23.0, 21.7
9) Amino acid analysis: after 24hr of hydrolysis in 6N-HCl at 110° C.) Leucine (1 mol)
10) Color reactions:
Positive: ninhydrin, Greig-Lieback
Negative: Ehrlich, Sakaguchi
11) High-performance liquid chromatography (HPLC):
Column: YMC-Pack ODS-A, A-312, 150×6.0 mm (YMC)
Mobile phase: 15% (v/v) acetonitrile/0.02 M
phosphate buffer (pH 4.5)
Flow rate: 1.0 mL/min.
Detection: UV absorptiometry, 214 nm
Retention time: 6.0 min.
12) Thin-layer chromatography (TLC):
Stationary phase: silica gel $60F_{254}$, 0.25 mm (Merck, Germany)
Developing solvent: n-butanol/acetic acid/water (12:3:5)
Rf: 0.35

The chemical formulas of HC-70I, II, and III are as follows.

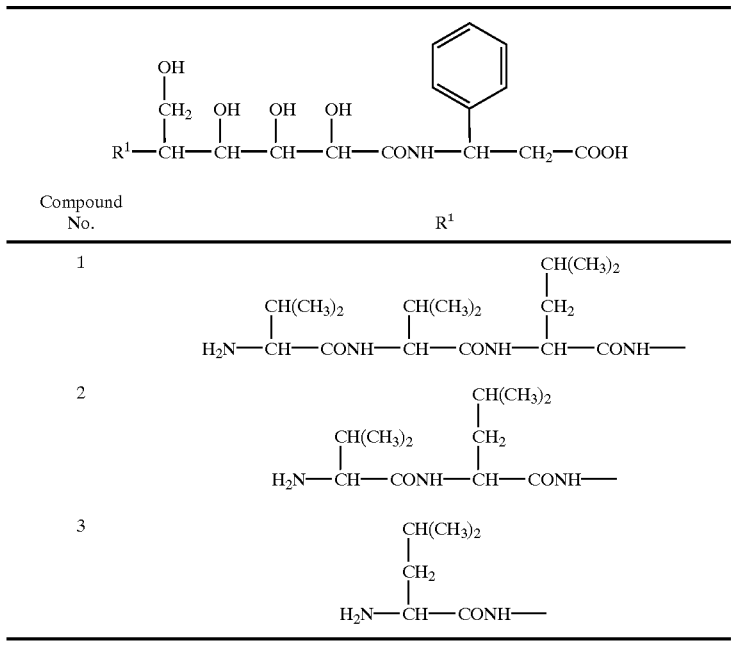

Compound 1 is (S)-3-[(2S,3R,4R,5S)-2,3,4,6-tetrahydroxy-5-(L-valyl-L-valyl-L-leucyl)aminohexanoyl]amino-3-phenylpropionic acid (HC-70I, the compound of Example 2).

Compound 2 is (S)-3-[(2S,3R,4R,5S)-2,3,4,6-tetrahydroxy-5-(L-valyl-L-leucyl)aminohexanoyl]amino-3-phenylpropionic acid (HC-70II, the compound of Example 1). Compound 3 is (S)-3-[(2S,3R,4R,5S)-2,3,4,6-tetrahydroxy-5-(L-leucyl)aminohexanoyl]amino-3-phenylpropionic acid (HC-70III, the compound of the Example 1)

The compound wherein $R^1=NH_2$, or a salt thereof can be produced by causing an enzyme to act upon Compound 1, 2 or 3 or a salt thereof. The enzyme which can be used for this purpose includes but is not limited to exopeptidases (e.g. leucine aminopeptidase) and proteinases [e.g. Actinase E (Kaken Pharmaceutical Co., Ltd.)].

This reaction is generally carried out in water, and for pH control, an inorganic or organic acid, an alkali, or a buffer may be added. The reaction temperature is not particularly restricted unless the enzymatic reaction is hindered but is generally about 10 to 50° C., preferably 20 to 40° C. The reaction time depends upon the kind and amount of enzyme, reaction temperature, and solution pH but is generally several minutes to scores of hours.

The chemical formula of the resulting compound wherein $R^1=NH_2$ (Compound 5) is as follows.

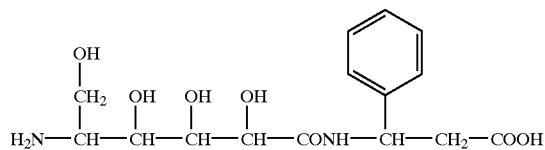

Compound 5 is (S)-3-[(2S,3R,4R,5S)-5-amino-2,3,4,6-tetrahydroxyhexanoyl]amino-3-phenylpropionic acid (the compound of Example 4).

As the compound 5 is produced and accumulated in the fermentation froth of Bacillus sp. HC-70 and *Bacillus insoli-tus* HC-72, it also can be obtained and purified from the fermentation broth according to the same method mentioned above.

The compound of general formula (I) or a salt thereof will hereinafter be referred to sometimes as Compound (I).

The salt of Compound (I) according to the invention includes pharmacologically acceptable base addition salts and acid addition salts. The base addition salts include but are not limited to salts with alkali metals (e.g. sodium, potassium, etc.) and salts with alkaline earth metals (e.g. calcium, magnesium, etc.). The acid addition salts include but are not limited to salts with inorganic acids (e.g. hydrochloric acid, hydrobromic acid, hydroiodic acid, sulfuric acid, phosphoric acid, etc.) and salts with organic acids (e.g. acetic acid, propionic acid, lactic acid, succinic acid, maleic acid, tartaric acid, citric acid, gluconic acid, ascorbic acid, benzoic acid, methanesulfonic acid, p-toluenesulfonic acid, cinnamic acid, fumaric acid, malic acid, oxalic acid, etc.).

The hydrate as well as the anhydride of the compound of general formula (I) also falls within the scope of the invention. The examples of the hydrate are 0.5 hydrate, 1 hydrate, 1.5 hydrate, 2 hydrate, 2.5 hydrate, 3 hydrate, 3.5 hydrate, 4 hydrate and so on.

The compound (I) of the invention can be isolated and purified by per se known procedures such as solvent extraction, pH change, phase transfer or redistribution, crystallization, recrystallization, and chromatography. The starting compound or salt for Compound (I) can also be isolated and purified by the like procedures but the reaction mixture containing it may be directly submitted to the intended reaction.

Where Compound (I) of the invention exists as optical isomers, stereoisomers, position isomers, or rotation isomers, those isomers also fall within the scope of the invention and each of such isomers can be provided as a single substance by the known synthetic technology or fractionating technology. For example, when the compound of the invention occurs as optical isomers, each isomer available upon optical resolution of the compound also falls within the scope of the invention.

The optical isomers can be produced by per se known methods. Specifically, a desired optical isomer can be obtained by using an optically active synthetic intermediate or subjecting the product racemic mixture to optical resolution.

The optical resolution mentioned above can be achieved by per se known techniques such as the fractional recrystallization method, chiral column method, and diastereomer method described hereinafter.

(1) Fractional Recrystallization Method

This method comprises causing a racemic compound to form a salt with an optically active compound, separating it by fractional crystallization, and optionally neutralizing the same to provide the free optical isomer.

(2) Chiral Column Method

This method comprises applying a racemic compound or a salt thereof onto a chiral column. In the case of liquid chromatography, a typical procedure comprises applying a mixture of optical isomers onto a chiral column, for example ENANTIO-OVM (Tosoh Corporation), and carrying out an elution with water, a buffer (e.g. phosphate buffer), or an organic solvent (e.g. ethanol, methanol, acetonitrile, etc.) or a mixture of such solvents to recover the desired optical isomer. In the case of gas chromatography, the necessary fractionation can be achieved using a chiral column such as CP-Chirasil DeXCB (G. L. Science).

(3) Diastereomer Method

This method comprises reacting a racemic mixture with an optically active reagent to prepare a mixture of diastereomers, subjecting the mixture to routine fractionation (e.g. fractional recrystallization, chromatography, etc.) to provide a single substance, and further subjecting it to chemical treatment such as hydrolysis to cleave off the optically active reagent moiety. For example when the compound of the invention has a hydroxyl group or a primary or secondary amino group, the corresponding ester or amide diastereomers can be obtained by subjecting the substrate compound to condensation reaction with an optically active organic acid (e.g. MTPA [α-methoxy-α-(trifluoromethyl)phenylacetic acid], (−)-menthoxyacetic acid, etc.). On the other hand, when the compound of the invention has a carboxyl group, the amide or ester diastereomers can be obtained by subjecting the substrate compound to condensation reaction with an optically active amine or alcohol reagent. The separated diastereomer can then be converted to the optical isomer of the initial compound by acid hydrolysis or basic hydrolysis.

Compound (I) according to the present invention is less toxic and has laudable pharmacobiological activities, for example high antibacterial activity against Helicobacter bacteria represented by *Helicobacter pylori*, so that it is effective in the prevention or treatment of diseases associated with *Helicobactert pylori* infection and/or an ammonium produced by *Helicobacter pylori* (e.g., duodenal ulcer, gastric ulcer, gastritis (inclusive of chronic gastritis), cancer of the stomach, gastric MALT lymphoma, hepatic encephalopathy, diabetes mellitus, urticaria).

Therefore, the medicinal composition comprising Compound (I) according to the invention can be administered as a safe antibacterial agent or as a safe antiulcerative drug to man and other mammals (e.g. canine, feline, monkey, rat, mouse, equine, bovine, etc.), alone or together with a pharmaceutically acceptable carrier, either orally or parenterally. Usually, the oral route of administration is preferred.

The dosage form which can be used for oral medication includes but is not limited to tablets (inclusive of dragees and film-coated tablets), pills, granules, fine granules, powders, capsules (inclusive of soft capsules), syrup, emulsion, and suspension. The dosage form for parenteral administration includes but is not limited to injections, infusions, drip infusions, and suppositories.

The gastric mucosa-adhesive composition according to the present invention is, for instance, a composition comprising (a) a compound (I) of the present invention as an active ingredient having such as anti-*Helicobacter pylori* activity, (b) a lipid and/or a polyglycerol fatty acid ester and (c) a viscogenic agent (a material which becomes sufficiently viscous with water to attach itself to the gastric mucosa). The composition is at least adapted to attach itself to the gastric mucosa and/or otherwise stay in the stomach and release the active ingredient such as anti-*Helicobacter pylori* substance contained therein at a suitable rate and thereby display a potentiated pharmaceutical effect (e.g. anti-*Helicobacter pylori* action).

An example of the above-mentioned gastric mucosa adhesive composition would be a composition comprising (a) an anti-*Helicobacter pylori* substance, (b) a lipid and/or a polyglycerol fatty acid ester and (c) a viscogenic agent capable of being viscous with water, and preferably be a composition further comprising (d) a material which swells a viscogenic agent (e.g. a curdlan and/or a low-substituted hydroxypropylcellulose as a swelling material). Though there is no particular limitation on its dosage form, the composition is preferably a solid composition and particularly a composition containing a matrix. The matrix may, for example, be a gastric mucosa-adhesive matrix comprising (a), (b) a polyglycerol fatty acid ester and (c), or a gastric mucosa-adhesive matrix comprising (a), (b) a lipid and (c). The preferred matrix is a gastric mucosa-adhesive matrix comprising (b) a polyglycerol fatty acid ester. The preferable example of the gastric adhesive composition of the present invention is a composition further comprising (d) a material which swells a viscogenic agent.

The gastric mucosa-adhesive matrix comprising said four components (a), (b), (c), and/or (d) is preferably, a matrix such that the viscogenic agent is dispersed in the matrix which comprises the polyglycerol fatty acid ester or lipid or a matrix which is covered with the viscogenic agent. The melting point of the gastric mucosa-adhesive matrix may, for example, be about 30° to about 120° C. and preferably about 40° to about 120° C.

The polyglycerol fatty acid ester for use in the present invention is esters of polyglycerols with fatty acids and may be a mono- to polyester (diester, triester, etc.). The polyglycerol fatty acid ester is characterized in that it does not undergo polymorphic transition or any material interaction with the active ingredient, allowing those coexisting ingredients to remain undeactivated and stable for an extended period of time.

Polyglycerol by definition is "a polyhydric alcohol containing n (cyclic form) to (n+2) (straight-chain form or branched form) hydroxyl groups and (n-1) (straight-chain form or branched form) to n (cyclic) ether bonds per molecule" [Polyglycerin Esters, (ed.) Sakamoto Yakuhin Kogyo Co., Ltd., published Oct. 4, 1994], and any straight-chain ester or branched-chain ester can be used in the present invention.

For example, compounds of the following formula (I) can be employed.

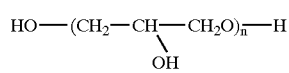

(wherein n represents a degree of polymerization which is an integer of not less than 2). The value of n is generally about 2 to about 50, preferably about 2 to about 20, and for still better results, about 2 to about 10.

The polyglycerol includes but is not limited to diglycerol, triglycerol, tetraglycerol, pentaglycerol, hexaglycerol, heptaglycerol, octaglycerol, nonaglycerol, decaglycerol, pentadecaglycerol, eicosaglycerol, and triacontaglycerol. Among those polyglycerols, tetraglycerol, hexaglycerol or decaglycerol is used in many cases.

The fatty acid includes but is not limited to saturated or unsaturated fatty acids each containing about 8 to about 40, preferably about 12 to about 25, and more preferably about 15 to about 22 carbon atoms. The preferred fatty acid is stearic acid, oleic acid, lauric acid, linoleic acid, linolenic acid, ricinoleic acid, caprylic acid, capric acid, orbehenic acid.

The polyglycerol fatty acid ester includes but is not limited to behenic acid hexa(tetra)glyceride, caprylic acid mono(deca)glyceride, caprylic acid di(tri)glyceride, capric acid di(tri)glyceride, lauric acid mono(tetra)glyceride, lauric acid mono(hexa)glyceride, lauric acid mono(deca)glyceride, oleic acid mono(tetra)glyceride, oleic acid mono(hexa)glyceride, oleic acid mono(deca)glyceride, oleic acid di(tri)glyceride, oleic acid di(tetra)glyceride, oleic acid sesqui(deca)glyceride, oleic acid penta(tetra)glyceride, oleic acid penta(hexa)glyceride, oleic acid deca(deca)glyceride, linoleic acid mono(hepta)glyceride, linoleic acid di(tri)glyceride, linoleic acid di(tri)qlyceride, linoleic acid di(tetra)glyceride, linoleic acid di(hexa)glyceride, stearic acid mono(di)glyceride, stearic acid mono(tetra)glyceride, stearic acid penta(tetra)glyceride, stearic acid mono(deca)glyceride, stearic acid tri(tetra)glyceride, stearic acid penta(hexa)glyceride, stearic acid tri(hexa)glyceride, stearic acid deca(deca)glyceride, palmitic acid mono(tetra)glyceride, palmitic acid mono(hexa)glyceride, palmitic acid mono(deca)glyceride, palmitic acid tri(tetra)glyceride, palmitic acid tri(hexa)glyceride, palmitic acid sesqui(hexa)glyceride, palmitic acid penta(tetra)glyceride, palmitic acid penta(hexa)glyceride, palmitic acid deca(deca)glyceride, and polyglycerol polyricinolate (e.g. tetraglycerol polyricinolate, etc.).

The preferred polyglycerol fatty acid ester includes, for instance, behenic acid hexa(tetra)glyceride (e.g. HB-310™, Sakamoto Yakuhin Kogyo Co., Ltd.,; Poem J-46B™, Riken Vitamin Co.), stearic acid penta(tetra)glyceride (e.g. PS-$_{310}$™. Sakamoto Yakuhin Kogyo Co., Ltd.), stearic acid mono(tetra)glyceride (e.g. MS-310™, Sakamoto Yakuhin Kogyo Co., Ltd.), stearic acid penta(hexa)glyceride (e.g. PS-500™, Sakamoto Yakuhin Kogyo Co., Ltd.), stearic acid mono(deca)glyceride, polyglycerol polyricinolate (e.g. tetraglycerol polyricinolate, etc.) (e.g. CRS-75™, Sakamoto Yakuhin Co., Ltd.) and mixtures of such glycerides.

Those polyglycerol fatty acid esters can be used each alone or as a mixture of two or more species, preferably about 2 or about 3 species.

The molecular weight of the polyglycerol fatty acid ester is generally about 200 to about 5000, preferably about 300 to about 3000, preferably about 2000 to about 3000. The hydrophile-lipophile balance (HLB) number of the polyglycerol fatty acid ester is generally about 1 to about 22, preferably about 1 to about 15, more preferably about 1 to about 9, for still better results, about 1 to about 4. Two or more polyglycerol fatty acid esters differing in HLB number from each other may be used in combination to provide for the designed HLB number. By adjusting the HLB of the polyglycerol fatty acid ester judiciously, the release and dissolution kinetics of the active drug substance can be controlled as desired.

The proper polyglycerol fatty acid ester can be selected with reference to the particular active ingredient (e.g. anti-*Helicobacter pylori* agent, etc.), viscogenic agent, swelling material (e.g. curdlan, and/or low-substituted hydroxypropylcellulose, etc.), the particular combination thereof, and the objective form of the composition. Preferably, however, compounds which are solid at atmospheric temperature (ca 15° C.) are employed. The melting point of the polyglycerol fatty acid ester may, for example, be about 15 to about 80° C., preferably about 30 to about 75° C., and for still better results, about 45 to about 75° C.

A suitable polyglycerol fatty acid ester is selected according to the species of active ingredient used and the intended dosage form. Generally, polyglycerols with degrees of polymerization in the range of about 2 to about 16 are preferred. The particularly preferred range is about 2 to about 10. Preferred are esters such that the fatty acid has formed an ester bond with at least one of the (degree of polymerization +2) hydroxyl groups, preferably such that the fatty acid or acids have formed ester bonds with not less than about 60%, more preferably not less than about 80%, of the total number of hydroxyl groups in the polyglycerol. The fatty acid or acids are preferably saturated acids each containing about 6 to about 22, more preferably about 15 to about 25, and for still better result, about 18 to about 22 carbon, atoms. The fatty acid involved in the formation of the ester bonds may be of the same kind or different kinds.

In the production of a solid composition according to the present invention by using two or more different polyglycerol fatty acid esters as a mixture, a liquid polyglycerin fatty acid ester may be included in the mixture as long as the final composition is solid at atmospheric temperature.

When the polyglycerol fatty acid ester is used as a gastric mucosa-adhesive matrix, the amount of the polyglycerol fatty acid ester relative to the total weight of the composition is generally about 5 to about 98 weight %, preferably about 20 to about 95%, more preferably about 40 to about 95% and to the active ingredient in the composition may, for example, be about 0.01 to about 15000 times by weight, preferably about 0.1 to about 1000 times by weight, and for still better result, about 0.1 to about 100 times by weight.

The lipid for use in the present invention is one having a melting point of about 40 to about 120° C., preferably about 40 to about 90° C.

The lipid includes but is not limited to saturated fatty acids of about 14 to about 22 carbon atoms (e.g. myristic acid, stearic acid, palmitic acid, behenic acid, etc.) or salts (sodium salt, potassium salt, etc.) thereof; higher alcohols of about 16 to about 22 carbon atoms (e.g. cetyl alcohol, stearyl alcohol, etc.); fatty acid glycerol esters such as the monoglycerides, diglycerides, triglycerides, etc. of the above-mentioned fatty acids (e.g. 1-monostearin, 1-monopalmitin, etc.); oils (e.g. castor oil, cottonseed oil, beef tallow, etc., inclusive of the corresponding hydrogenated oils); waxes (e.g. beeswax, carnauba wax, sperm wax, etc.); hydrocarbons (e.g. paraffin, microcrystalline wax, etc.); and phospholipids (e.g. hydrogenated lecithin etc.). Among those lipids, oils, waxes, $C_{14-22}$ saturated fatty acids, $C_{16-22}$ higher alcohols, and hydrocarbons are preferred. The more preferred are hydrogenated cottonseed oil, hydrogenated castor oil, hydrogenated soybean oil, carnauba wax, stearic acid, stearyl alcohol, and microcrystalline wax. The most preferred is hydrogenated castor oil or carnauba wax.

When a lipid is used as the gastric mucosa-adhesive matrix, the amount of the lipid relative to the total weight of the composition is generally about 5 to about 98 weight %, preferably about 20 to about 95 weight %, more preferably about 40 to about 95 weight %, and to the active ingredient in the composition is about 0.01 to about 15000 times by weight, preferably about 0.1 to about 1000 times by weight, and for still better result, about 0.1 to about 100 times by weight.

The above-mentioned polyglycerol fatty acid ester and lipid may be used as a mixture. For example, the combination of a polyglycerol fatty acid ester with a wax or the combination of a polyglycerol fatty acid ester with a hydrogenated oil can be mentioned. Specifically, a mixture of 2, 3 or more members selected from among behenic acid hexa(tetra)glyceride, stearic acid penta(tetra)glyceride, stearic acid penta(hexa)glyceride, polyglycerol polyricinolate (e.g. tetraglycerol polyricinolate, etc.), carnauba wax, hydrogenated castor oil, and microcrystalline wax, can be mentioned.

When the gastric mucosa-adhesive matrix comprising a viscogenic agent in addition to said polyglycerol fatty acid ester and/or lipid is used for the composition of the invention, the total amount of the polyglycerol fatty acid ester and lipid relative to the total weight of the composition is generally about 5 to about 98 weight %, preferably about 20 to about 95 weight %, more preferably about 40 to about 95 weight %, and to the active ingredient in the composition is about 0.01 to about 15000 times by weight, preferably about 0.1 to about 1000 times by weight, and for still better result, about 0.1 to about 100 times by weight.

A lipid may be incorporated in a matrix comprising the polyglycerol fatty acid ester. The lipid is a pharmaceutically acceptable water-insoluble substance capable of regulating the dissolution kinetics of the active ingredient. The lipid includes those species mentioned hereinbefore.

When a lipid and a polyglycerol fatty acid ester are used in combination, the amounts of the lipid and polyglycerol fatty acid ester need only be within the range not detracting from the adhesion to the gastrointestinal mucosa and can be selected from-said range of total amount, and the amount of the lipid relative to the pplyglycerol fatty acid ester may be about 0.01 to about 1000 times by weight, preferably about 0.1 to about 200 times by weight, and for still better results, about 0.1 to about 100 times by weight.

The swelling material used in the present invention is a material which swells a viscogenic agent or accelerates the swell of a viscogenic agent caused by water.

Any type of swelling material can be used in the present invention as long as it has the characteristics described above and is pharmaceutically acceptable. For instance, preferably a curdlan and/or a low-substituted hydroxypropylcellulose can be used.

The amount of the swelling material in the gastric mucosa-adhesive composition of the present invention is about 0.5 to about 50 weight %, preferably about 1 to about 40 weight %, and for still better results, about 1 to about 30 weight %, relative to the total weight of the composition.

The curdlan for use in the present invention is a linear water-insoluble polysaccharide (β-1,3-glucan) produced by microorganisms (such as *Alcaligenes faecalis var. myxogenes* etc.), which includes such species as curdlan 10C3K, 13140, 12607, 12665, 13127, 13256, 13259, and 13660 [New Food Industry, 20, No. 10, p. 49 (1978)]. Among those and other species of curdlan, those which are acceptable as pharmaceutical bases or excipients can be employed. A preferred example is curdlan N (a food additive).

The amount of the curdlan in the gastric mucosa-adhesive composition of the invention relative to the total weight of the composition is about 0.5 to about 50 weight %, preferably about 1 to about 40 weight %, and more preferably about 1 to about 30 weight %.

The low-substituted hydroxypropylcellulose for use in the present invention is a cellulose derivative available upon substitution of hydroxypropoxy for some of the hydroxy groups of cellulose, which has a hydroxypropoxy content of 5.0 to 16.0% (as specified in the Japanese Pharmacopoeia Twelfth Edition-). The low-substituted hydroxypropyl cellulose mentioned above is useful, in particular, one which has a hydroxypropoxy content of 7.0 to 13.0% (e.g. L-HPC™, Shin-Etsu Chemicals., Co., Ltd. is preferred. Thus, those derivatives with a degree of substitution within the above range and varying in particle diameter, such as LH-11™ (Shin-Etsu Chemicals., Co., Ltd.) hydroxypropoxy content 10.0 to 12.9%, particle size distribution $\geq 98\%$ under 150 $\mu$m sieve and $\leq 0.5\%$ on 180 $\mu$m sieve), LH-20™ (Shin-Etsu Chemicals., Co., Ltd., hydroxypropoxyl content 13.0–16.0%, particle size distribution $\geq 90\%$ under 75 $\mu$m sieve and $\leq 1.0\%$ on 106 $\mu$m sieve), LH-21 (Shin-Etsu Chemicals., Co., Ltd., hydroxypropoxyl content 10.0 to 12.9%, particle size distribution $\geq 90\%$ under 75$\mu$m sieve and $\leq 1.0\%$ on 106 $\mu$m sieve), LH-22 (Shin-Etsu Chemicals., Co., Ltd., hydroxypropoxyl content 7.0 to 9.9%, particle size distribution $\geq 90\%$ under 75 $\mu$m sieve and $\leq 1.0\%$ on 106 $\mu$m sieve), and LH-31 (Shin-Etsu Chemicals., Co., Ltd., hydroxypropoxyl content 10.0 to 12.9%, mean particle diameter not greater than 30 $\mu$m, particle size distribution $\geq 50\%$ under 45 $\mu$m sieve and $\leq 5.0\%$ on 75 $\mu$m sieve), among others, can be utilized.

Preferably, LH-22 or LH-31 are utilized.

The amount of the low-substituted hydroxypropylcellulose in the gastric mucosa adhesive composition of the present invention is about 0.5 to about 50 weight %, preferably about 1 to about 40 weight %, and for still better results, about 1 to about 30 weight %, relative to the total weight of the composition.

Any type of viscogenic agent can be used in the present invention as long as it becomes sufficiently viscous with water to attach itself to the gastrointestinal mucosa and is pharmaceutically acceptable. Preferred, however, are those substances which are markedly swollen by water and develop high degrees of viscosity. The viscogenic agent, thus, includes synthetic polymers and naturally-occurring viscogenic materials.

The preferred synthetic polymer is a polymer such that the viscosity of a 2% aqueous solution thereof at 20° C. is about 3 to about 50000 cps., preferably about 10 to about 30000 cps., and for still better results, about 15 to about 30000 cps. However, when a basic or an acidic polymer which gains in viscosity on neutralization is used, the preferred polymer is such that the viscosity of a 0.2% solution thereof after neutralization at 20° C. is about 100 to about 500000 cps, preferably about 100 to about 200000 cps, and for still better results, about 1500 to about 100000 cps.

The value of the viscosity is measured with a Brookfield viscometer at about 20° C.

Preferably the above-mentioned polymer is an acidic polymer which includes but is not limited to carboxyl- or sulfo-containing polymers and the corresponding salt-containing polymers. Particularly preferred are carboxyl-containing polymers and carboxylate salt-containing polymers.

The carboxyl (inclusive of its salt)-containing polymer is preferably an acrylic homopolymer or copolymer containing acrylic acid as a monomer unit or a salt thereof. The salt includes monovalent metal salts such as the sodium salt, potassium salt, etc. and divalent metal salts such as the magnesium salt, calcium salt, ammonium salt, etc.

The acrylic polymer, inclusive of its salt, includes polymers containing carboxyl groups in a proportion of about 58 to about 63 weight % and having a molecular weight of about $20 \times 10^4$ to about $600 \times 10^4$, preferably about $100 \times 10^4$ to about $600 \times 10^4$, and more preferably about $100 \times 10^4$ to about $500 \times 10^4$. The preferred acrylic polymer, inclusive of its salt, includes acrylic acid homopolymers and their salts. Such polymers are listed under the heading of carboxyvinyl polymer in Japanese Standards of Pharmaceutical Ingredients (October 1986).

As specific examples of said acrylic polymer, there can be mentioned carbomer [Carbopol™ (hereinafter referred to as Carbopol), The B. F. Goodrich Company] 940, 934, 934P, 941, 1342, 974P, 971P (NF XVIII), EX214 etc., HIVISWAKO™ 103, 104, 105, and 204 (Wako Pure Chemical Industries), NOVEON AA1™ (The B. F. Goodrich Company), and calcium polycarbophil (USP XXIII)).

The naturally-occurring viscogenic agent includes but is not limited to mucin, agar, gelatin, pectin, carrageenin, sodium alginate, locust bean gum, xanthan gum, tragacanth gum, chitosan, pullulan, waxy starch, sucralfate, curdlan, and cellulose and its derivatives (cellulose sulfate and preferably hydroxypropylcellulose or hydroxypropylmethylcellulose).

The most preferred viscogenic agent is an acrylic polymer or its salt.

Those viscogenic agents can be used alone or in combination.

Referring to the amount of the viscogenic agent for use in the composition of the invention, its amount in the gastric mucosa adhesive matrix may for example be about 0.005 to about 99 weight %, preferably about 0.5 to about 45 weight %, more preferably about 1 to about 30 weight%, furthermore preferably about 1 to about 25 weight %, and for still better result, about 1 to about 20 weight %. When, for example, the viscogenic agent is dispersed in a matrix comprising the polyglycerol fatty acid ester and/or lipid, the amount of the viscogenic agent is about 0.005 to about 95 weight %, preferably about 0.5 to about 30 weight %, and more preferably about 1 to about 25 weight %, and for still better result, about 1 to about 20 weight % based on the total weight. When the matrix is coated with the viscogenic agent, the proportion of the viscogenic agent is also about 0.005 to about 95 weight %, preferably about 0.5 to about 30 weight %, and more preferably about 1 to about 25 weight %, and for still better result, about 1 to about 20 weight based on the total weight.

When the composition of the present invention contains a curdlan as a swelling material, the composition is capable of attaching itself to the gastrointestinal mucosa even without addition of said viscogenic agent, for the curdlan acts as a viscogenic agent by itself. In this case, the curdlan may be formulated in an amount beyond the range defined hereinbefore for imparting the necessary adherent effect.

The gastric mucosa adhesive composition comprising the viscogenic agent dispersed in a matrix comprising a polyglycerol fatty acid ester and/or lipid may be any dispersion of the polyglycerol fatty acid ester and/or lipid, viscogenic agent, curdlan and/or low-substituted hydroxypropylcellulose, and active ingredient. Dispersion can be effected by the analogue to the per se known technology.

The amount of Compound (I) in the medicinal composition of the invention is generally 2 to 85 weight % and preferably 5 to 70 weight %.

The manufacturing technology for the pharmaceutical composition comprising the compound (I) of the present invention include those known methods which are in common usage in the pharmaceutical field. Moreover, the composition can be manufactured using suitable amounts of the excipient, binder, disintegrator, lubricant, sweetener, surfactant, suspending agent, emulsifier, etc. which are generally used in the pharmaceutical industry.

For the manufacture of tablets containing Compound (I), for instance, said excipient, binder, disintegrator, and lubricant are employed. For the manufacture of pills or granules, the excipient, binder, and disintegrator are formulated. The excipient is also used in the manufacture of powders or capsules, while the sweetener is added in the manufacture of a syrup. In the manufacture of an emulsion or a suspension, the suspending agent, surfactant, and/or emulsifier is added. The excipient includes but is not limited to lactose, sucrose, glucose, starch, cane sugar, microcrystalline cellulose, licorice powder, mannitol, sodium hydrogencarbonate, calcium phosphate, and calcium sulfate. The binder includes but is not limited to 5 to 10 wt. % starch solution, 10 to 20 wt. % gum arabic solution or gelatin solution, 1 to 5 wt. % gum tragacanth solution, carboxymethylcellulose solution, sodium alginate solution, and glycerin. The disintegrator includes but is not limited to starch and calcium carbonate. The lubricant includes but is not limited to magnesium stearate, stearic acid, calcium stearate, and purified talc. The sweetener includes but is not limited to glucose, fructose, inverted sugar, sorbitol, xylitol, glycerin, and simple syrup. The surfactant includes but is not limited to sodium lauryl sulfate, polysorbate 80, sorbitan fatty acid monoesters, and polyoxyl stearate 40. The suspending agent includes but is not limited to gum arabic, sodium alginate, carboxymethylcellulose sodium, methylcellulose, and bentonite. The emulsifier includes but is not limited to gum arabic, gum tragacanth, gelatin, and polysorbate 80. Aside from the above, the colorant, preservative, flavorant, corrigent, stabilizer, thickener, and other common additives for pharmaceutical use can be formulated in suitable amounts in the manufacture of said dosage forms containing Compound (I).

The example of the technology for production of a gastric mucosa adhesive composition of the present invention is now described.

1) The gastric mucosa adhesive composition, which is solid at atmospheric temperature, can be produced in a similar manner to the per se known technology. A typical process comprises melting the polyglycerol fatty acid ester and/or lipid at a temperature beyond its melting point, adding said viscogenic agent, anti-*Helicobacter pylori* agent, and curdlan and/or low-substituted hydroxypropylcellulose either at one time or serially to the melt to thereby disperse them in the melt, and cooling the dispersion. The heating temperature may for example be about 40 to about 150° C., preferably about 50 to about 110° C., and more preferably about 50 to about 100° C. This process can be carried out with a conventional granulating machine and the composition is preferably molded into solid beads (e.g. granules, fine granules, etc.) by spray cooling, for example spray chilling.

The spray chilling method may typically comprise dripping a mixed dispersion of the viscogenic agent, curdlan and/or low-substituted hydroxypropylcellulose, and active ingredient in a molten polyglycerol fatty acid ester and/or lipid at a constant flow rate onto a rotary disk revolving at a high speed of, for example, about 10 to about 6000 rpm, preferably about 900 to about 6000 rpm, and more preferably about 1000 to about 5000 rpm. The rotary disk may for example be a flat, smooth disk, typically made of aluminum and measuring about 5 to about 100 cm in diameter, preferably about 10 to about 20 cm in diameter. The dripping rate of said molten dispersion can be selected according to the designed particle diameter and is generally about 1 to about 1000 g/min., preferably about 2 to about 200 g/min., more preferably about 5 to about 100 g/min. The granules thus obtained are true to spheres so that a uniform film can be formed on their surface with good efficiency in the subsequent coating step.

An alternative production process comprises kneading the viscogenic agent, curdlan and/or low-substituted hydroxypropylcellulose, and active ingredient into the polyglycerol fatty acid ester and/or lipid and granulating the resulting dispersion. The solvent for use in this process may be a solvent of the common variety (e.g. methanol, acetonitrile, chloroform, etc.).

A further alternative process for producing the solid composition comprises the use of the melt granulation technology. A typical melt granulation process comprises heating the polyglycerol fatty acid ester and/or lipid at a temperature near its melting point, for example, a temperature from its melting point to a temperature about 5° C. below the melting point, subjecting the resulting melt to granulation, such as the above-mentioned spray chilling, and suspending the resulting fine particles together with the viscogenic agent, anti-*Helicobacter pylori* agent, and curdlan and/or low-substituted hydroxypropylcellulose under heating at a suitable temperature to provide an adhesive matrix-drug system. In this case, the influence of heat on the active ingredient can be avoided.

The solid composition comprising a matrix made up of a polyglycerol fatty acid ester and/or a lipid and coated with a viscogenic agent may be a preparation coated with such a viscogenic agent alone or a mixture of a viscogenic agent and a swelling material (e.g. curdlan and/or a low-substituted hydroxypropylcellulose etc), preferably with a coating material containing either a viscogenic agent alone or a viscogenic agent plus a curdlan and/or a low-substituted hydroxypropylcellulose. The coating material may be a composition containing at least one member selected from among said polyglycerol fatty acid ester, said lipid, and said water-insoluble polymer. When a viscogenic agent which is sparingly compatible or incompatible with the components of the solid composition is employed for coating, the solid composition can be provided with a film in which the viscogenic agent has been dispersed. The coating material may further contain the additives mentioned hereinbefore.

The water-insoluble (hydrophobic) polymer includes but is not limited to hydroxypropylmethylcellulose phthalate (The Japanese Pharmacopoeia Twelfth Edition), hydroxypropylmethylcellulose acetate succinate (Shin-Etsu Chemicals Co., Ltd.), carboxymethylethylcellulose (Freund Industries Co., Ltd., CMEC, Japanese Standards of Pharmaceutical Ingredients, 1986), cellulose acetate trimellitate (Eastman), cellulose acetate phthalate (The Japanese Pharmacopoeia Twelfth Edition), ethylcellulose (Asahi Chemical Industry Co., Ltd.), aminoalkyl methacrylate copolymer (Röhm-Pharma, Eudragit™ RS-100, RL-100, RL-PO, RS-PO, RS-30D, RL-30D), methacrylic acid-ethyl acrylate copolymer (Röhm-Pharma, Eudragit™ L100-55), methacrylic acid-methyl methacrylate copolymer (Röhm-Pharma, Eudragit™ L-100, S-100), Eudragit™ L30D-55, Eudragit™ NE-30D (Röhm-Pharma), and polyvinyl acetate (Colorcon).

Those hydrophobic polymers can be used independently or as a mixture of two or more different polymers.

The proportion of the viscogenic agent in the coating material is about 0.005 to about 100 weight %, preferably about 0.05 to about 95 weight %, more preferably about 0.05 to about 30 weight %, and for still better result, about 1 to about 10 weight % based on the whole solid fraction of the coating material.

When at least one of the polyglycerol fatty acid ester, lipid, and hydrophobic polymer is used in combination with the viscogenic agent for the coating material, the proportion of the viscogenic agent based on the total weight of the solid fraction of the coating material is about 0.05 to about 95 weight %, preferably about 0.5 to about 95 weight %, more preferably about 0.5 to about 30 weight %, futhermore preferably about 5 to about 30 weight %, and for still better result, about 5 to about 25 weight %.

Referring further to the coating material, two or more members selected from the class consisting of the polyglycerol fatty acid ester, lipid, and hydrophobic polymer can be used in combination. In this case, based on each part by weight of the whole polyglycerol fatty acid ester and/or lipid, the remaining component is used in a proportion of about 0.0001 to about 1000 part by weight, preferably about 0.01 to about 100 part by weight, and more preferably about 0.01 to about 10 part by weight.

The coating amount can be selected according to the type of solid composition and the desired strength of adhesion to the mucosa. For example, the coating amount for a solid composition may be about 0.1 to about 30 weight %, preferably about 0.5 to about 20 weight %, for tablets and about 0.1 to about 100 weight %, preferably about 1 to about 50 weight %, for fine granules.

Where necessary, the coating material may be supplemented with the common additives such as those mentioned hereinbefore. For example, the coating material and the additive may be added together or separately, etc. applied. The proportion of the additive relative to the solid fraction of the coating material is about 0.1 to about 70 weight %, preferably about 1 to about 50 weight %, and more preferably about 20 to about 50 weight %.

The coating technology that can be used includes a variety of per se known methods, such as pan coating, fluidized-bed coating, roll coating, and so on. When the coating material is a solution or dispersion containing water or an organic solvent, the spray coating method can also be employed. There is no particular limitation on the kind of said water or organic solvent. Thus, for example, alcohols such as methanol, ethanol, isopropyl alcohol, etc.; ketones such as acetone etc.; and halogenated hydrocarbons such as chloroform, dichloromethane, trichloromethane, etc. can be used.

When the polyglycerol fatty acid ester and/or lipid is used for coating, the objective coated composition can be produced by melting the polyglycerol fatty acid ester and/or lipid, optionally together with other additives, under heating, emulsifying the melt with water, spray-coating the surface of a solid composition with the resulting emulsion, and drying the coat. An alternative procedure comprises adding the coating material to the solid composition preheated in a coating pan or the like and melt-spreading the coating.

The solid composition is coated generally at a temperature of about 25 to about 60° C. and preferably at about 25 to about 40° C.

The coating time can be judiciously selected with reference to the coating method, the characteristics and amount of the coating material, and characteristics of the substrate solid composition.

Insofar as a sufficient adhesion to the gastrointestinal mucosa can be assured, the gastric mucosa adhesive solid composition may, if necessary, be further coated with a conventional gastric coating agent or a water-soluble coating agent.

The gastric mucosa adhesive composition according to the present invention can generally be administered orally as it is or in a suitable preparation. The solid oral dosage form includes but is not limited to fine granules, granules, pills, tablets manufactured by compressing said fine granules or granules with a tablet machine, and capsules manufactured by filling said fine granules or granules into suitable capsule shells. Among those preparations, fine granules and granules are preferred.

The particle size distribution of said fine granules may for example be: particles measuring about 10 to about 500 μm in diameter account for not less than about 75 weight %, particles larger than about 500 μm account for not more than about 5 weight %, and particles smaller than about 10 μm account for not more than about 10 weight %. The preferred distribution is about 105 to about 500 μm accounting for about ≧75 weight %, about ≧500 μm accounting for not more than about 5 weight %, and about ≦74 μm accounting for not more than about 10 weight %. The particle size distribution of said granules may for example be about 500 to about 1410 μm accounting for not less than about 90 weight % and about ≦177 μm accounting for not more than about 5 weight %.

2) When the gastric mucosa adhesive composition is to be provided as a liquid composition, such a liquid composition can be manufactured by the manner similar to the per se known technology. A typical procedure comprises mixing a polyglycerol fatty acid ester and/or a lipid, which is liquid at atmospheric temperature, a viscogenic agent, a active ingredient, and a swelling material (e.g. a curdlan and/or a low-substituted hydroxypropylcellulose etc.) all at once or serially to provide a dispersion or solution.

The dosage form comprising such a liquid adherent mucosal medication system includes but is not limited to syrups, emulsions, suspensions, and encapsulated versions thereof.

The proportion of the active ingredient (e.g. an anti-HP agent etc.) in the composition of the invention is about 0.005 to about 95 weight %, preferably about 1 to about 95 weight %, and more preferably about 10 to about 95 weight %, and for still better result, about 10 to about 50.

The medicinal composition (especially, a gastric mucosa adhesive composition) of the present invention comprising Compound (I) or a salt thereof is stable and less toxic and can therefore be used safely. The daily oral dosage, which depends on the patient's clinical status and body weight, the particular species of compound, and the route of administration, for an adult patient (b. w. ca 60 kg), for example, with gastric ulcer associated with *Helicobacter pylori* infection is 1 to 500 mg, preferably about 10 to 200 mg, as the active ingredient (Compound (I) or its salt).

In the medicinal composition of the present invention, Compound (I) may occur in combination with one or more other antibacterial or/and antiulcerative agent.

The other antibacterial agent which can thus be concomitantly contained includes but is not limited to nitroimidazoles (e.g. tinidazole and metronidazole), tetracyclines (e.g. tetracycline, doxycycline, and minocycline), penicillins (e.g. amoxicillin, ampicillin, and mezlocillin), cephalosporins (e.g. cefaclor, cefadroxil, cefazolin, cefuroxime, cefuroxime axetil, cephalexin, cefpodoxime proxetil, ceftazidime and ceftriaxone), carbapenems (e.g. imipenem and meropenem), aminoglycosides (e.g. paromomycin), macrolides (e.g. erythromycin, clarithromycin, and azithromycin), lincosamides (e.g. clindamycin), rifamycins (e.g. rifampicillin), and nitrofurantoin. As the antiulceratives which can be used in combination with Compound (I), there can be mentioned gastric proton pump inhibitors (e.g. lansoprazole and omeprazole, pantoprazole, rabeprazole, lemiprazole) and $H_2$ receptor antagonists (e.g. ranitidine, cimetidine, and famotidine).

The above other antibacterial and/or antiulcerative agents can be used in combinations of two or more species. In such a combined drug therapy, the daily oral dosage of said other antibacterial agent or agents per adult human is 1 to 500 mg, preferably 5 to 200 mg, and the daily oral dosage of said other antiulcerative agent or agents per adult human is 0.5 to 1000 mg, preferably 1 to 500 mg.

BEST MODE FOR CARRYING OUT THE INVENTION

The following examples, experimental examples, and formulation examples are only intended to illustrate the present invention in further detail and should by no means be construed as defining the scope of the invention. In those examples, percent (%) means weight/volume percent unless otherwise indicated. The mixing ratio of solvents is a volumetric ratio unless otherwise specified. The NMR spectra were those recorded using Bruker AC-300 Spectrometer or Varian gemini 200 Spectrometer.

EXAMPLE 1

(S)-3-[(2S,3R,4R,5S)-2,3,4,6-tetrahydroxy-5-(L-valyl-L-leucyl)aminohexanoyl]amino-3-phenylpropionic acid (HC-70II, compound 2) and (S)-3-[(2S,3R,4R,5S)-2,3,4,6-tetrahydroxy-5-(L-leucyl)aminohexanoyl]amino-3-phenylpropionic acid (HC-70III, compound 3)

A loopful of Bacillus sp. HC-70 sufficiently grown on a slant medium composed of glucose 0.1%, tryptone 0.5%, yeast extract 0.25%, and agar 1.5% was used to inoculate a 2-L Sakaguchi flask containing 500 mL of a seed culture medium (pH 7.0) composed of glucose 2.0%, soluble starch 3.0%, corn steep liquor 0.3%, soybean flour 1.0%, polypeptone 0.5%, yeast extract 0.1%, oatmeal agar 0.2%, sodium chloride 0.3%, and precipitated calcium carbonate 0.5% and incubation was carried out on a reciprocating shaker at 24° C. for 2 days. The culture, 500 mL, was transferred to a 200-L fermentor containing 120 L of a production medium (pH 6.5) composed of glucose 0.5%, dextrin 5.0%, soybean meal 3.5%, yeast extract 0.5%, precipitated calcium carbonate 0.7%, ACTOCOL™ 31-56 (Takeda Chemical Industries Ltd.) 0.05%, and silicone oil 0.05% and fermentation was carried out at a temperature of 22° C. and an internal pressure of 1.0 kg/cm$^2$ under 120 L/min. aeration and 120 rpm agitation for 42 hours.

The resulting culture broth (120 L) was adjusted to pH 7 and filtered with a filter aid (Radiolite 600, Showa Chemical Industry). The filtrate (130 L) was adjusted to pH 7 and subjected to HP-20 (7 L) column chromatography. After the column was washed with water (21 L), elution was carried out with 30% (v/v) isopropyl alcohol/$H_2O$ (28 L). The eluate was concentrated and the residue was diluted with water to a volume of 30 L and subjected to CNP-80 (H-form, 15 L) column chromatography. After the column was washed with water (45 L), elution was carried out with 2N-aqueous ammonia (53 L). The eluate was concentrated and subjected to PA-412 (OH-form, 2 L) column chromatography. The column was washed with water (6 L) and 1 M sodium chloride/$H_2O$ (2 L) in that order and serial elution was carried out with 1 M sodium chloride/$H_2O$ (10 L) and 1N-hydrochloric acid (4 L). The eluate was adjusted to pH 7 and subjected to HP-20 (1 L) column chromatography. The column was washed with water (3 L) and elution was carried out with 30% (v/v) isopropyl alcohol/$H_2O$ (3.4 L). The eluate was concentrated, adjusted to pH 7, and subjected to HP-20S (400 mL) column chromatography. After the column was washed with water (1.2 L), serial elution was carried out with 5% (v/v) isopropyl alcohol/$H_2O$ (1.2 L) and 10% (v/v) isopropyl alcohol/$H_2O$ (1.2 L). The 5% (v/v) isopropyl alcohol/$H_2O$ eluate was concentrated and subjected to HP-20SS (100 mL) column chromatography. This column was washed with water (200 mL) and serial elution was carried out using water (100 mL), 2% (v/v) isopropyl alcohol/$H_2O$ (300 mL), and 5% (v/v) isopropyl alcohol/$H_2O$ (300 mL). The eluate was concentrated and allowed to stand at 7° C. and the crystal crop was harvested to provide HC-70III (Compound 3; 1.3 g). The 10% (v/v) isopropyl alcohol/$H_2O$ eluate from the HP-20S (400 mL) column was concentrated, and after addition of methanol, the concentrate was allowed to stand at 7° C. and the resulting crystals (1.7 g) were collected by filtration. This crystal crop was recrystallized twice from water. In this manner, a crystal crop (1.3 g) composed predominantly of HC-70II was obtained. Of this crystal crop, 719 mg was subjected to HP-20S (70 mL) column chromatography. The column was washed with water (210 mL), 2% (v/v,) isopropyl alcohol/$H_2O$ (210 mL), and 5% (v/v) isopropyl alcohol/$H_2O$ (210 mL), and elution was carried out with 10% (v/v) isopropyl alcohol/$H_2O$ (420 mL). The HC-70II fraction was concentrated and allowed to stand at 7° C. and the resulting crystals were recovered by filtration to provide HC-70II (Compound 2; 479 mg).

EXAMPLE 2

(S)-3-[(2S,3R,4R,5S)-2,3,4,6-tetrahydroxy-5-(L-valyl-L-valyl-L-leucyl)aminohexanoyl]amino-3-phenylpropionic acid (HC-70I, compound 1)

A loopful of Bacillus sp. HC-70 fully grown on a slant medium composed of glucose 0.1%, tryptone 0.5%, yeast extract 0.25%, and agar 1.5% was used to inoculate a sterilized 2-L Sakaguchi flask containing 500 mL of a seed culture medium (pH 7.0) composed of glucose 2.0%, soluble starch 3.0%, corn steep liquor 0.3%, soybean flour 1.0%, polypeptone 0.5%, yeast extract 0.1%, oatmeal agar 0.2%, sodium chloride 0.3%, and precipitated calcium carbonate 0.5% and incubation was carried out on a reciprocating shaker at 24° C. for 2 days. This culture, 500 mL, was transferred to a 200-L fermenter containing 120 L of a production medium (pH 6.5) composed of glucose 0.5%, dextrin 5.0%, soybean meal 3.5%, yeast extract 0.5%, precipitated calcium carbonate 0.7%, ACTOCOL™ 31–56 (Takeda Chemical Industries Ltd.) 0.05%, and silicone oil 0.05% and was incubated at a temperature of 22° C. and an internal pressure of 1.0 kg/cm under 120 L/min. aeration and 120 rpm agitation for 24 hours.

A 2-batch equivalent of the resulting fermentation broth (120 L) was filtered using a filter aid (Radiolite 600). The filtrate (245 L) was adjusted to pH 6 and subjected to HP-20 (15 L) column chromatography. The column was washed with water (45 L) and elution was carried out with 30% (v/v) isopropyl alcohol/$H_2O$ (60 L). The eluate was chromatographed on a CNP-80 (H-form, 20 L) column, and after the column was washed with water (60 L), elution was carried out with 2N-aqueous ammonia (80 L). This eluate was concentrated, adjusted to pH 6, and subjected to HP-20 (2.4 L) column chromatography. After the column was serially washed with water (7.2 L) and 5% (v/v) isopropyl alcohol/$H_2O$ (7.2 L), elution was carried out with 10% (v/v) isopropyl alcohol/$H_2O$ (7.2 L) and 20% (v/v) isopropyl alcohol/$H_2O$ (11.5 L). The eluate was concentrated and serially passed through IR-120 (Na-form, 1.5 L), IRA-67 (OH-form, 1.5 L), and SP-850 (2 L) columns. After washing with water (8 L), the SP-850 (2 L) column was further washed with 0.2N-aqueous ammonia (2 L), water (6 L), and 10% (v/v) isopropyl alcohol/$H_2O$ (2 L) in the order mentioned. Then, elution was carried out with 10% (v/v)-isopropyl alcohol/$H_2O$ (4 L). The eluate was concentrated and allowed to stand at 7° C. and the resulting crystal crop (1.4 g) was harvested by filtration. Of this crystal crop, 1.2 g was subjected to HP-20 (150 mL) column chromatography. After the column was washed with water (450 mL) and 2% (v/v) isopropyl alcohol/$H_2O$ (450 mL) in that order, serial elution was carried out using 5% (v/v) isopropyl alcohol/$H_2O$ (900 mL), 10% (v/v) isopropyl alcohol/$H_2O$ (900 mL), and 15% (v/v) isopropyl alcohol/$H_2O$ (450 mL). The HC-70I fraction was concentrated and allowed to stand at 7° C. and the resulting crystals were recovered to provide HC-70I (Compound 1; 199 mg).

EXAMPLE 3

(S)-3-[(2S,3R,4R,5S)-2,3,4,6-tetrahydroxy-5-(L-valyl-L-leucyl)aminohexanoyl]amino-3-phenylpropionate hydrochloride (HC-70II monohydrochloride, compound 4)

To HC-70II (Compound 2; 200 mg) were added 0.1N-hydrochloric acid (3.4 mL) and water (60 mL), and the mixture was warmed to prepare a solution. This solution was filtered through DISMIC-25CS (0.45 μm, Toyo Roshi) and the filtrate was freeze-dried to provide HC-70II monohydrochloride (Compound 4; 199 mg).

Elemental analysis (for $C_{26}H_{42}N_4O_9 \cdot HCl \cdot 2.5H_2O$) Found: C, 48.93; H, 7.18; N, 8.86; Cl, 5.64 Calcd.: C, 49.09; H, 7.61; N, 8.81; Cl, 5.57

EXAMPLE 4

(S)-3-[(2S,3R,4R,5S)-5-amino-2,3,4,6-tetrahydroxyhexanoyl]amino-3-phenylpropionic acid (compound 5)

In phosphate buffer (40 mM, pH 8; 47.5 mL) was dissolved HC-70III (Compound 3; 190 mg) followed by addition of an aqueous solution of cobalt chloride (1 M, 0.19 mL) and Actinase E (19 mg, Kaken Pharmaceutical Co.), and the reaction was carried out at 37° C. for 2 hours. This reaction mixture was filtered through a filter paper (No. 2, Toyo Roshi) and the filtrate was subjected to HP-20 (50 mL) column chromatography. The column was washed with water (50 mL) and serial elution was carried out with water (100 mL) and 20% (v/v) isopropyl alcohol/$H_2O$ (200 mL). The eluate was concentrated and freeze-dried to provide crude powders (149 mg).

The above crude powders were subjected to preparative HPLC [column: YMC-Pack SH-363-15, ODS (YMC), mobile phase: 5% (v/v) acetonitrile/0.02 M phosphate buffer (pH 4.5), flow rate: 12 mL/min]. The 400 to 600 mL fractions were pooled, adjusted to pH 7, and concentrated to 120 mL under reduced pressure. The concentrate was chromatographed on an HP-20 (60 mL) column, and after the column was washed with water (180 mL), elution was carried out with 20% (v/v) isopropyl alcohol/$H_2O$ (240 mL). The eluate was concentrated and freeze-dried to provide Compound 5 as white powders (103 mg).

$^{13}$C-NMR (DMSO-$d_6$, δ ppm): 174.9, 172.3, 143.4, 127.9, 126.3, 126.2, 71.4, 70.8, 66.6, 60.9, 53.3, 49.7, 43.1

Elemental analysis (for $C_{15}H_{22}N_2O_7 \cdot 1.5H_2O$) Found: C, 49.11; H, 6.78; N, 7.89 Calcd.: C, 48.78; H. 6.82; N, 7.58

EXAMPLE 5

(Acquisition of HC-70III by using *Bacillus insolitus* HC-72)

A loopful of *Bacillus insolitus* HC-72 sufficiently grown on a slant medium composed of glucose 0.1%, tryptone 0.5%, yeast extract 0.25%, and agar 1.5% was used to inoculate a 2 L Sakaguchi flask containing 500 mL of a seed culture medium (pH 7.0) composed of glucose 2.0%, soluble starch 3.0%, corn steep liquor 0.3%, soybean flour 1.0%, polypeptone 0.5%, yeast extract 0.1%, sodium chloride 0.3%, and precipitated calcium carbonate 0.5% and incubation was carried out on a reciprocating shaker at 28° C. for 1 day. The culture, 500 mL, was transferred to a 200-L fermentor containing 120 L of a production medium (pH 7.0) composed of glucose 2.0%, soluble starch 3.0%, corn steep liquor 0.3%, soybean flour 1.0%, polypeptone 0.5%, yeast extract 0.1%, sodium chloride 0.3%, precipitated calcium carbonate 0.5%, ACTOCOL™ 31-56 (Takeda Chemical Industries Ltd.) 0.05%, and silicone oil 0.05% and incubated at a temperature of 24° C. and an internal pressure of 1.0 kg/cm$^2$ under 120 L/min. aeration and 120 rpm agitation for 48 hours. The culture, 10 L, was transferred to a 2000-L fermentor containing 1200 L of a production medium (pH 7.0) composed of glucose 0.5%, myo-inositol 1.0%, soybean meal 5.0%, corn steep liquor 1.0%, ACTOCOLυ 31-56 (Takeda Chemical Industries Ltd.) 0.05%, and silicone oil 0.05% and incubated at a temperature of 28° C. and an internal pressure of 1.0 kg/cm$^2$ under 840 L/min. aeration and 30 rpm agitation for 114 hours.

The fermentation broth (1200 L) thus obtained was adjusted to pH 5 and a flocculating agent [0.5 (w/v) Sanfloc C-109P, Sanyo Chemical Industries, Ltd.] was added for flocculation. The broth was then filtered with a filter aid (Radiolite 600). The filtrate (1200 L) was adjusted to pH 5 and subjected to charcoal (Granular Shirasagi, 25 L) and SP-850 (100 L) column chromatographies, followed by washing with water (300 L). The SP-850 column alone was serially washed with 0.1N-sodium hydroxide/$H_2O$ (300 L), water (300 L), 0.1N-sulfuric acid (300 L), and water (300 L), and elution was carried out with 25% (v/v) isopropyl alcohol/$H_2O$ (400 L). The HC-70III fraction was adjusted to pH 4.5 and subjected to UBK-510L (Na-form, 150 L) column chromatography. After the column was washed with water (150 L), fractional elution was carried out with 0.01N-aqueous ammonia (600 L). The HC-70III fraction was adjusted to pH 8 and passed columnwise over PK-216 (Na-form, 25 L) and IRA-67 ($CH_3COO$-form, 25 L) in that order, followed by washing with water (100 L). The effluent and washes were combined, adjusted to pH 5, concentrated, and allowed to stand at 7° C. The resulting crystal crop was harvested by filtration to provide HC-70III (Compound 3; 380 g).

EXAMPLE 6

(S)-3-[(2S,3R,4R,5S)-2,3,4,6-tetrahydroxy-5-(L-valyl-L-isoleucyl-L-leucyl)aminohexanoyl]amino-3-phenylpropionic acid (HC-70I-A, compound 1A) and (S)-3-[(2S,3R,4R,5S)-2,3,4,6-tetrahydroxy-5-(L-valyl-L-leucyl-L-leucyl)aminohexanoyl]amino-3-phenylpropionic acid (HC-70I-B, Compound 1B)

A loopful of Bacillus sp. HC-70 sufficiently grown on a slant medium composed of glucose 0.1%, tryptone 0.5%, yeast extract 0.25%, and agar 1.5% was used to inoculate a 2 L Sakaguchi flask containing 500 mL of a seed culture medium (pH 6.5) composed of glucose 2.0%, soluble starch 3.0%, corn steep liquor 0.3%, soybean flour 1.0%, polypeptone 0.5%, yeast extract 0.1%, sodium chloride 0.3%, and precipitated calcium carbonate 0.5% and incubation was carried out on a reciprocating shaker at 24° C. for 2 days. The culture, 500 mL, was transferred to a 200-L fermentor containing 120 L of a production medium (pH 6.5) composed of dextrin 5.0%, glucose 0.5%, soybean meal 3.5%, yeast extract 0.5%, precipitated calcium carbonate 0.5%, ACTOCOL™ 31-56 (Takeda Chemical Industries Ltd.) 0.05%, and silicone oil 0.05% and was incubated at a temperature of 22° C. and an internal pressure of 1.0 kg/cm$^2$ under 120 L/min. aeration and 120 rpm agitation for 42 hours.

A 2-batch equivalent of the fermentation broth (120 L) thus obtained was filtered with a filter aid (Radiolite 600). The filtrate (250 L) was adjusted to pH 6 and subjected to HP-20 (15 L) column chromatography. After the column was washed with water (45 L), elution was carried out with 30% (v/v) isopropyl alcohol/$H_2O$ (60 L). The eluate was subjected to CNP-80 (H-form, 20 L) column chromatography, and after the column was washed with water (60 L), elution was carried out with 2N-aqueous ammonia (80 L). The eluate was concentrated, adjusted to pH 6, and passed columnwise over IR-120 ($NH_4$-form, 1.5 L), IRA-67 (OH-form, 1.5 L), and SP-850 (2 L) in the order mentioned, followed by washing with water (8 L). The SP-850 (2 L) column alone was washed serially with 0.2N-aqueous ammonia (2 L), water (6 L), 0.1N-hydrochloric acid (2 L), water (6 L), and 5% (v/v) isopropyl alcohol/$H_2O$ (6 L), and fractional elution was carried out using 20% (v/v) isopropyl alcohol/$H_2O$ (8 L) and 30% (v/v) isopropyl alcohol/$H_2O$ (6 L). The fraction containing HC-70I-A and HC-70I-B (11.5 L) was then passed columnwise over IR-120 ($NH_4$-form, 0.5 L) and IRA-67 ($CH_3COO$-form, 0.5 L) in the order mentioned. The effluent was concentrated and allowed to stand at 7° C. and the resulting crystals (9.6 g) were recovered by filtration. Of this crystal crop, 4.0 g was dissolved in N,N-dimethylformamide and subjected to preparative HPLC [instrument: LC-300G, column: 100 φ×1,000 L(mm) (Kurita Water Industries Ltd.), stationary phase: YMC.GEL KE-ODS-10S (YMC), mobile phase: 17% (v/v) acetonitrile/0.02 M phosphate buffer (pH 4.5), flow rate: 30 mL/min] to obtain an HC-70I-A fraction (60 to 85 min) and an HC-70I-B fraction (87 to 100 min). The HC-70I-A fraction was concentrated and subjected to HP-20 (100 mL) column chromatography. After the column was washed-with water (300 mL), fractional elution was carried out using 20% (v/v) isopropyl alcohol/$H_2O$ (600 mL) and 0.1N-ammonia/20% (v/v) isopropyl alcohol/$H_2O$ (600 mL). The HC-70I-A fraction (600 mL) was concentrated and allowed to stand at 7° C., and the resulting crystals were collected by filtration to provide HC-70I-A (Compound 1A; 249 mg). The HC-70I-B fraction (0.4 L) eluted from the preparative HPLC column was concentrated and allowed to stand at 7° C. and the resulting crystals were recovered by filtration to provide HC-70I-B (Compound 1B; 400 mg).

HC-70I-A (Compound 1A)

Optical rotation: −67° (c=0.50, 0.1N HCl, 21° C.)

FAB-MS: m/z 668 (M+H)$^+$

Elemental analysis (%) (calculated as containing 2 mols of water) Found: C, 54.54; H, 8.16; N, 10.12 Calcd.: C, 54.61; H, 8.16; N, 9.95

Molecular formula: $C_{32}H_{53}N_5O_{10}$ $^{13}$C-NMR spectrum (in DMSO-$d_6$, δ ppm): 172.7, 172.4, 172.3, 172.2, 170.8, 142.6, 127.9, 126.5, 71.0, 70.8, 67.2, 60.5, 58.8, 56.5, 51.1, 50.8, 49.0, 41.2, 40.5, 36.7, 30.8, 24.3, 24.0, 23.1, 21.3, 19.0, 16.9, 15.3, 10.8

Amino acid analysis: analyzed after 72 hr of hydrolysis in 6N-hydrochloric acid at 110° C. Leucine (1 mol), isoleucine (1 mol), valine (1 mol)

High-performance liquid chromatography (HPLC)

Column: YMC-Pack ODS-A, A312, 150×6.0 mm (YMC)

Mobile phase: 15% (v/v) acetonitrile/0.02 M phosphate buffer (pH 4.5)

Flow rate: 1.0 mL/min

Detection: UV adsorptiometry, 214 nm

Retention time: 27 min

Thin-layer chromatography (TLC):

Stationary phase: silica gel $60F_{254}$, 0.25 mm (Merck, Germany)

Developing solvent: n-butanol/acetic acid/water (12:3:5)

Rf: 0.51

HC-70I-B (Compound 1B)

Optical rotation: −75° (c=0.50, 0.1N HCl, 21° C.)

FAB-MS: m/z 668 (M+H)$^+$

Elemental analysis (%) (calculated as containing 3.5 mols of water) Found: C, 52.59; H, 8.03; N, 9.78 Calcd.: C, 52.59; H, 8.27; N, 9.58

Molecular formula: $C_{32}H_{53}N_5O_{10}$ $^{13}$C-NMR spectrum (in DMSO-$d_6$, δ ppm): 172.8, 172.5, 172.3, 171.9, 142.6, 128.0, 126.4, 71.0, 70.8, 67.2, 60.5, 59.0, 51.0, 50.7, 49.1, 41.2, 40.9, 40.4, 30.8, 24.1, 23.1, 22.9, 21.6, 21.3, 19.0, 16.9

Amino acid analysis: analyzed after 72 hr of hydrolysis in 6N-hydrochloric acid at 110° C. Leucine (2 mol), valine (1 mol)

High-performance liquid chromatography (HPLC)

Column: YMC-Pack ODS-A, A312, 150×6.0 mm (YMC)

Mobile phase: 15% (v/v) acetonitrile/0.02 M phosphate buffer (pH 4.5)

Flow rate: 1.0 mL/min

Detection: UV adsorptiometry, 214 nm

Retention time: 39 min

Thin-layer chromatography (TLC):

Stationary phase: silica gel $60F_{254}$, 0.25 mm (Merck, Germany)

Developing solvent: n-butanol/acetic acid/water (12:3:5)

Rf: 0.54

EXAMPLE 7

(S)-3-[(2S,3R,4R,5S)-5-(N-acetyl-L-leucyl)amino-2,3,4,6-tetrahydroxyhexanoyl]amino-3-phenylpropionic acid monosodium salt (compound 6)

HC-70III (Compound 3; 50 mg) was dissolved in an aqueous solution of potassium hydrogencarbonate (50 mM, 20 mL) followed by addition of acetic anhydride (22 μL), and the reaction was carried out at room temperature for 1 hour. This reaction mixture was adjusted to pH 6.5 and subjected to HP-20 (5 mL) column chromatography. After the column was washed with water (5 mL), elution was carried out with water (10 mL) and 30% (v/v) isopropyl alcohol/$H_2O$ (30 mL). The eluate was concentrated and freeze-dried to provide the titled compound (Compound 6; 49 mg).

$^1$H-NMR (DMSO-$d_6$, δ ppm): 0.84(3H,d,J=6.4 Hz), 0.87 (3H,d,J=6.5 Hz), 1.44(2H,t,J=7.2 Hz), 1.57(1H,m), 1.83(3H, s), 2.53(2H,d,J=6.8 Hz), 3.45(2H,m), 3.48(1H,d,J=9.8 Hz), 3.76(1H,d,J=9.8 Hz), 3.95(1H,q like), 4.12(1H,s), 4.30(1H,q like), 5.11(1H,q like), 7.16(1H,m), 7.23(2H,t like), 7.32(1H, d,J=7.0 Hz), 7.33(2H,t like), 8.05(1H,d,J=8.3 Hz), 8.75(1H, d,J=7.7 Hz).

FAB-MS: m/z 536 (M+H)$^+$

EXAMPLE 8

Methyl(S)-3-[(2S,3R,4R,5S)-2,3,4,6-tetrahydroxy-5-(L-leucyl)aminohexanoyl]amino-3-phenylpropionate monohydrochloride (compound 7)

HC-70III (Compound 3; 50 mg) was dissolved in methanol (10 mL) followed by addition of HCl-methanol Reagent 10 (10 mL, Tokyo Kasei Kogyo), and the reaction was carried out at room temperature for 16 hours. This reaction mixture was concentrated to dryness in nitrogen gas, diluted with water (10 mL), adjusted to pH 6.5, further diluted with water (40 mL), and subjected to HP-20 (10 mL) column chromatography. The column was washed with water (30 mL) and 30% (v/v) isopropyl alcohol/$H_2O$ (10 mL), and elution was then carried out with 30% (v/v) isopropyl alcohol/$H_2O$ (20 mL) and 50% (v/v) isopropyl alcohol/$H_2O$ (20 mL) The eluate was concentrated and freeze-dried to provide the titled compound (Compound 7; 34 mg).

$^1$H-NMR (DMSO-$d_6$, δ ppm): 0.86(3H,d,J=6.6 Hz), 0.89 (3H,d,J=6.7 Hz), 1.24(1H,ddd,J=4.8,9.2,13.5 Hz), 1.46(1H, ddd,J=4.4,9.0,13.5 Hz), 1.75(1H,m), 2.84(1H,dd,J=7.4,15.8 Hz), 2.91(1H,dd,J=6.8,15.8 Hz), 3.40–3.48(3H,m), 3.51 (3H,s), 3.76(1H,m), 3.97(1H,q like), 4.11(1H,br d,J=4.3 Hz), 4.56(1H,d,J=6.3 Hz), 4.63(1H,br s), 4.90(1H,br d,J=6.0 Hz), 5.24(1H,br d,J=7.0 Hz), 5.27(1H,q like), 7.20–7.37(5H, m), 7.45(1H,br d,J=7.8 Hz), 8.12(1H,br d,J=8.9 Hz).

FAB-MS: m/z 470 (M+H)$^+$

Reference Example 1

(2S,3R,4R,5S)-2,3,4,6-tetrahydroxy-5-(L-leucyl) amino hexanoic acid (De-β-Phe-HC-70III)

HC-70III (Compound 3; 910 mg) was dissolved in 0.5N-sodium hydroxide/$H_2O$ (200 mL) and the solution was stirred at 37° C. for 24 hours. This reaction mixture was adjusted to pH 5 and subjected to SP-207 (100 mL) column chromatography. The column was washed with water (300 mL), and the effluent and washes were combined and subjected to charcoal (Granular Shirasagi, 70 mL) column chromatography. After the column was washed with water (210 mL), elution was carried out with 10% (v/v) isopropyl alcohol/$H_2O$ (210 mL). The eluate was concentrated and passed columnwise over Sephadex G-10 (600 mL), and fractional elution was carried out with water (600 mL). The fraction containing De-β-Phe-HC-70III was concentrated to dryness and the residue was diluted with water (2 mL) and ethanol (4 mL) and allowed to stand at 7° C. The resulting crystals were harvested by filtration to provide the titled compound (De-β-Phe-HC-70III; 300 mg).

$^1$H-NMR (DMSO-$d_6$, δ ppm): 0.86(3H,d,J=7.1 Hz), 0.89 (3H,d,J=7.3 Hz), 1.36(1H,m), 1.49(1H,m), 1.67(1H,m), 3.30 (1H,dd,J=3.9,9.3 Hz), 3.38(1H,dd,J=6.3,9.8 Hz), 3.43(1H, dd,J=9.3,9.8 Hz), 3.58(1H,t like), 3.70(1H,d,J=9.3 Hz), 3.85 (1H,d,J=3.9 Hz), 4.05(1H,d like), 7.90(1H,d,J=8.6 Hz).

FAB-MS: m/z 309 (M+H)$^+$

Reference Example 2 diphenylmethyl (2S,3R,4R,5S)-5-(N-benzyloxycarbonyl-L-leucyl)amino-2,3,4,6-tetrahydroxyhexanoate To a solution of (2S,3R,4R,5S)-2,3,4,6-tetrahydroxy-5-(L-leucyl)aminohexanoic acid (300 mg) in water (20 ml)

and tetrahydrofuran (5 ml) were added benzyl chloroformate (0.167 ml) and sodium hydrogencarbonate (245 mg) and the mixture was stirred at room temperature for 3 hours. After removal of tetrahydrofuran by evaporation, the aqueous layer was acidified with 1N hydrochloric acid (3 ml) and extracted with ethyl acetate (100 ml×2). The extract was washed with saturated brine and dried over anhydrous sodium sulfate. After concentration under reduced pressure, the residue was dissolved in methanol (10 ml), followed by addition of diphenyldiazomethane (400 mg). The whole was stirred at room temperature for 14 hours and concentrated under reduced pressure. The residue was subjected to silica gel column chromatography, followed by elution with ethyl acetate-methanol (10:1). The effective fractions were combined and concentrated under reduced pressure to afford the title compound (495 mg).

$^1$H-NMR(CD$_3$OD) δ: 0.86–0.90(6H,m), 1.49–1.76(3H, m), 3.62–3.69(2H,m), 3.83(1H,m), 3.99(1H,m), 4.16–4.27 (2H,m), 4.35(1H,m), 4.56(1H,d,J=1.8 Hz), 5.05–5.08(2H, m), 6.91(1H,s), 7.24–7.38(15H,m).

Reference Example 3 diphenylmethyl (2S,3R,4R,5S)-2,3,4,6-tetraacetoxy-5-(N-benzyloxycarbonyl-L-leucyl)aminohexanoate To a solution of diphenylmethyl (2S,3R,4R,5S)-5-(N-benzyloxycarbonyl-L-leucyl)amino-2,3,4,6-tetrahydroxyhexanoate (200 mg) in pyridine (5 ml) were added acetic anhydride (3 ml) and dimethylaminopyridine (40 mg) and the mixture was stirred at room temperature for 16 hours. After concentration under reduced pressure, to the residue was added 1N hydrochloric acid (10 ml) and the whole was extracted with ethyl acetate (100 ml×2). The extract was washed with saturated brine and dried over anhydrous sodium sulfate. Removal of the organic solvent gave a residue, which was passed through silica gel column chromatography, followed by elution with ethyl acetate-hexane (1:2). The effective fractions were combined and concentrated under reduced pressure to afford the title compound (256 mg).

$^1$H-NMR(CDCl$_3$) δ: 0.91–0.95(6H,m), 1.46–1.69(3H,m), 1.81(3H,s), 1.98(3H,s), 2.07(3H,s), 2.17(3H,s), 3.86(1H,dd, J=11.4 Hz,6.6 Hz), 3.99–4.17(2H,m), 4.47(1H,m), 5.01–5.09(2H,m), 5.22(1H,d,J=1.8 Hz), 5.40(1H,d,J=9.6 Hz), 5.52(1H,d,J=9.6 Hz), 6.37(1H,d,J=8.8 Hz), 6.76(1H,s), 7.26–7.34(16H,m).

Reference Example 4

(2S,3R,4R,5S)-2,3,4,6-tetraacetoxy-5-(N-benzyloxycarbonyl-L-leucyl)aminohexanoic acid Diphenylmethyl (2S,3R,4R,5S)-2,3,4,6-tetraacetoxy-5-(N-benzyloxycarbonyl-L-leucyl)aminohexanoate (270 mg) was dissolved in trifluoroacetic acid (5 ml) and the solution was stirred at room temperature for 1 hour. After concentration under reduced pressure, the residue was passed through silica gel column chromatography, followed by elution with ethyl acetate-methanol (10:1). The effective fractions were combined and concent rated under reduced pressure to afford the title compound (214 mg).

$^1$H-NMR(CD$_3$OD) δ: 0.92–0.96(6H,m), 1.50–1.67(3H, m), 1.96(3H,s), 2.04(3H,s), 2.06(3H,s), 2.11(3H,s), 3.83(1H, m), 4.11–4.23(3H,m), 4.52(1H,m), 4.95(1H,m), 5.07(1H, m), 5.36(1H,d,J=10.0 Hz), 5.46(1H,d,J=10.0 Hz), 7.28–7.32 (5H,m).

EXAMPLE 9

(S)-3-[(2S,3R,4R,5S)-2,3,4,6-tetrahydroxy-5-(L-leucyl)aminohexanoyl]amino-3-phenylpropionic acid hydrochloride To a solution of (S)-3-[(2S,3R,4R,5S)-2,3,4,6-tetrahydroxy-5-(L-leucyl)aminohexanoyl]amino-3-phenylpropionic acid (Compound 3) (2.00 g) in water (50 ml) was added 1N hydrochloric acid (4.83 ml). After the mixture was filtrated through membrane filter, the filtrate was concentrated under reduced pressure. Recrystallization from methanol-diethylether provided the title compound (1.84 g).

$^1$H-NMR(CD$_3$OD) δ: 1.02(3H,d,J=6.4 Hz), 1.03(3H,d,J=6.4 Hz), 1.60–1.80(3H,m), 2.85(1H,dd,J=16.0 Hz,7.0 Hz), 3.65–4.40(7H,m), 5.30–5.50(1H,m), 7.20–7.45(5H,m), 8.42 (1H,d,J=8.6 Hz).

EXAMPLE 10 diphenylmethyl (S)-3-[(2S,3R,4R,5S)-2,3,4,6-tetrahydroxy-5-(L-leucyl)aminohexanoyl]amino-3-phenylpropionate To a solution of (S)-3-[(2S,3R,4R,5S)-2,3,4,6-tetrahydroxy-5-(L-leucyl)aminohexanoyl]amino-3-phenylpropionic acid hydrochloride (1.84 g) in methanol (40 ml) was added a solution of diphenyldiazomethane (1.45 g) in methanol (20 ml) and the mixture was stirred at room temperature for 4 hours. After addition of acetic acid (0.1 ml), the reaction mixture was extracted with ethyl acetate. The extract was washed with aqueous sodium hydrogencarbonate solution and saturated brine respectively and the ethyl acetate solution was dried over anhydrous sodium sulfate. Removal of the organic solvent gave a residue, which was purified by silica gel column chromatography. Elution with ethyl acetate-methnaol (2:1) provided the title compound (2.05 g).

$^1$H-NMR(CD$_3$OD) δ: 0.93(3H,d,J=5.0 Hz), 0.96(3H,d,J=4.8 Hz), 1.10–1.90(3H,m), 3.02(1H,dd,J=15.8 Hz,7.6 Hz), 3.13(1H,dd,J=15.8 Hz,5.8 Hz), 3.35–4.35(7H,m), 5.35–5.50 (1H,m), 6.73(1H,s), 7.10–7.40(15H,m).

EXAMPLE 11 diphenylmethyl (S)-3-[(2S,3R,4R,5S)-2,3,4,6-tetrahydroxy-5-(L-leucyl)aminohexanoyl]amino-3-phenylpropionate hydrochloride To a solution of diphenylmethyl (S)-3-[(2S,3R,4R,5S)-2,3,4,6-tetrahydroxy-5-(L-leucyl)aminohexanoyl]amino-3-phenylpropionate (246 mg) in methanol (1 ml) was added 1N hydrochloric acid (0.396 ml) at room temperature. Concentration gave a residue, which was recrystallized from methanol-diethylether to afford the title compound (180 mg).

$^1$H-NMR(CD$_3$OD) δ: 1.00(3H,d,J=5.6 Hz), 1.02(3H,d,J=5.6 Hz), 1.60–1.80(3H,m), 3.04(1H,dd,J=16.0 Hz,7.0 Hz), 3.15(1H,dd,J=16.0 Hz,5.4 Hz), 3.55–4.40(7H,m), 5.43(1H, dd,J=7.6 Hz,5.4 Hz), 6.73(1H,s), 7.10–7.40(15H,m).

EXAMPLE 12 ethyl (S)-3-[(2S,3R,4R,5S)-2,3,4,6-tetrahydroxy-5-(L-leucyl)aminohexanoyl]amino-3-phenylpropionate To (S)-3-[(2S,3R,4R,5S)-2,3,4,6-tetrahydroxy-5-(L-leucyl)aminohexanoyl]amino-3-phenylpropionic acid (Compound 3) (500 mg) was added a 28% solution of hydrogen chloride in ethanol (200 ml) and the mixture was stirred at room temperature for 20 hours. After concentration, the residue was subjected to silica gel column chromatography and eluted with acetonitrile-water (5:1). The effective fractions were combined and concentrated under reduced pressure. The residue was dissolved in water (10 ml) and neutralized with aqueous sodium hydrogencarbonate solution. The solution was passed through a column of DIAION HP-20SS (Mitsubishi kasei corporation), followed by elution with water-acetonitrile. The effective fractions were combined and concentrated under reduced pressure. The residue was recrystallized from chloroform-diethylether to afford the title compound (123 mg).

$^1$H-NMR(DMSO-d$_6$) δ: 0.85–1.00(6H,m), 1.07(3H,t,J=6.8 Hz), 1.40–1.80(3H,m), 2.70–3.00(2H,m), 3.00–5.50(8H,m), 3.96(2H,q,J=6.8 Hz), 7.10–7.45(5H,m), 8.00–8.30(2H,m).

EXAMPLE 13

(S)-3-[(2S,3R,4R,5S)-5-(N-benzyloxycarbonyl-L-leucyl)amino-2,3,4,6-tetrahydroxyhexanoyl]amino-3-phenylpropionic acid To a mixture of (S)-3-[(2S,3R,4R,5S)-2,3,4,6-tetrahydroxy-5-(L-leucyl)aminohexanoyl]amino-3-phenylpropionic acid (Compound 3) (2.28 g) and 0.2N aqueous sodium hydroxide solution (25 ml) were added benzyl chloroformate (0.714 ml) and 1N aqueous sodium hydroxide solution at 0° C. After stirring at room temperature for 3 hours, the mixture was washed with diethylether and acidified with 1N hydrochloric acid (20 ml). The aqueous solution was extracted with ethyl acetate and the organic layer was washed with saturated brine and dried over anhydrous sodium sulfate. Removal of the organic solvent gave a residue, which was recrystallized from diethylether-hexane to afford the title compound(1.51 g)

$^1$H-NMR(DMSO-d$_6$) δ: 0.86(3H,d,J=6.0 Hz), 0.87(3H,d, J=6.0 Hz), 1.30–1.80(3H,m), 2.60–3.00(2H,m), 3.20–5.40 (8H,m), 5.04(2H,s), 7.10–7.60(11H,m), 8.16(1H,d,J=8.8 Hz).

EXAMPLE 14 diphenylmethyl (S)-3-[(2S,3R,4R,5S)-5-(N-benzyloxycarbonyl-L-leucyl)amino-2,3,4,6-tetrahydroxyhexanoyl]amino-3-phenylpropionate To a solution of (S)-3-[(2S,3R,4R,5S)-2,3,4,6-tetrahydroxy-5-(L-leucyl)aminohexanoyl]amino-3-phenylpropionic acid hydrochloride (4.35 g) in methanol (100 ml) was added a solution of diphenyldiazomethane (3.40 g) in methanol (100 ml) under ice-cooling and the mixture was stirred at room temperature for 15 hours. Removal of the organic solvent gave a residue, which was suspended in water (200 ml). To the suspension were added sodium hydrogencarbonate (2.20 g) and benzyl chloroformate (18 ml) and the mixture was stirred at room temperature for 2 hours. The reaction mixture was extracted with ethyl acetate and the extract was washed with saturated brine. The organic layer was dried over anhydrous sodium sulfate and concentrated under reduced pressure. The residue was recrystallized from ethyl acetate to give the title compound (5.95 g).

$^1$H-NMR(CD$_3$OD) δ: 0.91–0.97(6H,m), 1.55–1.78(3H, m), 3.03–3.10(2H,m), 3.63–3.73(3H,m), 3.91(1H,dd,J=9.6 Hz,1.4 Hz), 4.16–4.23(1H,d,J=1.4 Hz), 5.10(2H,,s), 5.44 (1H,t,J=6.2 Hz), 7.13–7.36(20H,m).

EXAMPLE 15

(S)-3-[(2S,3R,4R,5S)-5-(N-benzyloxycarbonyl-L-leucyl)amino-2,3,4,6-tetrahydroxyhexanoyl]amino-3-phenylpropionic acid A solution of diphenylmethyl (S)-3-[(2S,3R,4R,5S)-5-(N-benzyloxycarbonyl-L-leucyl)amino-2,3,4,6-tetrahydroxyhexanoyl]amino-3-phenylpropionate (1.5 g) in trifluoroacetic acid (100 ml) was stirred at room temperature for 3 hours and concentrated under reduced pressure. The residue was passed through a column of silica gel, followed by elution with ethyl acetate:methanol (1:1). The effective fractions were combined and concentrated under reduced pressure. Recrystallization from ethyl acetate provided the title compound (0.86 g), which showed the same $^1$H-NMR with example 13.

EXAMPLE 16 pivaloyloxymethyl (S)-3-[(2S,3R,4R,5S)-5-(N-benzyloxycarbonyl-L-leucyl)amino-2,3,4,6-tetrahydroxyhexanoyl]amino-3-phenylpropionate To a solution of (S)-3-[(2S,3R,4R,5S)-5-(N-benzyloxycarbonyl-L-leucyl)amino-2,3,4,6-tetrahydroxyhexanoyl]amino-3-phenylpropionic acid (295 mg) and 1,8-diazabicyclo[5.4.0]undec-7-ene (0.082 ml) in dimethylformamide (2 ml) was added a solution of iodomethyl pivalate (139 mg) in dimethylformamide (1 ml) and the mixture was stirred at room temperature for 1 hour. After addition of water, the reaction mixture was extracted with ethyl acetate and the extract was washed with 10% aqueous citric acid solution, saturated aqueous sodium hydrogencarbonate solution andsaturated brine respectively. The organic solution was dried over anhydrous sodium sulfate and concentrated under reduced pressure. The residue was passed through a column of silica gel, followed by elution with ethyl acetate:methanol (10:1). The effective fractions were combined and concentrated under reduced pressure. Recrystallization from chloroform provided the title compound (160 mg).

$^1$H-NMR(DMSO-d$_6$) δ: 0.85(3H,d,J=6.2 Hz), 0.86(3H,d, J=6.2 Hz), 1.06(9H,s), 1.30–1.80(3H,m), 2.90–3.05(2H,m), 3.20–5.40(8H,m), 5.04(2H,s), 5.61(2H,s), 7.10–7.60(7H,m).

EXAMPLE 17 pivaloyloxymethyl (S)-3-[(2S,3R,4R,5S)-2,3,4,6-tetrahydroxy-5-(L-leucyl)aminohexanoyl]amino-3-phenylpropionate To a solution of pivaloyloxymethyl (S)-3-[(2S,3R,4R, 5S)-5-(N-benzyloxycarbonyl-L-leucyl)amino-2,3,4,6-tetrahydroxyhexanoyl]amino-3-phenylpropionate (150 mg) in methanol (5 ml) was added 10% palladium on activated carbon (30 mg) and the mixture was stirred under hydrogen atmosphere at room temperature for 1.5 hours. After removal of the catalyst by filtration, the filtrate was concentrated under reduced pressure. Recrystallization from ethyl acetate-hexane provided the title compound (101 mg).

$^1$H-NMR(DMSO-d$_6$) δ: 0.86(3H,d,J=5.8 Hz), 0.89(3H,d, J=5.8 Hz), 1.07(9H,s), 1.10–1.90(3H,m), 2.97(2H,d,J=6.2 Hz), 3.20–5.40(8H,m), 5.64(2H,s), 7.15–7.45(5H,m), 7.84 (1H,d,J=8.8 Hz), 8.14(1H,d,J=9.2 Hz).

EXAMPLE 18

(S)-3-[(2S,3R,4R,5S)-5-(N-benzyloxycarbonyl-L-leucyl)amino-2,3,4,6-tetrahydroxyhexanoyl]amino-3-phenylpropionamide A solution of (S)-3-[(2S,3R,4R,5S)-5-(N-benzyloxycarbonyl-L-leucyl)amino-2,3,4,6-tetrahydroxyhexanoyl]amino-3-phenylpropionic acid (295 mg), N-hydroxysuccinimide (58 mg) and N,N'-dicyclohexylcarbodimide (103 mg) in acetonitrile (10 ml)

was stirred at room temperature for 3 hours and the formed insoluble solid was filtrated off. Removal of the organic solvent gave a residue, which was dissolved in dimethylformamide (5 ml), followed by addition of 25% aqueous ammonia solution (1 ml). The mixture was stirred at room temperature for 1 hour and concentrated under reduced pressure. The residue was extracted with ethyl acetate and the extract was washed with 1N hydrochloric acid, saturated aqueous sodium hydrogencarbonate solution and saturated brine respectively. After drying over anhydrous sodium sulfate, removal of the organic solvent gave a residue, which was recrystallized from methanol-diethylether to give the title compound (97 mg).

$^1$H-NMR(DMSO-$d_6$) δ: 0.75–0.90(6H,m), 0.95–1.80(3H, m), 2.45–2.75(2H,m), 3.25–5.65(8H,m), 7.15–7.60(10H,m).

EXAMPLE 19

(S)-3-[(2S,3R,4R,5S)-2,3,4,6-tetrahydroxy-5-(L-leucyl)aminohexanoyl]amino-3-phenylpropionamide To a solution of (S)-3-[(2S,3R,4R,5S)-5-(N-benzyloxycarbonyl-L-leucyl)amino-2,3,4,6-tetrahydroxyhexanoyl]amino-3-phenylpropionamide (200 mg) in methanol (10 ml) was added 10% palladium on activated carbon (50 mg) and the mixture was stirred under hydrogen atmosphere at room temperature for 20 hours. After removal of the catalyst by filtration, the filtrate was concentrated under reduced pressure. Recrystallization from methanol-diethylether provided the title compound (140 mg).

$^1$H-NMR(DMSO-$d_6$) δ: 0.87(3H,d,J=6.0 Hz), 0.89(3H,d, J=6.0 Hz), 1.10–2.20(3H,m), 2.40–2.80(2H,m), 3.10–5.40 (8H,m), 7.15–7.50(5H,m), 7.79(1H,d,J=7.8 Hz), 8.34(1H,d, J=8.4 Hz).

EXAMPLE 20 diphenylmethyl (S)-3-[(2S,3R,4R,5S)-5-amino-2,3,4,6-tetrahydroxyhexanoyl]amino-3-phenylpropionate hydrochloride To a solution of (S)-3-[(2S,3R,4R,5S)-5-amino-2,3,4,6-tetrahydroxyhexanoyl]amino-3-phenylpropionic acid (compound 5) (3.40 g) in 1N hydrochloric acid (11 ml) was added methanol (10 ml) and the mixture was concentrated under reduced pressure. The residue was dissolved in methanol (100 ml), followed by addition of diphenyldiazomethane (3.88 g). The mixture was stirred at room temperature for 1.5 hours and concentrated under reduced pressure. The residue was washed with diethylether to afford the title compound (5.36 g).

$^1$H-NMR(DMSO-$d_6$) δ: 3.07(1H,d,J=7.0 Hz), 3.50–5.80 (6H,m), 6.68(1H,s), 7.10–7.20(15H,m), 8.24(1H,d,J=8.8 Hz).

EXAMPLE 21

(S)-3-[(2S,3R,4R,5S)-2,3,4,6-tetrahydroxy-5-(L-ornithyl)aminohexanoyl]amino-3-phenylpropionic acid dihydrochloride To a solution of $N^\alpha$-benzyloxycarbonyl-$N^\delta$-tert-butoxycarbonyl-L-ornithine (550 mg) in dimethoxyethane (7.5 ml) were added N-hydroxysuccinimide (173 mg) and N,N'-dicyclohexylcarbodiimide (309 mg) at 0° C. and the mixture was kept at 0° C. for 24 hours. The formed insoluble solid was filtrated off and the filtrate was concentrated under reduced pressure. The residue was dissolved in dimethylformamide (5 ml), followed by addition of triethylamine (0.209 ml) and diphenylmethyl (S)-3-[(2S,3R,4R,5S)-5-amino-2,3,4,6-tetrahydroxyhexanoyl]amino-3-phenylpropionate hydrochloride (818 mg) at room temperature and stirred at room temperature for 72 hours. To the mixture was added 10% aqueous citric acid solution and the whole was extracted with ethyl acetate. The extract was washed with saturated aqueous sodium hydrogencarbonate solution and saturated brine respectively and dried over anhydrous sodium sulfate. Removal of the organic solvent gave a residue, which was subjected to flush silica gel column chromatography, followed by elution with methanol-ethyl acetate (1:20). The effective fractions were combined and concentrated under reduced pressure. To the residue was added 4N hydrogen chloride solution in ethyl acetate (10 ml) and the mixture was stirred at room temperature for 2 hours. After concentration, the residue was dissolved in methanol (20 ml) and stirred at room temperature with 10% palladium on activated carbon (200 mg) under hydrogen atmosphere for 4 hours. After filtration, to the filtrate was added 1N hydrochloric acid (50 ml) and the whole was washed with dietylether. The aqueous layer was concentrated under reduced pressure to give a residue. Recrystallization from methanol-acetonitrile provided the title compound (376 mg).

$^1$H-NMR(DMSO-$d_6$) δ: 1.50–2.30(4H,m), 2.76–6.00 (12H,m), 7.10–7.50(5H,m), 8.10–8.50(2H,m).

EXAMPLE 22

(S)-3-[(2S,3R,4R,5S)-5-(α-L-glutamyl)amino-2,3,4,6-tetrahydroxyhexanoyl]amino-3-phenylpropionic acid hydrochloride Following the same procedure as described in example 21 with $N^\alpha$-benzyloxycarbonyl-L-glutamic acid γ-tert-butylester in place of $N^\alpha$-benzyloxycarbonyl-$N^\delta$-tert-butoxycarbonyl-L-ornithine, the title compound was prepared.

$^1$H-NMR(DMSO-$d_6$) δ: 1.80–2.30(4H,m), 2.76–3.00(2H, m), 3.50–6.00(8H,m), 7.10–7.50(5H,m).

EXAMPLE 23

(S)-3-[(2S,3R,4R,5S)-2,3,4,6-tetrahydroxy-5-(O-methyl-L-seryl)aminohexanoyl]amino-3-phenylpropionic acid To a solution of N-benzyloxycarbonyl-O-methyl-L-serine (380 mg) in dimethoxyethane (7.5 ml) were added N-hydroxysuccinimide (173 mg) and N,N'-dicyclohexylcarbodiimide (309 mg) at 0° C. and the mixture was kept at 0° C. for 24 hours. The formed insoluble solid was filtrated off and the filtrate was concentrated under reduced pressure. The residue was dissolved in dimethylformamide (5 ml), followed by addition of triethylamine (0.209 ml) and diphenylmethyl (S)-3-[(2S,3R,4R,5S)-5-amino-2,3,4,6-tetrahydroxyhexanoyl]amino-3-phenylpropionate hydrochloride (818 mg) at room temperature and stirred at room temperature for 72 hours. To the mixture was added 10% aqueous citric acid solution and the whole was extracted with ethyl acetate. The extract was washed with saturated aqueous sodium hydrogencarbonate solution and saturated brine respectively and dried over anhydrous sodium sulfate. Removal of the organic solvent gave a residue, which was subjected to flush silica gel column chromatography, followed by elution with methanol-ethyl acetate (1:20–1:3). The effective fractions were combined and concentrated under reduced pressure. The residue was dissolved in methanol (20 ml) and stirred at room temperature with 10% palladium on activated carbon (200 mg) under hydrogen atmosphere for 2 hours. After filtration, to the filtrate was added water and the whole was washed with diethylether. The aqueous layer was concentrated under reduced pressure to give a residue. Recrystallization from methanol-diethylether provided the title compound (263 mg).

$^1$H-NMR(DMSO-d$_6$) δ: 2.60–2.90(2H,m), 3.26(3H,s), 3.20–5.40(8H,m), 7.10–7.50(5H,m), 7.50–8.40(2H,m).

EXAMPLE 24

(S)-3-[(2S,3R,4R,5S)-5-(O-benzyl-L-seryl)amino-2, 3,4 6-tetrahydroxyhexanoyl]amino-3-phenylpropionic acid To a solution of O-benzyl-N-benzyloxycarbonyl-L-serine (329 mg) in acetonitrile (5 ml) were added N-hydroxysuccinimide (115 mg) and N,N'-dicyclohexylcarbodiimide (206 mg) at room temperature and the mixture was stirred at room temperature for 3 hours. The formed insoluble solid was filtrated off and the filtrate was concentrated under reduced pressure. The residue was dissolved in dimethylformamide (5 ml), followed by addition of triethylamine (0.139 ml) and diphenylmethyl (S)-3-[(2S, 3R, 4R,5S)-5-amino-2,3,4,6-tetrahydroxyhexanoyl]amino-3-phenylpropionate hydrochloride (545 mg) at room temperature and stirred at room temperature for 15 hours. To the mixture was added 10% aqueous citric acid solution and the whole was extracted with ethyl acetate. The extract was washed with saturated aqueous sodium hydrogencarbonate solution and saturated brine respectively and dried over anhydrous sodium sulfate. Removal of the organic solvent gave a residue, which was subjected to flush silica gel column chromatography, followed by elution with methanol-ethyl acetate (1:20). The effective fractions were combined and concentrated under reduced pressure. The residue was dissolved in methanol (30 ml) and stirred at room temperature with palladium hydroxide on carbon (100 mg) under hydrogen atmosphere(3–4 atm) at room temperature for 6 hours. After filtration, the filtrate was concentrated under reduced pressure to give a residue, which was passed through a column of DIAION CHP-20P (Mitsubishi kasei corporation), followed by elution with water-acetonitrile. The effective fractions were combined and concentrated under reduced pressure. The residue was recrystallized from methanol-diethylether to afford the title compound (97 mg).

$^1$H-NMR(DMSO-d$_6$) δ: 2.55–2.90(2H,m), 3.20–5.40 (10H,m), 4.50(2H,s), 7.10–7.50(10H,m), 7.84(1H,d,J=8.8 Hz), 8.29(1H,d,J=11.4 Hz).

EXAMPLE 25 diphenylmethyl (S)-3-[(2S,3R,4R,5S)-5-(O-tert-butyl-N-fluorenylmethyloxycarbonyl-L-seryl)amino-2,3,4,6-tetrahydroxyhexanoyl]amino-3-phenylpropionate To a solution of O-tert-butyl-N-fluorenylmethyloxycarbonyl-L-serine (575 mg) in acetonitrile (7.5 ml) were added N-hydroxysuccinimide (173 mg) and N,N'-dicyclohexylcarbodiimide (309 mg) at room temperature and the mixture was stirred at room temperature for 3 hours. The formed insoluble solid was filtrated off and the filtrate was concentrated under reduced pressure. The residue was dissolved in dimethylformamide (5 ml), followed by addition of triethylamine (0.139 ml) and diphenylmethyl (S)-3-[(2S,3R,4R,5S)-5-amino-2,3,4,6-tetrahydroxyhexanoyl]amino-3-phenylpropionate hydrochloride (545 mg) at room temperature and stirred at room temperature for 24 hours. To the mixture was added 10% aqueous citric acid solution and the whole was extract with ethyl acetate. The extract was washed with saturated aqueous sodium hydrogencarbonate solution and saturated brine respectively and dried over anhydrous sodium sulfate. Removal of the organic solvent gave a residue, which was recrystallized from diethylether-hexane to afford the title compound (1.156 g).

$^1$H-NMR(DMSO-d$_6$) δ: 1.19(9H,s), 2.86–6.00(15H,m), 6.80(1H,s), 7.05–8.20(23H,m).

EXAMPLE 26 diphenylmethyl (S)-3-[(2S,3R,4R,5S)-5-(O-tert-butyl-L-seryl)amino-2,3,4,6-tetrahydroxyhexanoyl] amino-3-phenylpropionate To diphenylmethyl (S)-3-[(2S,3R,4R,5S)-5-(O-tert-butyl-N-fluorenylmethyloxycarbonyl-L-seryl)amino-2,3,4,6-tetrahydroxyhexanoyl]amino-3-phenylpropionate (874 mg) was added piperidine (5 ml) and the mixture was stirred at room temperature for 5 hours. Removal of the organic solvent gave a residue, which was subjected to flush silica gel column chromatography, followed by elution with methanol-ethyl acetate (1:2). The effective fractions were combined and concentrated under reduced pressure. The residue was recrystallized from diethylether-hexane to afford the title compound (539 mg).

$^1$H-NMR(DMSO-d$_6$) δ: 1.12(9H,s),3.05(3H,d,J=7.0 Hz), 3.20–5.40(8H,m), 6.67(1H,s), 7.10–7.40(15H,m), 7.74(1H, d,J=8.0 Hz), 8.15(1H,d,J=9.0 Hz).

EXAMPLE 27

(S)-3-[(2S,3R,4R,5S)-2,3,4,6-tetrahydroxy-5-(L-seryl)aminohexanoyl]amino-3-phenylpropionic acid To diphenylmethyl (S)-3-[(2S,3R,4R,5S)-5-(O-tert-butyl-L-seryl)amino-2,3,4,6-tetrahydroxyhexanoyl]amino-3-phenylpropionate (300 mg) was added 4N hydrogen chloride solution in ethyl acetate (10 ml) and the mixture was stirred at room temperature for 1.5 hours. Removal of the organic solvent gave a residue, which was extracted with water. The aqueous layer was washed with diethylether and concentrated under reduced pressure. The residue was recrystallized from methanol-diethylether to afford the title compound (208 mg).

$^1$H-NMR(DMSO-d$_6$) δ: 2.65–3.00(2H,m), 3.20–5.60 (10H,m), 7.15–7.50(5H,m).

EXAMPLE 28

(S)-3-[(2S,3R,4R,5S)-2,3,4,6-tetrahydroxy-5-(L-isoleucyl)aminohexanoyl]amino-3-phenylpropionic acid To a solution of N-benzyloxycarbonyl-L-isoleucine (1114 mg) in acetonitrile (20 ml) were added N-hydroxysuccinimide (506 mg) and N,N'-dicyclohexylcarbodiimide (867 mg) at room temperature and the mixture was stirred at room temperature for 3 hours. The formed insoluble solid was filtrated off and the filtrate was added to a mixture of (S)-3-[(2S,3R,4R,5S)-5-amino-2,3,4, 6-tetrahydroxyhexanoyl]amino-3-phenylpropionic acid (compound 5) (1369 mg) and triethylamine (0.558 ml) in dimethylformamide (100 ml). The mixture was stirred at room temperature for 96 hours and concentrated under reduced pressure. The residue was dissolved in methanol (20 ml) and stirred at room temperature with 10% palladium on activated carbon (1.0 g) under hydrogen atmosphere for 24 hours. After addition of 1N hydrochloric acid, the whole was filtrated and the filtrate was concentrated under reduced pressure. The residue was passed through a column of DIAION HP-20SS (Mitsubishi kasei corporation), followed by elution with water-acetonitrile. The effective fractions were combined and concentrated under reduced pressure. The residue was recrystallized from methanol-diethylether to afford the title compound (199 mg).

$^1$H-NMR(DMSO-$d_6$) δ: 0.70–0.95(6H,m), 1.20–1.90(3H, m), 2.50–3.00(2H,m), 3.10–4.20(7H,m), 5.10–5.30(1H, m), 7.10–7.40(5H,m), 7.90(1H,d,J=8.0 Hz), 8.30(1H,d,J=8.0 Hz).

EXAMPLE 29 diphenylmethyl (S)-3-[(2S,3R,4R,5S)-2,3,4,6-tetraacetoxy-5-(N-benzyloxycarbonyl-L-leucyl)aminohexanoyl]amino-3-phenylpropionate To a solution of diphenylmethyl (S)-3-[(2S,3R,4R,5S)-5-(N-benzyloxycarbonyl-L-leucyl)amino-2,3,4,6-tetrahydroxyhexanoyl]amino-3-phenylpropionate (200 mg) in pyridine (5 ml) was added acetic anhydride (3 ml) and the mixture was stirred at room temperature for 4 days. After concentration under reduced pressure, the residue was dissolved in ethyl acetate (100 ml) and washed with 1N hydrochloric acid, saturated aqueous sodium hydrogencarbonate solution and saturated brine respectively. The organic layer was dried over anhydrous sodium sulfate and concentrated under reduced pressure. The residue was passed through silica gel column chromatography, followed by elution with ethyl acetate-hexane (1:1). The effective fractions were combined and concentrated under reduced pressure to afford the title compound (85 mg).

$^1$H-NMR(CDCl$_3$) δ: 0.93–0.95(6H,m), 1.51–1.78(3H,m), 1.87(3H,s), 1.99(3H,s), 2.07(3H,s), 2.16(3H,s), 2.81(1H,dd, J=16.1 Hz,5.6 Hz), 3.12(1H,dd,J=16.1 Hz,4.4 Hz), 3.85(1H, dd,J=11.4 Hz,6.6 Hz), 4.05(1H,dd,J=11.4 Hz,6.6 Hz), 4.49 (1H,m), 5.02(1H,m), 5.10(2H,s), 5.23(1H,d,J=1.8 Hz), 5.33 (1H,dd,J=10.0 Hz,1.8 Hz), 5.41(1H,m), 5.51(1H,m), 6.36 (1H,m), 6.76(1H,s), 7.01–7.34(21H,m).

EXAMPLE 30

(S)-3-[(2S,3R,4R,5S)-5-(L-alanyl)amino-2,3,4,6-tetrahydroxyhexanoyl]amino-3-phenylpropionic acid To a solution of N-benzyloxycarbonyl-L-alanine (234 mg) in acetonitrile (30 ml) were added N-hydroxysuccinimide (123 mg) and N,N'-dicyclohexylcarbodimide (217 mg) at room temperature and the mixture was stirred at room temperature for 3 hours. The formed insoluble solid was filtrated off and the filtrate was added to a solution of (S)-3-[(2S,3R,4R,5S)-5-amino-2,3,4,6-tetrahydroxyhexanoyl]amino-3-phenylpropionic acid (compound 5) (342 mg) and triethylamine (0.139 ml) in dimethylformamide (100 ml). The mixtue was stirred at room temperature for 20 hours and concentrated under reduced pressure. To the residue was added 1N hydrochloric acid and the whole was extracted with ethyl acetate-acetonitrile. The organic layer was washed with saturated brine and dried over anhydrous sodium sulfate. Removal of the organic solvent gave a residue, which was dissolved in methanol (30 ml) and stirred at room temperature with 10% palladium on activated carbon (200 mg) under hydrogen atmosphere for 18 hours. After filtration, the filtrate was concentrated under reduced pressure to give a residue, which was passed through a column of DIAION HP-20SS (Mitsubishi kasei corporation), followed by elution with water-acetonitrile. The effective fractions were combined and concentrated under reduced pressure. The residue was recrystallized from methanol-diethylether to afford the title compound (312 mg).

$^1$H-NMR(DMSO-$d_6$) δ: 1.20(3H,d,J=7.0 Hz), 2.60–2.80 (2H,m), 3.30–4.20(6H,m), 5.10–5.30(1H,m), 7.70–7.90(1H, m), 8.30–8.50(1H,m).

EXAMPLE 31

(S)-3-[(2S,3R,4R,5S)-2,3,4,6-tetrahydroxy-5-(L-valyl)aminohexanoyl]amino-3-phenylpropionic acid To a solution of N-benzyloxycarbonyl-L-valine (460 mg) and diphenylmethyl (S)-3-[(2S,3R,4R,5S)-5-amino-2,3,4,6-tetrahydroxyhexanoyl]amino-3-phenylpropionate (500 mg) in dimethylformamide (50 ml) were added diethyl cyanophosphonate (298 mg) and triethylamine (0.191 ml) and the whole was stirred at room temperature for 15 hours. Aftert concentration under reduced pressure, to the residue was added 0.1N hydrochloric acid (50 ml) and the whole was extracted with ethyl acetate (100 ml). The organic layer was washed with saturated aqueous sodium hydrogencarbonate solution and saturated brine respectively and dried over anhydrous sodium sulfate. Removal of the organic solvent gave a residue, which was dissolved in methanol (20 ml) and stirred at room temperature with 10% palladium on activated carbon (150 mg) under hydrogen atmosphere for 1 hour. After filtration, the filtrate was concentrated under reduced pressure to give a residue, which was passed through a column of DIAION HP-20SS (Mitsubishi kasei corporation), followed by elution with water-acetonitrile. The effective fractions were combined and concentrated under reduced pressure. The residue was recrystallized from methanol-ethyl acetate to afford the title compound (663 mg).

$^1$H-NMR(D$_2$O) δ: 0.85–1.10(6H,m), 2.10(1H,m), 2.65 (2H,d,J=6.9 Hz), 3.54–3.81(5H,m), 4.19–4.26(2H,m), 5.07 (1H,t,J=6.9 Hz), 7.24(5H,br s).

EXAMPLE 32

(S)-3-[(2S,3R,4R,5S)-5-((S)-2-aminopentanoyl)amino-2,3,4,6-tetrahydroxyhexanoyl]amino-3-phenylpropionic acid Following the same procedure as described in example 31 with (S)-2-(benzyloxycarbonylamino)pentanoic acid in place of N-benzyloxycarbonyl-L-valine, the title compound was prepared.

$^1$H-NMR(D$_2$O) δ: 0.79(3H,t,J=6.8 Hz), 1.23(2H,m), 1.73 (2H,m), 2.61(2H,d,J=7.0 Hz), 3.53–3.92(5H,m), 4.17–4.24 (2H,m), 5.06(1H,t,J=7.0 Hz), 7.17–7.23(5H,m).

EXAMPLE 33

(S)-3-[(2S,3R,4R,5S)-5-((S)-2-aminobutyryl)amino-2,3,4,6-tetrahydroxyhexanoyl]amino-3-phenylpropionic acid hydrochloride To a solution of (S)-2-(benzyloxycarbonylamino)butyric acid (500 mg) in acetonitrile (10 ml) were added N-hydroxysuccinimide (291 mg) and N,N'- dicyclohexylcarbodimide (561 mg) at room temperature and the mixture was stirred at room temperature for 3 hours. The formed insoluble solid was filtrated off and the filtrate was added to a solution of (S)-3-[(2S,3R,4R,5S)-5-amino-2,3,4,6-tetrahydroxyhexanoyl]amino-3-phenylpropionic acid (compound 5) (722 mg) and triethylamine (0.558 ml) in dimethylformamide (50 ml). The mixtute was stirred at room temperature for 18 hours and concentrated under reduced pressure. To the residue was added 1N hydrochloric acid (50 ml) and the whole was extracted with ethyl acetate-tetrahydrofuran (1:1, 50 ml×3). The organic layer was washed with saturated brine and dried over anhydrous sodium sulfate. Removal of the organic solvent gave a residue, which was dissolved in methanol (50 ml) and stirred at room temperature with 10% palladium on activated carbon (200 mg) under hydrogen atmosphere for 1 hour. After filtration, the filtrate was concentrated under reduced pressure to give a residue, which was dissolved in 0.1N hydrochloric acid (0.1 ml) and passed through a column of DIAION HP-20SS (Mitsubishi kasei corporation), followed by elution with water-acetonitrile. The effective fractions were combined and concentrated under reduced pressure. The residue was recrystallized from methanol-ethyl acetate to afford the title compound (200 mg).

$^1$H-NMR(CD$_3$OD) δ: 1.05(3H,t,J=7.6 Hz), 1.85–1.96 (2H,m), 2.74(2H,d,J=6.4 Hz), 3.68–3.91(5H,m), 4.30–4.33 (2H,m), 5.32(1H,t,J=6.4 Hz), 7.24–7.42(5H,m).

EXAMPLE 34

(S)-3-[(2S,3R,4R,5S)-2,3,4,6-tetrahydroxy-5-(L-phenylalanyl)aminohexanoyl]amino-3-phenylpropionic acid Following the same procedure as described in example 33 with N-benzyloxycarbonyl-L-phenylalanine in place of (S)-2-(benzyloxycarbonylamino)butyric acid, the title compound was prepared.

$^1$H-NMR(D$_2$O) δ: 2.59(2H,d,J=6.4 Hz), 2.94(1H,dd,J=14.0 Hz,9.0 Hz), 3.18(1H,dd,J=14.0 Hz,5.4 Hz), 3.44–3.76 (4H,m), 4.09–4.21(3H,m), 5.08(1H,t,J=6.4 Hz), 7.17–7.25 (10H,m).

EXAMPLE 35

(S)-3-[(2S,3R,4R,5S)-5-((S)-3-acetylamino-2-aminopropionyl)amino-2,3,4,6-tetrahydroxyhexanoyl]amino-3-phenylpropionic acid Following the same procedure as described in example 33 with (S)-3-acetylamino-2-(benzyloxycarbonylamino) propionic acid in place of (S)-2-(benzyloxycarbonylamino) butyric acid, the title compound was prepared.

$^1$H-NMR(D$_2$O) δ: 1.87(3H,s), 2.58(2H,d,J=7.0 Hz), 3.36–3.79(6H,m), 4.04(1H,m), 4.16–4.24(2H,m), 5.08(1H, t,J=7.0 Hz), 7.23(5H,br s).

EXAMPLE 36

(S)-3-[(2S,3R,4R,5S)-2,3,4,6-tetrahydroxy-5-(L-prolyl)aminohexanoyl]amino-3-phenylpropionic acid Following the same procedure as described in example 33 with N-benzyloxycarbony-L-proline in place of (S)-2-(benzyloxycarbonylamino)butyric acid, the title compound was prepared.

3H-NMR(D$_2$O) δ: 1.85–1.98(3H,m), 2.34(1H,m), 2.58 (2H,d,J=7.0 Hz), 3.16–3.32(2H,m), 3.48–3.77(4H,m), 4.18–4.30(3H,m), 5.06(1H,t,J=7.0 Hz), 7.21–7.26(5H,m).

EXAMPLE 37

(S)-3-[(2S,3R,4R,5S)-5-((S)-2-amino-5,5,5-trifluoropentanoyl)amino-2,3,4,6-tetrahydroxyhexanoyl]amino-3-phenylpropionic acid Following the same procedure as described in example 33 with (S)-2-benzyloxycarbonylamino-5,5,5-trifluropentanoic acid in place of (S)-2-(benzyloxycarbonyl)aminobutyric acid, the title compound was prepared.

$^1$H-NMR(D2O) δ: 1.95–2.30(4H,m), 2.58(2H,d,J=6.8 Hz), 3.49–3.78(4H,m), 3.98(1H,t,J=8.4 Hz), 4.18–4.24(2H, m), 5.06(1H,t,J=6.8 Hz), 7.21–7.24(5H,m).

EXAMPLE 38

(S)-3-[(2S,3R,4R,5S)-5-((S)-2-amino-4,4,4-trifluorobutyryl)amino-2,3,4,6-tetrahydroxyhexanoyl]amino-3-phenylpropionic acid Following the same procedure as described in example 33 with (S)-2-benzyloxycarbonylamino-4,4,4-triflurobutyric acid in place of (S)-2-(benzyloxycarbonylamino)butyric acid, the title compound was prepared.

$^1$H-NMR(D$_2$O) δ: 2.74(2H,d,J=6.8 Hz), 2.87–2.99(2H, m), 3.64–3.98(4H,m), 4.34–4.41(3H,m), 5.21(1H,t,J=6.8 Hz), 7.30–7.60(5H,m).

EXAMPLE 39

(S)-3-[(2S,3R,4R,5S)-5-((S)-2-amino-3-(methanesulfonylamino)propionyl)amino-2,3,4,6-tetrahydroxyhexanoyl]amino-3-phenylpropionic acid Following the same procedure as described in example 33 with (S)-2-benzyloxycarbonylamino-3-(methnesulfonylamino)propionic acid in place of (S)-2-(benzyloxycarbonylamino)butyric acid, the title compound was prepared.

$^1$H-NMR(D$_2$O) δ: 2.70(2H,d,J=7.0 Hz), 3.06(3H,s), 3.54–3.89(6H,m), 4.17(1H,t,J=6.6 Hz), 4.28–4.35(2H,m), 5.18(1H,t,J=7.0 Hz), 7.20–7.36(5H,m).

EXAMPLE 40

(S)-$^3$-[(2S,3R,4R,5S)-5-((S)-2-amino-5-fluoropentanoyl)amino-2,3,4,6-tetrahydroxyhexanoyl]amino-3-phenylpropionic acid Following the same procedure as described in example 33 with (S)-2-benzyloxycarbonylamino-5-fluropentanoic acid in place of (S)-2-(benzyloxycarbonylamino)butyric acid, the title compound was prepared.

$^1$H-NMR(D$_2$O) δ: 1.80–2.15(3H,m), 2.30–2.55(1H,m), 2.69(2H,d,J=6.6 Hz), 3.33–3.42(2H,m), 3.60–3.87(4H,m), 4.28–4.40(3H,m), 5.17(1H,t,J=6.6 Hz), 7.32–7.34(5H,m).

EXAMPLE 41

(S)-3-[(2S,3R,4R,5S)-5-((S)-2-amino-3-(formylamino)propionyl)amino-2,3,4,6-tetrahydroxyhexanoyl]amino-3-phenylpropionic acid Following the same procedure as described in example 33 with (S)-2-benzyloxycarbonylamino-3-(formylamino) propionic acid in place of (S)-2-(benzyloxycarbonylamino) butyric acid, the title compound was prepared.

$^1$H-NMR(D$_2$O) δ: 2.70(2H,d,J=7.0 Hz), 3.59–3.98(7H, m), 4.17–4.33(2H,m), 5.19(1H,t,J=7.0 Hz), 7.33–7.35(5H, m), 8.11(1H,s).

EXAMPLE 42 diphenylmethyl (S)-3-[(2S,3R,4R,5S)-5-(N-tert-butoxycarbonyl-O-(4-methoxybenzyl)-L-homoseryl) amino-2,3,4,6-tetrahydroxyhexanoyl]amino-3-phenylpropionate Following the same procedure as described in example 25 with N-tert-butoxycarbonyl-O-(4-methoxybenzyl)-L-homoserine in place of O-tert-butyl-N-fluorenylmethyloxycarbonyl-L-serine, the title compound was prepared.

$^1$H-NMR(DMSO-d$_6$) δ: 1.37(9H,s), 1.60–2.10(2H,m), 3.05(2H,d,J=6.6 Hz), 3.20–5.40(12H,m), 3.73(3H,s), 6.67 (1H,s), 6.80–7.40(19H,m).

EXAMPLE 43

(S)-3-[(2S,3R,4R,5S)-5-(L-homoseryl)amino-2,3,4,6-tetrahydroxyhexanoyl]amino-3-phenylpropionic acid To diphenylmethyl (S)-3-[(2S,3R,4R,5S)-5-(N-tert-butoxycarbonyl-O-(4-methoxybenzyl)-L-homoseryl)amino-2,3,4,6-tetrahydroxyhexanoyl]amino-3-phenylpropionate (200 mg) was added 4N hydrogen chloride in ethyl acetate (10 ml) at room temperature and the mixture was stirred at room temperature for 3 hours. After concentration under reduced pressure, the residue was dissolved in water and washed with diethylether. The aqueous layer was passed through a column of DIAION CHP-20P (Mitsubishi kasei corporation), followed by elution with water-acetonitrile. The effective fractions were combined and concentrated under reduced pressure. The residue was recrystallized from methanol-diethylether to afford the title compound (53 mg).

$^1$H-NMR(DMSO-d$_6$) δ: 1.40–2.00(2H,m), 2.55–2.80(2H, m), 3.00–5.30(9H,m), 7.10–7.40(5H,m).

EXAMPLE 44

(S)-3-[(2S,3R,4R,5S)-5-((S)-2-amino-3-cyanopropionyl)amino-2,3,4,6-tetrahydroxyhexanoyl]amino-3-phenylpropionic acid To a solution of (S)-2-benzyloxycarbonylamino-3-cyanopropionic acid (300 mg) in acetonitrile (10 ml) were added N-hydroxysuccinimide (177 mg) and N,N'-dicyclohexylcarbodiimide (303 mg) at room temperature and the mixture was stirred at room temperature for 2 hours. The formed insoluble solid was filtrated off and the filtrate was added to a solution of (S)-3-[(2S,3R,4R,5S)-5-amino-2,3,4,6-tetrahydroxyhexanoyl]amino-3-phenylpropionic acid (compound 5) (503 mg) and triethylamine (0.410 ml) in dimethylformamide (30 ml) at room temperature. The mixture was stirred at room temperature for 18 hours, followed by concentration under reduced pressure. To the residue was added 1N hydrochloric acid (50 ml) and the whole was extracted with ethyl acetate,(100 ml×2). The extract was washed with saturated brine and dried over anhydrous sodium sulfate. Removal of the organic solvent gave a residue, which was dissolved in 4N hydrogen chloride solution in ethyl acetate (20 ml) and stirred at room temperature for 1 hour. After concentration, the residue was passed through a column of DIAION HP-20SS (Mitsubishi kasei corporation), followed by elution with water-acetonitrile. The effective fractions were combined and concentrated under reduced pressure. The residue was recrystallized from methanol-ethyl acetate to afford the title compound (75 mg).

$^1$H-NMR(D$_2$O) δ: 2.60(2H,d,J=6.4 Hz), 3.48–3.79(4H, m), 4.13–4.26(3H,m), 5.18(1H,t,J=6.4 Hz), 7.15–7.35(5H, m).

EXAMPLE 45

(S)-3-[(2S,3R,4R,5S)-2,3,4,6-tetrahydroxy-5-(L-methionyl)aminohexanoyl]amino-3-phenylpropionic acid To a solution of N-tert-butoxycarbonyl-L-methionine (260 mg) in acetonitrile (15 ml) were added N-hydroxysuccinimide (132 mg) and N,N'-dicyclohexylcarbodiimide (227 mg) at room temperature and the mixture was stirred at room temperature for 3 hours. The formed insoluble solid was filtrated off and to the filtrate was added (S)-3-[(2S,3R,4R,5S)-5-amino-2,3,4,6-tetrahydroxyhexanoyl]amino-3-phenylpropionic acid (compound 5) (356 mg), triethylamine (0.217 ml) and dimethylformamide (50 ml) at room temperature. The mixture was stirred at room temperature for 20 hours, followed by concentration under reduced pressure. To the residue was added 4N hydrogen chloride solution in ethyl acetate (30 ml) and the whole was stirred at room temperature for 1.5 hours. After concentration, the residue was passed through a column of DIAION HP-20SS (Mitsubishi kasei corporation), followed by elution with water-acetonitrile. The effective fractions were combined and concentrated under reduced pressure. The residue was recrystallized from methanol-diethylether to afford the title compound (310 mg).

$^1$H-NMR(D$_2$O) δ: 2.12(3H,s), 2.20(2H,m), 2.62(2H,t,J= 7.3 Hz), 2.74(1H,d,J=6.9 Hz), 3.60–3.94(4H,m), 4.16(1H,t, J=6.7 Hz), 4.33–4.40(2H,m), 5.20(1H,t,J=6.9 Hz), 7.30–7.48(5H,m).

EXAMPLE 46

(S)-3-[(2S,3R,4R,5S)-2,3,4,6-tetrahydroxy-5-(S-methyl-L-cysteinyl)aminohexanoyl]amino-3-phenylpropionic acid Following the same procedure as described in example 45 with N-tert-butoxycarbonyl-S-methyl-L-cysteine in place of N-tert-butoxycarbonyl-L-methionine, the title compound was prepared.

$^1$H-NMR(DMSO-d$_6$) δ: 2.05(3H,s), 2.56–2.86(4H,m), 3.40–3.80(11H,m), 4.05(1H,m), 4.13(1H,s), 5.22(1H,m), 7.19–7.37(5H,m), 7.84(1H,d,J=8.8 Hz), 8.24(1H,d,J=8.8 Hz).

EXAMPLE 47

(S)-3-[(2S,3R,4R,5S)-5-((S)-2-amino-4-pentenoyl) amino-2,3,4,6-tetrahydroxyhexanoyl]amino-3-phenylpropionic acid To a solution of (S)-2-tert-butoxycarbonylamino-4-pentenoic acid (220 mg) in acetonitrile (7.5 ml) were added N-hydroxysuccinimide (118 mg) and N,N'-dicyclohexylcarbodiimide (210 mg) at room temperature and the mixture was stirred at room temperature for 2.5 hours. The formed insoluble solid was filtrated off and to the filtrate was added (S)-3-[(2S,3R,4R,5S)-5-amino-2,3,4,6-tetrahydroxyhexanoyl]amino-3-phenylpropionic acid (compound 5) (342 mg), triethylamine (0.28 ml) and dimethylformamide (40 ml) at room temperature. The mixture was stirred at room temperature for 2 days, followed by concentration under reduced pressure. To the residue was added 4N hydrogen chloride solution in ethyl acetate (20 ml)

and the whole was stirred at room temperature for 2 hours. After concentration under reduced pressure, the residue was passed through a column of DIAION HP-20SS (Mitsubishi kasei corporation), followed by elution with water-acetonitrile. The effective fractions were combined and concentrated under reduced pressure, followed by lyophilization. The residue was passed a column of Sephadek LH-20 (Pharmacia, Sweden), followed by elution with water. The effective fractions were combined and concentrated under reduced pressure. The residue was recrystallized from methanol-ethyl acetate to afford the title compound (57 mg).

$^1$H-NMR($D_2O$) δ: 2.64–2.76(4H,m), 3.62–3.82(2H,m), 3.89(1H,d,J=9.8 Hz), 4.12(1H,m), 4.35(2H,m), 5.20(1H,t,J=6.8 Hz), 5.25–5.35(2H,m), 5.77(1H,m), 7.30–7.46(5H,m).

EXAMPLE 48

(S)-3-[(2S,3R,4R,5S)-5-(L-alanyl-L-leucyl)amino-2,3,4,6-tetrahydroxyhexanoyl]amino-3-phenylpropionic acid To a solution of N-benzyloxycarbonyl-L-alanine (50 mg) in acetonitrile (2 ml) were added N-hydroxy-5-norbornene-2,3-dicarboxyimide (47 mg) and N,N'-dicyclohexylcarbodimide (51 mg) and the mixture was stirred at room temperature for 1 hour. The formed insoluble solid was filtrated off and the filtrate was added to a solution of (S)-3-[(2S,3R,4R,5S)-2,3,4,6-tetrahydroxy-5-(L-leucyl) aminohexanoyl]amino-3-phenylpropionic acid (compound 3) (100 mg) and triethylamine (0.031 ml) in dimethylformamide (10 ml). The mixture was stirred at room temperature for 16 hours and concentrated under reduced pressure. To the residue was added 1N hydrochloric acid (0.956 ml) and the whole was extracted with ethyl acetate. The organic layer was washed with saturated brine and dried over anhydrous sodium sulfate. Removal of the organic solvent gave a residue, which was dissolved in methanol (10 ml) and stirred at room temperature with 10% palladium on activated carbon (50 mg) under hydrogen atmosphere for 1 hour. After filtration, the filtrate was concentrated under reduced pressure to give a residue, which was passed through a column of DIAION HP-20SS (Mitsubishi kasei corporation), followed by elution with water-acetonitrile. The effective fractions were combined and concentrated under reduced pressure. The residue was recrystallized from methanol-ethyl acetate to afford the title compound (75 mg).

$^1$H-NMR($CD_3OD$) δ: 0.93–1.00(6H,m), 1.55(3H,d,J=7.4 Hz), 1.60–1.80(3H,m), 2.68(2H,d,J=6.6 Hz), 3.65–3.72(3H,m), 3.86–3.93(2H,m), 4.15–4.36(3H,m), 5.31(1H,t,J=6.6 Hz), 7.22–7.41(5H,m).

EXAMPLE 49

(S)-3-[(2S,3R,4R,5S)-2,3,4,6-tetrahydroxy-5-(N-methylglycyl-L-leucyl)aminohexanoyl]amino-3-phenylpropionic acid Following the same procedure as described in example 48 with N-benzyloxycarbonyl-N-methylglycine in place of N-benzyloxycarbonyl-L-alanine, the title compound was prepared.

$^1$H-NMR($CD_3OD$) δ: 0.94(3H,d,J=5.8 Hz), 0.98(3H,d,J=3.2 Hz), 1.60–1.80(3H,m), 2.63(2H,d,J=6.2 Hz), 2.72(3H,s), 3.66–3.76(3H,m), 3.83–3.85(3H,m), 4.14(1H,t,J=6.2 Hz), 4.27–4.35(2H,m), 5.32(1H,t,J=6.2 Hz), 7.20–7.40(5H,m).

EXAMPLE 50

(S)-3-[(2S,3R,4R,5S)- 2,3,4,6-tetrahydroxy-5-(L-phenylalanyl-L-leucyl)aminohexanoyl]amino-3-phenylpropionic acid Following the same procedure as described in example 48 with N-benzyloxycarbonyl-L-phenylalanine in place of N-benzyloxycarbonyl-L-alanine, the title compound was prepared.

$^1$H-NMR($CD_3OD$) δ: 0.94(3H,d,J=6.4 Hz), 0.97(3H,d,J=7.8 Hz), 1.60–1.80(3H,m), 2.72(2H,d,J=6.6 Hz), 3.05(1H,dd,J=14.4 Hz,8.0 Hz), 3.30(1H,dd,J=14.4 Hz,4.2 Hz), 3.66–3.78(3H,m), 3.91(1H,m), 4.02(1H,m), 4.22(1H,t,J=6.6 Hz), 4.30–4.36(2H,m), 5.33(1H,t,J=6.6 Hz), 7.20–7.39 (10H,m).

EXAMPLE 51

(S)-3-[(2S,3R,4R,5S)-2,3,4,6-tetrahydroxy-5-(L-lysyl-L-leucyl)aminohexanoyl]amino-3-phenylpropionic acid dihydrochloride To a solution of $N^\alpha$-benzyloxycarbonyl-$N^\epsilon$-tert-butoxycarbonyl-L-lysine (126 mg) in acetonitrile (3 ml) were added N-hydroxy-5-norbornene-2,3-dicarboxyimide (64 mg) and N,N'-dicyclohexylcarbodiimide (69 mg) and the mixture was stirred at room temperature for 1 hour. The formed insoluble solid was filtrated off and the filtrate was added to a solution of (S)-3-[(2S,3R,4R,5S)-2,3,4,6-tetrahydroxy-5-(L-leucyl)aminohexanoyl]amino-3-phenylpropionic acid (compound 3) (150 mg) and triethylamine (0.042 ml) in dimethylformamide (14 ml) at room temperature. The mixture was stirred at room temperature for 16 hours, followed by concentration under reduced pressure. To the residue was added 1N hydrochloric acid (1.3 ml) and the whole was extracted with ethyl acetate. The extract was washed with saturated brine and dried over anhydrous sodium sulfate. Removal of the organic solvent gave a residue, which was dissolved in methanol (20 ml) and stirred at room temperature with 10% palladium on activated carbon (100 mg) under hydrogen atmosphere for 2 hours. After filtration, the filtrate was concentrated under reduced pressure to give a residue, which was dissolved in 4N hydrogen chloride solution in ethyl acetate (10 ml) and stirred at room temperature for 2 hours. After concentration, the residue was passed through a column of DIAION HP-20SS (Mitsubishi kasei corporation), followed by elution with water-acetonitrile. The effective fractions were combined and concentrated under reduced pressure. The residue was recrystallized from methanol-ethyl acetate to afford the title compound (180 mg).

$^1$H-NMR($CD_3OD$) δ: 0.97(3H,d,J=6.0 Hz), 1.00(3H,d,J=6.0 Hz), 1.40–2.00(10H,m), 2.74(1H,m), 2.93–2.99(2H,m), 3.61–3.73(3H,m), 3.84–4.00(2H,m), 4.22–4.46(3H,m), 5.37 (1H,m), 7.23–7.41(5H,m).

EXAMPLE 52

(S)-3-[(2S,3R,4R,5S)-5-(α-L-glutamyl-L-leucyl) amino-2,3,4,6-tetrahydroxyhexanoyl]amino-3-phenylpropionic acid To a solution of N-benzyloxycarbonyl-L-glutamic acid γ-tert-butyl ester (101 mg) in acetonitrile (3 ml) were added N-hydroxy-5-norbornene-2,3-dicarboxyimide (64 mg) and N,N'-dicyclohexylcarbodiimide (69 mg) and the mixture was stirred at room temperature for 1 hour. The formed insoluble solid was filtrated off and the filtrate was added to a solution of (S)-3-[(2S,3R,4R,5S)-2,3,4,6-tetrahydroxy-5-(L-leucyl) aminohexanoyl]amino-3-phenylpropionic acid (compound 3) (150 mg) and triethylamine (0.042 ml) in dimethylformamide (14 ml) at room temperature. The mixture was stirred at room temperature for 16 hours, followed by concentration under reduced pressure. To the residue was added 1N hydrochloric acid (1.3 ml) and the whole was extracted with ethyl acetate. The extract was washed with saturated brine and dried over anhydrous sodium sulfate.

Removal of the organic solvent gave a residue, which was dissolved in methanol (20 ml) and stirred at room temperature with 10% palladium on activated carbon (100 mg) under hydrogen atmosphere for 2 hours. After filtration, the filtrate was concentrated under reduced pressure to give a residue, which was dissolved in trifluoroacetic acid (20 ml) and stirred at room temperature for 1 hour. After concentration, the residue was passed through a column of DIAION HP-20SS (Mitsubishi kasei corporation), followed by elution with water-acetonitrile. The effective fractions were combined and concentrated under reduced pressure. The residue was recrystallized from methanol-ethyl acetate to afford the title compound (124 mg).

$^1$H-NMR(CD$_3$OD) δ: 0.70(3H,d,J=6.2 Hz), 0.74(3H,d,J=8.0 Hz), 1.38–1.60(3H,m), 1.70–2.05(2H,m), 2.21–2.35(2H,m), 2.40–2.64(2H,m), 3.44–3.47(3H,m), 3.63–3.68(2H,m), 3.97(1H,t,J=7.6 Hz), 4.09–4.15(2H,m), 5.12(1H,m), 6.98–7.17(5H,m).

EXAMPLE 53

(S)-3-[(2S,3R,4R,5S)-5-(N-(4-aminobutyryl)-L-leucyl)amino-2,3,4,,6-tetrahydroxyhexanoyl]amino-3-phenylpropionic acid To a solution of 4-(benzyloxycarbonylamino)butyric acid (78 mg) in acetonitrile (10 ml) were added N-hydroxysuccinimide (41 mg) and N,N'-dicyclohexylcarbodimide (71 mg) and the mixture was stirred at room temperature for 3 hours. The formed insoluble solid was filtrated off and the filtrate was added to a solution of (S)-3-[(2S,3R,4R,5S)-2,3,4,6-tetrahydroxy-5-(L-leucyl)aminohexanoyl]amino-3-phenylpropionic acid (compound 3) (150 mg) and triethylamine (0.115 ml) in dimethylformamide (30 ml). The mixture was stirred at room temperature for 2 days and concentrated under reduced pressure. To the residue was added 1N hydrochloric acid (50 ml) and the whole was extracted with ethyl acetate. The organic layer was washed with saturated brine and dried over anhydrous sodium sulfate. Removal of the organic solvent gave a residue, which was dissolved in methanol (30ml) and stirred at room temperature with 10% palladium on activated carbon (70 mg) under hydrogen atmosphere for 1 hour. After filtration, the filtrate was concentrated under reduced pressure to give a residue, which was passed through a column of DIAION HP-20SS (Mitsubishi kasei corporation), followed by elution with water-acetonitrile. The effective fractions were combined and concentrated under reduced pressure. The residue was recrystallized from methanol-ethyl acetate to afford the title compound (130 mg).

$^1$H-NMR(CD$_3$OD) δ: 0.92(3H,d,J=5.8 Hz), 0.96(3H,d,J=6.0 Hz), 1.61–1.80(3H,m), 1.91–2.01(2H,m), 2.32(1H,m), 2.46(1H,q,J=5.8 Hz), 2.65(2H,d,J=7.0 Hz), 2.92–3.04(2H,m), 3.66–3.78(3H,m), 3,89(2H,d,J=9.6 Hz), 4.15(1H,t,J=6.2 Hz), 4.29(2H,m), 5.32(1H,t,J=7.0 Hz), 7.20–7.40(5H,m).

EXAMPLE 54

(S)-3-[(2S,3R,4R,5S)-2,3,4,6-tetrahydroxy-5-(L-ornithyl-L-leucyl)aminohexanoyl]amino-3-phenylpropionic acid Following the same procedure as described in example 53 with N$^α$,N$^δ$-bisbenzyloxycarbonyl-L-ornithine in place of 4-(benzyloxycarbonylamino)butyric acid, the title compound was prepared.

$^1$H-NMR(CD$_3$OD) δ: 0.92–0.98(6H,m), 1.63–1.72(7H,m), 2.65(2H,d,J=6.6 Hz), 2.90–2.92(2H,m), 3.44(1H,m), 3.65–3.75(3H,m), 3.88(1H,dd,J=9.8 Hz,1.8 Hz), 4.19(1H,dt, J=6.2 Hz,1.8 Hz), 4.31(1H,d,J=1.2 Hz), 4.45(1H,t,J=7.4 Hz), 5.32(1H,t,J=6.6 Hz), 7.20–7.41(5H,m).

EXAMPLE 55

(S)-3-[(2S,3R,4R,5S)-5-(L-asparaginyl-L-leucyl)amino-2,3,4,6-tetrahydroxyhexanoyl]amino-3-phenylpropionic acid Following the same procedure as described in example 53 with N-benzyloxycarbonyl-L-asparagine in place of 4-(benzyloxycarbonylamino)butyric acid, the title compound was prepared.

$^1$H-NMR(CD$_3$OD) δ: 0.92–0.99(6H,m), 1.60–1.80(3H,m), 2.69(2H,d,J=7.0 Hz), 2.80(1H,dd,J=16.8 Hz,7.4 Hz), 2.95(1H,dd,J=16.8 Hz,5.2 Hz), 3.67–3.75(3H,m), 3.88(1H,m), 4.07–4.22(2H,m), 4.30–4.40(2H,m), 5.53(1H,t,J=7.0 Hz), 7.20–7.41(5H,m).

EXAMPLE 56

(S)-3-[(2S,3R,4R,5S)-5-(L-glutaminyl-L-leucyl)amino-2,3,4,6-tetrahydroxyhexanoyl]amino-3-phenylpropionic acid Following the same procedure as described in example 53 with N-benzyloxycarbonyl-L-glutamine in place of 4-(benzyloxycarbonylamino)butyric acid, the title compound was prepared.

$^1$H-NMR(CD$_3$OD) δ: 0.93–1.02(6H,m), 1.60–1.80(3H,m), 2.10–2.20(2H,m), 2.48–2.60(2H,m), 2.91–2.98(2H,m), 3.68–4.55(8H,m), 5.42(1H,m), 7.29–7.37(5H,m).

EXAMPLE 57

(S)-3-[(2S,3R,4R,5S)-5-(N-((S)-3-acetylamino-2-aminopropionyl)-L-leucyl)amino-2,3,4,6-tetrahydroxyhexanoyl]amino-3-phenylpropionic acid Following the same procedure as described in example 53 with (S)-3-acetylamino-2-(benzyloxycarbonylamino)propionic acid in place of 4-(benzyloxycarbonylamino)butyric acid, the title compound was prepared.

$^1$H-NMR(CD$_3$OD) δ: 0.93–1.00(6H,m), 1.64–1.70(3H,m), 1.98(3H,s), 2.70(2H,d,J=6.8 Hz), 3.51–3.98(7H,m), 4.21–4.41(3H,m), 5.33(1H,t,J=6.8 Hz), 7.20–7.43(5H,m).

EXAMPLE 58

(S)-3-[(2S,3R,4R,5S)-5-(N-((S)-2,3-diaminopropionyl)-L-leucyl)amino-2,3,4,6-tetrahydroxyhexanoyl]amino-3-phenylpropionic acid Following the same procedure as described in example 53 with (S)-2,3-(bisbenzyloxycarbonylamino)propionic acid in place of 4-(benzyloxycarbonylamino)butyric acid, the title compound was prepared.

$^1$H-NMR(D$_2$O) δ: 0.74–0.81(6H,m), 1.40–1.65(3H,m), 2.59(2H,d,J=7.0 Hz), 2.98(1H,dd,J=15.2 Hz,7.6 Hz), 3.15 (1H,dd,J=15.2 Hz,5.8 Hz), 3.46–3.78(5H,m), 4.09–4.30(3H,m), 5.06(1H,t,J=7.0 Hz), 7.18–7.27(5H,m).

EXAMPLE 59

(S)-3-[(2S,3R,4R,5S)-2,3,4,6-tetrahydroxy-5-((O-methyl-L-threonyl)-L-leucyl)aminohexanoyl]amino-3-phenylpropionic acid Following the same procedure as described in example 53 with N-benzyloxycarbonyl-O-methyl-L-threonine in place of 4-(benzyloxycarbonylamino)butyric acid, the title compound was prepared.

$^1$H-NMR(CD$_3$OD) δ: 0.94–1.01(6H,m), 1.15(3H,d,J=6.6 Hz), 1.62–1.73(3H,m), 2.75–3.00(2H,m), 3.43(3H,s), 3.60–3.74(4H,m), 3.88–3.94(2H,m), 4.12–4.22(2H,m), 4.33 (1H,s), 5.37(1H,t,J=6.2 Hz), 7.32–7.38(5H,m).

EXAMPLE 60

(S)-3-[(2S,3R,4R,5S)-5-(N-((S)-2-amino-3-cyclohexylpropionyl)-L-leucyl)amino-2,3,4,6-tetrahydroxyhexanoyl]amino-3-phenylpropionic acid Following the same procedure as described in example 53 with (S)-2-benzyloxycarbonylamino-3-cyclohexylpropionic acid in place of 4-(benzyloxycarbonylamino)butyric acid, the title compound was prepared.

$^1$H-NMR(D$_2$O) δ: 0.77–1.13(1H,m), 1.50(11H,m), 2.58 (2H,d,J=5.8 Hz), 3.54–4.22(8H,m), 5.05(1H,t,J=5.8 Hz), 7.23(5H,br s).

EXAMPLE 61

(S)-3-[(2S,3R,4R,5S)-5-(N-((S)-2-amino-5,5,5-trifluoropentanoyl)-L-leucyl)amino-2,3,4,6-tetrahydroxyhexanoyl]amino-3-phenylpropionic acid Following the same procedure as described in example 53 with (S)-2-benzyloxycarbonylamino-5,5,5-trifluoropentanoic acid in place of 4-(benzyloxycarbonylamino)butyric acid, the title compound was prepared.

$^1$H-NMR(D$_2$O) δ: 0.75–0.81(6H,m), 1.42–1.60(3H,m), 1.98–2.22(4H,m), 2.59(2H,d,J=6.6 Hz), 3.43–3.59(3H,m), 3.73–3.95(2H,m), 4.08–4.36(3H,m), 5.06(1H,t,J=6.6 Hz), 7.15–7.35(5H m).

EXAMPLE 62

(S)-3-[(2S,3R,4R,5S)-2,3,4,6-tetrahydroxy-5-((L-leucyl-L-leucyl)aminohexanoyl]amino-3-phenylpropionic acid Following the same procedure as described in example 53 with N-benzyloxycarbonyl-L-leucine in place of 4-(benzyloxycarbonylamino)butyric acid, the title compound was prepared.

$^1$H-NMR(CD$_3$OD) δ: 0.80–1.00(12H,m), 1.00–1.90(6H, m), 2.60–2.80(2H,m), 3.20–5.30(9H,m), 7.10–7.60(5H,m).

EXAMPLE 63

(S)-3-[(2S,3R,4R,5S)-2,3,4,6-tetrahydroxy-5-(L-isoleucyl-L-leucyl)aminohexanoyl]amino-3-phenylpropionic acid Following the same procedure as described in example 53 with N-benzyloxycarbonyl-L-isoleucine in place of 4-(benzyloxycarbonylamino)butyric acid, the title compound was prepared.

$^1$H-NMR(CD$_3$OD) δ: 0.70–1.80(18H,m), 2.60–2.90(2H, m), 3.00–5.30(9H,m), 7.10–7.50(5H,m).

EXAMPLE 64

(S)-3-[(2S,3R,4R,5S)-2,3,4,6-tetrahydroxy-5-((O-methyl-L-seryl)-L-leucyl)aminohexanoyl]amino-3-phenylpropionic acid Following the same procedure as described in example 53 with N-benzyloxycarbonyl-O-methyl-L-serine in place of 4-(benzyloxycarbonylamino)butyric acid, the title compound was prepared.

$^1$H-NMR(DMSO-d$_6$) δ: 0.85(3H,d,J=6.0 Hz), 0.88(3H,d, J=6.0 Hz), 1.40–1.70(3H,m), 2.70–2.80(2H,m), 3.25(3H,s), 3.10–5.30(10H,m), 7.10–7.60(5H,m), 8.00–8.40(2H,m).

EXAMPLE 65

(S)-3-[(2S,3R,4R,5S)-2,3,4,6-tetrahydroxy-5-(N-(2-phenylglycyl)-L-leucyl)aminohexanoyl]amino-3-phenylpropionic acid Following the same procedure as described in example 53 with N-benzyloxycarbonyl-2-phenylglycine in place of 4-(benzyloxycarbonylamino)butyric acid, the title compound was prepared.

$^1$H-NMR(CD30D,) δ: 0.70–1.00(6H,m), 1.50–1.70(3H, m), 2.60–2.80(2H,m), 3.40–5.50(9H,m), 7.10–7.60(10H,m).

EXAMPLE 66

(S)-3-[(2S,3R,4R,5S)-2,3,4,6-tetrahydroxy-5-((N-methyl-L-valyl)-L-leucyl)aminohexanoyl]amino-3-phenylpropionic acid Following the same procedure as described in example 53 with N-benzyloxycarbonyl-N-methyl-L-valine in place of 4-(benzyloxycarbonylamino)butyric acid, the title compound was prepared.

$^1$H-NMR(DMSO-d$_6$) δ: 0.70–1.00(12H,m), 1.40–1.90 (4H,m), 2.19(3H,s), 2.50–5.30(11H,m), 7.10–7.50(6H,m), 8.03(1H,d,J=9.2 Hz), 8.–20(1H,d,J=8.8 Hz).

EXAMPLE 67

(S)-3-[(2S,3R,4R,5S)-5-(N-((S)-2-aminobutyryl)-L-leucyl)amino-2,3,4,6-tetrahydroxyhexanoyl]amino-3-phenylpropionic acid hydrochloride To a solution of (S)-2-(tert-butoxycarbonylamino)butyric acid (70 mg) in acetonitrile (10 ml) were added N-hydroxysuccinimide (41 mg) and N,N'-dicyclohexylcarbodimide (71 mg) and the mixture was stirred at room temperature for 3 hours. The formed insoluble solid was filtrated off and the filtrate was added to a solution of (S)-3-[(2S,3R,4R,5S)-2,3,4,6-tetrahydroxy-5-(L-leucyl)aminohexanoyl]amino-3-phenylpropionic acid (compound 3) (150 mg) and triethylamine (0.115 ml) in dimethylformamide (30 ml) at room temperature. The mixture was stirred at room temperature for 2 days, followed by concentration under reduced pressure. To the residue was added 1N hydrochloric acid (50 ml) and the whole was extracted with ethyl acetate. The extract was washed with saturated brine and dried over anhydrous sodium sulfate. Removal of the organic solvent gave a residue, which was dissolved in 4N hydrogen chloride solution in ethyl acetate (10 ml) and stirred at room temperature for 2 hours. After concentration, the residue was passed through a column of DIAION HP-20SS (Mitsubishi kasei corporation), followed by elution with water-acetonitrile. The effective fractions were combined and concentrated under reduced pressure. The residue was recrystallized from methanol-ethyl acetate to afford the title compound (108 mg).

$^1$H-NMR(CD$_3$OD) δ: 0.94–1.09(9H,m), 1.62–1.72(3H, m), 1.84–1.98(2H,m), 2.69(2H,d,J=6.4 Hz), 3.68–3.83(3H, m), 4.19–4.43(5H,m), 5.32(1H,t,J=6.4 Hz), 7.22–7.43(5H, m).

EXAMPLE 68

(S)-3-[(2S,3R,4R,5S)-2,3,4,6-tetrahydroxy-5-(L-norvalyl-L-leucyl)aminohexanoyl]amino-3-phenylpropionic acid hydrochloride Following the same procedure as described in, example 67 with N-tert-butoxycarbonyl-L-norvaline in place of (S)-

2-(tert-butoxycarbonylamino)butyric acid, the title compound was prepared.

$^1$H-NMR(CD$_3$OD) δ: 0.93–1.02(9H,m), 1.44–1.52(2H, m), 1.62–1.74(3H,m), 1.81–1.90(2H,m), 2.69(2H,d,J=6.2 Hz), 3.68–3.83(3H,m), 4.18–4.47(5H,m), 5.32(1H,t,J=6.2 Hz), 7.19–7.43(5H,m).

EXAMPLE 69

(S)-3-[(2S,3R,4R,5S)-2,3,4,6-tetrahydroxy-5-(L-norleucyl-L-leucyl)aminohexanoyl]amino-3-phenylpropionic acid hydrochloride Following the same procedure as described in example 67 with N-tert-butoxycarbonyl-L-norleucine in place of (S)-2-(tert-butoxycarbonylamino)butyric acid, the title compound was prepared.

$^1$H-NMR(CD$_3$OD) δ: 0.91–1.00(9H,m), 1.37–1.50(6H, m), 1.63–1.77(3H,m), 1.87–1.94(2H,m), 2.82–2.86(2H,m), 3.64–3.72(2H,m), 3.85–3.95(2H,m), 4.09–4.23(2H,m), 4.30–4.41(2H,m), 5.37(1H,t,J=6.6 Hz), 7.23–7.42(5H,m).

EXAMPLE 70

(S)-3-[(2S,3R,4R,5S)-5-(D-alanyl-L-leucyl)amino-2,3,4,6-tetrahydroxyhexanoyl]amino-3-phenylpropionic acid hydrochloride Following the same procedure as described in example 67 with N-tert-butoxycarbonyl-D-alanine in place of (S)-2-(tert-butoxycarbonylamino)butyric acid, the title compound was prepared.

$^1$H-NMR(CD$_3$OD) δ: 0.92–1.01(6H,m), 1.51(3H,d,J=7.0 Hz), 1.58–1.73(3H,m), 2.66–2.71(2H,m), 3.60–3.74(2H,m), 3.91–4.02(2H,m), 4.09–4.36(4H,m), 5.33(1H,t), 7.25–7.40 (5H,m).

EXAMPLE 71

(S)-3-[(2S,3R,4R,5S)-5-((β-cyano-L-alanyl)-L-leucyl)amino-2,3,4,6-tetrahydroxyhexanoyl]amino-3-phenylpropionic acid Following the same procedure as described in example 67 with N-tert-butoxycarbonyl-β-cyano-L-alanine in place of (S)-2-(tert-butoxycarbonylamino)butyric acid, the title compound was prepared.

$^1$H-NMR(CD$_3$OD) δ:0.93–0.99(6H,m), 1.61–1.82(3H, m), 2.74–2.95(4H,m), 3.62–3.92(5H,m), 4.17–4.46(3H,m), 5.37(1H,t,J=6.6Hz), 7.26–7.38(5H,m).

EXAMPLE 72

N-[(S)-3-[(2S,3R,4R,5S)-2,3,4,6-tetrahydroxy-5-(L-leucyl)aminohexanoyl]amino-3-phenylpropionyl]-L-alanine To absolution of (S)-3-[(2S,3R,4R,5S)-5-(N-benzyloxycarbonyl-L-leucyl)amino-2,3,4,6-tetrahydroxyhexanoyl]amino-3-phenylpropionic acid (200 mg), L alanine benzyl ester p-toluenesulfonate (238 mg) and N-hydroxy-5-norbornene-2,3-dicarboxyimide (183 mg) in acetonitrile (10 ml) were added N,N'-dicyclohexylcarbodimide (140 mg) and triethylamine (0.094 ml) and the mixture was stirred at room temperature for 15 hours. The formed insoluble solid was filtrated off and the filtrate was concentrated under reduced pressure. The residue was dissolved in ethyl acetate and washed with saturated brine, followed by drying over anhydrous sodium sulfate. Removal of the organic solvent gave a residue, which was dissolved in methanol (10 ml) and stirred at room temperature with 10% palladium on activated carbon (60 mg) under hydrogen atmosphere for 3 hours. After filtration, the filtrate was concentrated under reduced pressure to give a residue, which was passed through a column of DIAION HP-20SS (Mitsubishi kasei corporation), followed by elution with water-acetonitrile. The effective fractions were combined and concentrated under reduced pressure. The residue was recrystallized from methanol-ethyl acetate to afford the title compound (58 mg).

$^1$H-NMR(CD$_3$OD) δ:0.99–1.01(6H,m), 1.26(3H,d,J=7.4 Hz), 1.70–1.73(3H,m), 2.74–2.79(2H,m), 3.67–3.82(3H,m), 3.87–3.95(2H,m), 4.12–4.32(2H,m), 4.35(1H,d,J=1.2 Hz), 5.39.(1H,dd,J=7.0 Hz,5.4 Hz), 7.20–7.39(5H,m).

EXAMPLE 73

N-[(S)-3-[(2S,3R,4R,5S)-2,3,4,6-tetrahydroxy-5-(L-leucyl)aminohexanoyl]amino-3-phenylpropionyl]-L-leucine Following the same procedure as described in example 72 with L-leucine benzyl ester p-toluenesulfonate in place of L-alanine benzyl ester p-toluenesulfonate, the title compound was prepared.

$^1$H-NMR(CD$_3$OD) δ:0.79–1.00(12H,m), 1.30–1.96(6H, m), 2.78–2.81(2H,m), 3.66–3.81(3H,m), 3.85–3.92(2H,m), 4.20–4.39(3H,m), 5.38(1H,t,J=6.0 Hz), 7.20–7.34(5H,m).

EXAMPLE 74

(S)-3-[(2S,3R, 4R,5S)-2,3,4,6-tetrahydroxy-5-((O$^β$-methyl-α-L-aspartyl)-L-leucyl)aminohexanoyl] amino-3-phenylpropionic acid To a solution of N-tert-butoxycarbonyl-L-aspartic acid β-metyl ester (194 mg) in acetonitrile (5 ml) were added N-hydroxysuccinimide (56 mg) and N,N'-dicyclohexylcarbodiimide (95 mg) and the mixture was stirred at room temperature for 2 hours. The formed insoluble solid was filtrated off and the filtrate was added to a solution of (S)-3-[(2S,3R,4R,5S)-2,3,4,6-tetrahydroxy-5-(L-leucyl)aminohexanoyl]amino-3-phenylpropionic acid (compound 3) (200 mg) and triethylamine (0.10 ml) in dimethylformamide (30 ml). The mixtute was stirred at room temperature for 17 hours and concentrated under reduced pressure. To the residue was added 1N hydrochloric acid (50 ml) and the whole was extracted with ethyl acetate. The organic layer was washed with saturated brine and dried over anhydrous sodium sulfate. Removal of the organic solvent gave a residue, which was dissolved in trifluoroacetic acid (20 ml) and stirred at room temperature Concentration under reduced pressure gave a residue, which was passed through a column of DIAION HP-20SS (Mitsubishi kasei corporation), followed by elution with water-acetonitrile. The effective fractions were combined and concentrated under reduced pressure. The residue was recrystallized from methanol-ethyl acetate to afford the title compound (92 mg).

$^1$H-NMR(CD$_3$OD) δ:0.93–1.00(6H,m), 1.63–1.76(3H, m), 2.74(2H,d,J=6.3 Hz), 2.87(1H,dd,J=17.4 Hz,7.8 Hz), 3.04(1H,dd,J=17.4 Hz,5.4 Hz), 3.65–3.69(3H,m), 3.73(3H, s), 3.86(1H,dd,J=9.6 Hz,1.4 Hz), 4.07(1H,m), 4.21(1H,,m), 4.33–4.39(2H,m), 5.34(1H,t,J=6.3 Hz), 7.20–7.43(5H,m).

EXAMPLE 75 diphenylmethyl (S)-3-[(2S,3R,4R,5S)-5-((N-benzyloxycarbonylglycyl)-L-leucyl)amino-2,3,4,6-tetrahydroxyhexanoyl]amino-3-phenylpropionate To a solution of N-benzyloxycarbonylglycine (2.09 g) in dimethoxyethane (50 ml) were added N-hydroxysuccinimide (1.15 g) and N,N'-dicyclohexylcarbodimide (2.06 g) at 0° C. and the mixture was kept at 4° C. for 62 hours. The formed insoluble solid was filtrated off and the filtrate was concentrated under reduced pressure to give a residue, which was recrystallized from dichloromethane-hexane to provide N-benzyloxycarbonylglycine N-hydroxysuccinimide ester (3.00 g).

N-benzyloxycarbonylglycine N-hydroxysuccinimide ester (148 mg) was dissolved in dimethylformamide (6 ml) and to this solution was added diphenylmethyl (S)-3-[(2S,3R,4R,5S)-2,3,4,6-tetrahydroxy-5-(L-leucyl)aminohexanoyl]amino-3-phenylpropionate (300 mg) at room temperature. The mixtute was stirred at room temperature for 1.5 hours, followed by addition of 10% aqueous citric acid solution. The whole was extracted with ethyl acetate and the extract was washed with saturated aqueous sodium hydrogencarbonate solution and saturated brine respectively, followed by drying over anhydrous sodium sulfate. Removal of the organic solvent gave a residue, which was recrystallized from ethyl acetate-diethylether to afford the title compound (275 mg).

$^1$H-NMR(CD$_3$OD) δ:0.92(3H,d,J=5.8 Hz), 0.95(3H,d,J=5.8 Hz), 1.20–1.80(3H,m), 2.99(1H,dd,J=15.8 Hz,7.4 Hz), 3.10(1H,dd,J=15.8 Hz,6.2 Hz), 3.50–4.60(9H,m), 5.08(2H,s), 5.43(1H,dd,J=7.4 Hz,6.2 Hz), 6.95(1H,s), 7.10–7.40 (20H,m).

EXAMPLE 76

(S)-3-[(2S,3R,4R,5S)-5-(glycyl-L-leucyl)amino-2,3,4,6-tetrahydroxyhexanoyl]amino-3-phenylpropionic acid Diphenylmethyl (S)-3-[(2S,3R,4R,5S)-5-((N-benzyloxycarbonylglycyl)-L-leucyl)amino-2,3,4,6-tetrahydroxyhexanoyl]amino-3-phenylpropionate (273 ml) was dissolved in methanol (30 ml) and stirred at room temperature with 10% palladium on activated carbon (50 mg) under hydrogen atmosphere for 1.5 hours. After dilution with methanol, the mixture was filtrated and the filtrate was concentrated under reduced pressure to give a residue, which was recrystallized from methanol-diethylether to afford the title compound (154 mg).

$^1$H-NMR(CD$_3$OD) δ:0.94(3H,d,J=6.2 Hz), 0.99(3H,d,J=6.2 Hz), 1.10–1.85(3H,m), 2.66(1H,d,J=7.6 Hz), 3.50–4.40 (9H,m), 5.33(1H,t,J=7.6 Hz), 7.10–7.45(5H,m).

EXAMPLE 77 diphenylmethyl (S)-3-[(2S,3R,4R,5S)-5-((N-benzyloxycarbonyl-L-prolyl)-L-leucyl)amino-2,3,4,6-tetrahydroxyhexanoyl]amino-3-phenylpropionate Following the same procedure as described in example 75 with N-benzyloxycarbonyl-L-proline in place of N-benzyloxycarbonylglycine, the title compound was prepared.

$^1$H-NMR(DMSO-d$_6$) δ:0.60–2.30(13H,m), 3.00–5.40 (14H,m), 6.68(1H,s), 7.05–7.45(20H,m).

EXAMPLE 78

(S)-3-[(2S,3R,4R,5S)-2,3,4,6-tetrahydroxy-5-(L-prolyl-L-leucyl)aminohexanoyl]amino-3-phenylpropionic acid Following the same procedure as described in example 76 with diphenylmethyl (S)-3-[(2S,3R,4R,5S)-5-((N-benzyloxycarbonyl-L-prolyl)-L-leucyl)amino-2,3,4,6-tetrahydroxyhexanoyl]amino-3-phenylpropionate in place of diphenylmethyl (S)-3-[(2S,3R,4R,5S)-5-((N-benzyloxycarbonylglycyl)-L-leucyl)amino-2,3,4,6-tetrahydroxyhexanoyl]amino-3-phenylpropionate, the title compound was prepared.

$^1$H-NMR(DMSO-d$_6$) δ:0.80–1.00(6H,m), 1.40–2.20(7H,m), 2.60–5.30(13H,m), 7.15–7.45(5H,m), 7.59(1H,d,J=8.8 Hz), 8.15–8.30(2H,m).

EXAMPLE 79 diphenylmethyl (S)-3-[(2S,3R,4R,5S)-5-((O-benzyl-N-benzyloxycarbonyl-L-seryl)-L-leucyl)amino-2,3,4,6-tetrahydroxyhexanoyl]amino-3-phenylpropionate Following the same procedure as described in example 75 with O-benzyl-N-benzyloxycarbonyl-L-serine in place of N-benzyloxycarbonylglycine, the title compound was prepared.

$^1$H-NMR(DMSO-d$_6$) δ:0.85–0.95(6H,m), 1.50–1.70(3H,m), 2.97(1H,dd,J=14.6 Hz,7.0 Hz), 3.09(1H,dd,J=14.6 Hz,6.6 Hz), 3.60–4.50(10H,m), 4.47(1H,d,J=11.6 Hz), 4.56 (1H,d,J=11.6 Hz), 5.05(1H,d,J=12.0 Hz), 5.13(1H,d,J=12.0 Hz), 5.43(1H,dd,J=7.0 Hz,6.6 Hz), 6.72(1H,s), 7.10–7.40 (20H,m).

EXAMPLE 80

(S)-3-[(2S,3R,4R,5S)-5-((O-benzyl-L-seryl)-L-leucyl)amino-2,3,4,6-tetrahydroxyhexanoyl]amino-3-phenylpropionic acid Following the same procedure as described in example 76 with diphenylmethyl (S)-3-[(2S,3R,4R,5S)-5-((O-benzyl-N-benzyloxycarbonyl-L-seryl)-L-leucyl)amino-2,3,4,6-tetrahydroxyhexanoyl]amino-3-phenylpropionate in place of diphenylmethyl (S)-3-[(2S,3R,4R,5S)-5-((N-benzyloxycarbonylglycyl)-L-leucyl)amino-2,3,4,6-tetrahydroxyhexanoyl]amino-3-phenylpropionate, the title compound was prepared.

$^1$H-NMR(CD$_3$OD) δ:0.93(3H,d,J=6.6 Hz), 0.96(3H,d,J=6.6 Hz), 1.05–1.80(3H,m), 2.76(2H,d,J=6.6 Hz), 3.50–4.50 (10H,m), 4.62(2H,s), 5.30–5.50(1H,m), 7.15–7.50(10H,m).

EXAMPLE 81

(S)-3-[(2S,3R,4R,5S)-2,3,4,6-tetrahydroxy-5-(L-seryl-L-leucyl)aminohexanoyl]amino-3-phenylpropionic acid To a solution of O-benzyl-N-benzyloxycarbonyl-L-serine (228 mg) in acetonitrile (20 ml) were added N-hydroxysuccinimide (83 mg) and N,N'-dicyclohexylcarbodimide (143 mg) and the mixture was stirred at room temperature for 3 hours. The formed insoluble solid was filtrated off and the filtrate was added to a solution of (S)-3-[(2S,3R,4R,5S)-2,3,4,6-tetrahydroxy-5-(L-leucyl)aminohexanoyl]amino-3-phenylpropionic acid (compound 3) (300 mg) and triethylamine (0.092 ml) in dimethylformamide (60 ml). The mixtute was stirred at room temperature for 21 hours and concentrated under reduced pressure. To the residue was added 1N hydrochloric acid and the whole was extracted with ethyl acetate. The organic layer was washed with saturated brine and dried over anhydrous sodium sulfate. Removal of the organic solvent gave a residue, which was dissolved in methanol (20 ml) and stirred at room temperature with palladium hydroxide on carbon (200 mg) under hydrogen atmosphere (3 atm.) for 10 hours. After filtration, the filtrate was concentrated under reduced pressure to give a residue, which was passed through a column of DIAION HP-20SS (Mitsubishi kasei corporation), followed by elution with water-acetonitrile. The effective fractions were combined and concentrated under reduced pressure. The residue was recrystallized from methanoldiethylether to afford the title compound (60 mg).

$^1$H-NMR(CD$_3$OD) δ:0.94(3H,d,J=5.8 Hz), 0.98(3H,d,J= 5.8 Hz), 1.60–1.85(3H,m), 2.67(2H,d,J=6.6 Hz), 3.50–4.50 (10H,m), 5.33(1H,t,J=6.6 Hz), 7.15–7.50(5H,m).

EXAMPLE 82 diphenylmethyl (S)-3-[(2S,3R,4R,5S)-5-((N-benzyloxycarbonyl-L-valyl)-L-leucyl)amino-2,3,4,6-tetrahydroxyhexanoyl]amino-3-phenylpropionate Following the same procedure as described in example 75 with N-benzyloxycarbonyl-L-valine in place of N-benzyloxycarbonylglycine, the title compound was prepared.

$^1$H-NMR(DMSO-d$_6$) δ:0.75–0.95(12H,m), 1.40–2.10 (4H,m), 3.04(1H,d,J=6.8 Hz), 3.40–5.40(9H,m), 5.04(2H,s), 6.68(1H,s), 7.10–7.50(20H,m), 7.98(1H,d,J=7.6 Hz), 8.16 (1H,d,J=9.2 Hz).

EXAMPLE 83 diphenylmethyl (S)-3-[(2S, 3R,4R,5S)-6-acetoxy-5-((N-benzyloxycarbonyl-L-valyl)-L-leucyl)amino-2,3,4-trihydroxyhexanoyl]amino-3-phenylpropionate To a solution of diphenylmethyl (S)-3-[(2S,3R,4R,5S)-5-((N-benzyloxycarbonyl-L-valyl)-L-leucyl)amino-2,3,4,6-tetrahydroxyhexanoyl]amino-3-phenylpropionate (200 mg) in pyridine (1 ml) was added acetic anhydride (0.0243 ml) and the mixture was stirred at room temperature for 14 hours. After concentration under reduced pressure, the residue was passed through silica gel column chromatography, followed by elution with ethyl acetate-methanol (20:1). The effective fractions were combined and concentrated under reduced pressure to give a residue, which was recrystallized from mthanol-diethylether to provide the title compound (103 mg).

$^1$N-NMR(CD$_3$OD) δ:0.80–1.05(12H,m), 1.45–2.20(4H, m), 2.02(3H,s), 3.03(1H,dd,J=13.4 Hz,8.4 Hz), 3.21(1H,dd, J=13.4 Hz,9.6 Hz), 3.60–4.60(8H,m), 5.08(2H,s), 5.40–5.50 (1H,m), 6.73(1H,s), 7.10–7.40(20H,m).

EXAMPLE 84

(S)-3-[(2S,3R,4R,5S)-6-acetoxy-2,3,4-trihydroxy-5-(L-valyl-L-leucyl)aminohexanoyl]amino-3-phenylpropionic acid Following the same procedure as described in example 76 with diphenylmethyl (S)-3-[(2S,3R,4R,5S)-6-acetoxy-5-((N-benzyloxycarbonyl-L-valyl)-L-leucyl)amino-2,3,4-trihydroxyhexanoyl]amino-3-phenylpropionate in place of diphenylmethyl (S)-3-[(2S,3R,4R,5S)-5-((N-benzyloxycarbonylglycyl)-L-leucyl)amino-2,3,4,6-tetrahydroxyhexanoyl]amino-3-phenylpropionate, the title compound was prepared.

$^1$N-NMR(CD$_3$OD) δ:0.90–1.15(12H,m), 1.50–2.30(4H, m), 2.03(3H,s), 2.80(2H,d,J=6.6 Hz), 5.32(1H,t,J=6.6 Hz), 7.10–7.50(5H,m).

EXAMPLE 85 diphenylmethyl (S)-3-[(2S,3R,4R,5S)-5-((N-benzyloxycarbonyl-L-valyl)-L-leucyl)amino-2,3-dihydroxy-4,6-(O-isopropylidene)dioxyhexanoyl] amino-3-phenylpropionate To a solution of diphenylmethyl (S)-3-[(2S,3R,4R,5S)-5-((N-benzyloxycarbonyl-L-valyl)-L-leucyl)amino-2,3,4,6-tetrahydroxyhexanoyl]amino-3-phenylpropionate (200 mg) in tetrahydrofuran (5 ml) were added 2,2-dimethoxypropane (0.288 ml) and p-toluenesulfonic acid monohydrate (4 mg) and the mixture was stirred at room temperature for 1 hour. After addition of saturated aqueous sodium hydrogencarbonate solution, the whole was extracted with ethyl actate and the extract was washed with saturated brine, followed by drying over anhydrous sodium sulfate. Removal of the organic solvent gave a residue, which was recrystallized from ethyl acetate-hexane to provide the title compound (183 mg).

$^1$N-NMR(CD$_3$OD) δ:0.80–1.10(12H,m), 1.10–2.10(4H, m), 1.34(3H,s), 1.44(3H,s), 2.80–3.10(2H,m), 3.30–4.40 (8H,m), 5.05(1H,d,J=12.4 Hz), 5.13(1H,d,J=12.4 Hz), 6.81 (1H,s), 7.10–7.40(20H,m).

EXAMPLE 86

(S)-3-[(2S,3R,4R,5S)-2,3-dihydroxy-4,6-(O-isopropylidene)dioxy-5-(L-valyl-L-leucyl) aminohexanoyl]amino-3-phenylpropionic acid Following the same procedure as described in example 76 with diphenylmethyl (S)-3-[(2S,3R,4R,5S)-5-((N-benzyloxycarbonyl-L-valyl)-L-leucyl)amino-2,3-dihydroxy-4,6-(O-isopropylidene) dioxyhexanoyl]amino-3-phenylpropionate in place of diphenylmethyl (S)-3-[(2S,3R, 4R,5S)-5-((N-benzyloxycarbonylglycyl)-L-leucyl)amino-2, 3,4,6-tetrahydroxyhexanoyl]amino-3-phenylpropionate, the title compound was prepared.

$^1$N-NMR(CD$_3$OD) δ:0.79(3H,d,J=6.8 Hz), 0.80–0.95 (9H,m), 1.33(3H,s), 1.40(3H,s), 1.30–2.10(4H,m), 2.55–2.90(3H,m), 3.00–5–50(11H,m), 7.10–7.40(5H,m), 8.00–8.45(3H,m).

EXAMPLE 87

(S)-3-[(2S,3R,4R,5S)-2,3,4,6-tetrahydroxy-5-(L-tryptophanyl-L-leucyl)aminohexanoyl]amino-3-phenylpropionic acid To a solution of N-benzyloxycarbonyl-L-tryptophane (355 mg) in acetonitrile (30 ml) were added N-hydroxysuccinimide (127 mg) and N,N'-dicyclohexylcarbodimide (217 mg) and the mixture was stirred at room temperature for 3 hours. The formed insoluble solid was filtrated off and the filtrate was added to a solution of (S)-3-[(2S,3R,4R,5S)-2,3,4,6-tetrahydroxy-5-(L-leucyl)aminohexanoyl]amino-3-phenylpropionic acid (compound 3) (456 mg) and triethylamine (0.139 ml) in dimethylformamide (100 ml). The mixtute was stirred at room temperature for 19 hours and concentrated under reduced pressure. To the residue was added 1N hydrochloric acid and the whole was extracted with ethyl acetate-acetonitrile. The organic layer was washed with saturated brine and dried over anhydrous sodium sulfate. Removal of the organic solvent gave a residue, which was dissolved in methanol (30 ml) and stirred at room temperature with 10% palladium on activated carbon (200 mg) under hydrogen atmosphere for 24 hours. After filtration, the filtrate was concentrated under reduced pressure to give a residue, which was passed through flush silica gel column chromatography, followed by elution with acetonitrile-water (4:1). The effective fractions were combined and concentrated under reduced pressure to give a residue, which was passed through a column of DIAION HP-20SS (Mitsubishi kasei corporation), followed by elution with water-acetonitrile. The effective fractions were combined and concentrated under reduced pressure. The residue was recrystallized from methanol-diethylether to affordthe title compound (323 mg).

$^1$H-NMR(DMSO-d$_6$) δ:0.91(3H,d,J=6.2 Hz), 0.95(3H,d, J=6.2 Hz), 1.50–1.80(3H,m), 2.69(2H,d,J=6.2 Hz), 3.20–4.50(10H,m), 5.33(1H,t,J=6.2 Hz), 6.95–7.50(9H,m), 7.73(1H,d,J=7.4 Hz).

EXAMPLE 88

(S)-3-[(2S,3R,4R,5S)-2,3,4,6-tetrahydroxy-5-(N-(2-aminoisobutyryl)-L-leucyl)aminohexanoyl]amino-3-phenylpropionic acid To a solution of 2-(benzyloxycarbonylamino)isobutyric acid (81 mg) in acetonitrile (10 ml) were added N-hydroxysuccinimide (41 mg) and N,N'-dicyclohexylcarbodimide (71 mg) and the mixture was stirred at room temperature for 3 hours. The formed insoluble solid was filtrated off and the filtrate was added to a solution of (S)-3-[(2S,3R,4R,5S)-2,3,4,6-tetrahydroxy-5-(L-leucyl)aminohexanoyl]amino-3-phenylprbpionic acid (compound 3) (150 mg) and triethylamine (0.061 ml) in dimethylformamide (30 ml). The mixture was stirred at room temperature for 22 hours and concentrated under reduced pressure. The residue was dissolved in methanol (30 ml) and stirred at room temperature with 10% palladium on activated carbon (70 mg) under hydrogen atmosphere for 1 day. After filtration, the filtrate was concentrated under reduced pressure to give a residue, which was passed through a column of DIAION HP-20SS (Mitsubishi kasei corporation), followed by elution with water-acetonitrile. The effective fractions were combined and concentrated under reduced pressure. The residue was recrystallized from methanol-diisopropylether to afford the title compound (114 mg).

$^1$H-NMR(D$_2$O) δ:0.89(3H,d,J=5.4 Hz), 0.94(3H,d,J=5.8 Hz), 1.62(3H,s), 1.64(3H,s), 1.60–1.85(3H,m), 2.74(2H,d, J=7.0 Hz), 3.60–3.80(3H,m), 3.90(1H,d,J=9.9 Hz), 4.22–4.48(3H,m), 5.21(1H,t,J=7.0 Hz), 7.32–7.48(5H,m).

EXAMPLE 89

(S)-3-[(2S,3R,4R,5S)-5-(N-(1-aminocyclohexyl) carbonyl)-L-leucyl)amino-2,3,4,6-tetrahydroxyhexanoyl]amino-3-phenylpropionic acid Following the same procedure as described in example 88 with 1-(benzyloxycarbonylamino)cyclohexanecarboxylic acid in place of 2-(benzyloxycarbonylamino)isobutyric acid, the title compound was prepared.

$^1$H-NMR(DMSO-d$_6$) δ: 0.84–0.90(6H,m), 1.10–1.84 (13H,m), 2.69–2.75(2H,m), 3.15–4.09(10H,m), 4.13(1H,s), 4.38(1H,m), 5.20–5.28(2H,m), 5.76(1H,m), 7.21–7.40(5H, m), 7.49(1H,m), 8.10–8.28(2H,m).

EXAMPLE 90

(S)-3-[(2S,3R,4R,5S)-2,3,4,6-tetrahydroxy-5-(L-methionyl-L-leucyl)aminohexanoyl]amino-3-phenylpropionic acid To a solution of N-tert-butoxycarbonyl-L-methionine (86 mg) in acetonitrile (10 ml) were added N-hydroxysuccinimide (41 mg) and N,N'-dicyclohexylcarbodimide (71 mg) and the mixture was stirred at room temperature for 2.5 hours. The formed insoluble solid was filtrated off and the filtrate was added to a solution of (S)-3-[(2S,3R,4R,5S)-2,3,4, 6-tetrahydroxy-5-(L-leucyl)aminohexanoyl]amino-3-phenylpropionic acid (compound 3) (150 mg) and triethylamine (0.061 ml) in dimethylformamide (30 ml). The mixtute was stirred at room temperature for 18.5 hours and concentrated under reduced pressure. To the residue was added 4N hydrogen chloride solution in ethyl acetate (5 ml) and the whole was stirred at room temperature for 2 hours. Removal of the organic solvent gave a residue, which was passed through a column of DIAION HP-20SS (Mitsubishi kasei corporation), followed by elution with water-acetonitrile. The effective fractions were combined and concentrated under reduced pressure. The residue was recrystallized from methanol-ethyl acetate to afford the title compound (60 mg).

$^1$H-NMR(DMSO-d$_6$) δ:0.84–0.91(6H,m), 1.45–1.99(5H, m), 2.03(3H,s), 2.47–2.56(2H,m), 2.69–2.75(2H,m), 3.40–4.00(6H,m), 4.13(1H,s), 4.37(1H,m), 5.21(1H,m), 7.21–7.38(5H,m), 7.49(1H,br d,J=8.8 Hz), 8.18(1H,m), 8.29 (1H,br d,J=7.0 Hz).

EXAMPLE 91

(S)-3-[(2S,3R,4R,5S)-2,3,4,6-tetrahydroxy-5-((S-methyl-L-cysteinyl)-L-leucyl)aminohexanoyl] amino-3-phenylpropionic acid Following the same procedure as described in example 90 with N-tert-butoxycarbonyl-S-methyl-L-cysteine in place of N-tert-butoxycarbonyl-L-methionine, the title compound was prepared.

$^1$H-NMR(DMSO-d$_6$) δ:0.84–0.91(6H,m), 1.46–1.73(3H, m), 1.91(2H,m), 2.05(3H,s), 2.55–2.88(4H,m), 3.40– 4.09 (6H,m), 4.13(1H,s), 4.38(1H,m), 5.22(1H,m), 7.21–7.38 (5H,m), 7.50(1H,br d,J=8.4 Hz), 8.14–8.25(2H,m).

EXAMPLE 92

(S)-3-[(2S,3R,4R,5S)-5-(N-((S)-2-amino-4-pentenoyl)-L-leucyl)amino-2,3,4,6-tetrahydroxyhexanoyl]amino-3-phenylpropionic acid Following the same procedure as described in example 90 with (S)-2-tert-butoxycarbonylamino-4-pentenoic acid in place of N-tert-butoxycarbonyl-L-methionine, the title compound was prepared.

$^1$H-NMR(DMSO-d$_6$) δ:0.84–0.90(6H,m), 1.43–1.64(3H, m), 2.12–2.48(2H,m), 2.69–2.75(2H,m), 3.40–4.09(6H,m), 4.13(1H,s), 4.38(1H,m), 5.00–5.28(3H,m), 5.76(1H,m), 7.21–7.40(5H,m), 7.49(1H,br d,J=8.6 Hz), 8.13(1H,br d,J= 7.6 Hz), 8.28(1H,br d,J=10.8 Hz).

EXAMPLE 93

(S)-3-[(2S,3R,4R,5S)-2,3,4,6-tetrahydroxy-5-(N-((S)-2-pyrrolidone-5-carbonyl)-L-leucyl) aminohexanoyl]amino-3-phenylpropionic acid To a solution of L-pyroglutamic acid (44 mg) in acetonitrile (10 ml) were added N-hydroxysuccinimide (41 mg) and N,N'-dicyclohexylcarbodimide (71 mg) and the mixture was stirred at room temperature for 2 hours. The formed insoluble solid was filtrated off and the filtrate was added to a solution of (S)-3-[(2S,3R,4R,5S)-2,3,4,6-tetrahydroxy-5-(L-leucyl)aminohexanoyl]amino-3-phenylpropionic acid (compound 3) (150 mg) and triethylamine (0.061 ml) in dimethylformamide (30 ml). The mixtute was stirred at room temperature for 22 hours and concentrated under reduced pressure. The residue was passed through a column of DIAION HP-20SS (Mitsubishi kasei corporation), followed by elution with water-acetonitrile. The effective fractions were combined and concentrated under reduced pressure. The residue was passed a column-of Sephadex LH-20 (Pharmacia, Sweden), followed by elution with water. The effective fractions were combined and concentrated under reduced pressure. The residue was recrystallized from methanol-ethyl acetate to afford the title compound (24 mg).

$^1$N-NMR(CD$_3$OD) δ:0.94(3H,d,J=6.2 Hz), 0.97(3H,d,J=6.6 Hz), 1.62–1.78(3H,m), 2.11–2.48(4H,m), 2.89(2H,t,J=6.4 Hz), 3.65–3.72(3H,m), 3.91(1H,d,J=9.8 Hz), 4.19–4.26 (2H1m), 4.32(1H,d,J=1.4 Hz), 4.50(1H,m), 5.38(1H,t,J=6.4 Hz), 7.23–7.42(5H,m).

EXAMPLE 94 diphenylmethyl (S)-3-[(2S,3R,4R,55)-2,3,4,6-tetrahydroxy-5-((N,N-dimethyl-L-valyl)-L-leucyl) aminohexanoyl]amino-3-phenylpropionate To a solution of N,N-dimethyl-L-valine (58 mg) and diphenylmethyl (S)-3-[(2S,3R,4R,5S)-2,3,4,6-tetrahydroxy-5-(L-leucyl)aminohexanoyl]amino-3-phenylpropionate (250 mg) in dimethylformamide (4 ml) were added diethyl cyanophosophonate (82 mg) and triethylamine (0.14 ml) and the mixture was stirred at room temperature for 18 hours. After addition of water, the whole was extracted with ethyl acetate and the extract was washed with saturated brine, followed by drying over anhydrous sodium sulfate. Removal of the organic solvent gave a residue, which was recrystallized from ehtyl acetate-hexane to afford the title compound (282 mg).

$^1$H-NMR(DMSO-d$_6$) δ:0.70–0.95(12H,m), 1.00–2.00 (4H,m), 2.17(6H,s), 3.04(2H,d,J=7.0 Hz), 3.30–5.40(12H, m), 6.67(1H,s), 7.10–7.40(16H,m), 8.01(1H,d,J=8.8 Hz), 8.15(1H,d,J=8.8 Hz).

EXAMPLE 95

(S)-3-[(2S,3R,4R,5S)-2,3,4,6-tetrahydroxy-5-(L-valyl-(N-methyl-L-leucyl)aminohexanoyl]amino-3-phenylpropionic acid To a solution of (N-tert-butoxycarbonyl-L-valyl)-N-methyl-L-leucine (240 mg) in acetonitrile (20 ml) were added N-hydroxysuccinimide (88 mg) and N,N'-dicyclohexylcarbodiimide (151 mg) and the mixture was stirred at room temperature for 3 hours. The formed insoluble solid was filtrated off and the filtrate was added to a solution of (S)-3-[(2S,3R,4R,5S)-5-amino-2,3,4,6-tetrahydroxyhexanoyl]amino-3-phenylpropionic acid (compound 5) (239 mg) and triethylamine (0.097 ml) in dimethylformamide (70 ml). The mixtute was stirred at room temperature for 16 hours and concentrated under reduced pressure. To the residue was added 4N hydrogen chloride solution in ethyl acetate (20 ml) and the whole was stirred at room temperature for 1 hour. Removal of the organic solvent gave a residue, which was passed through a column of DIAION HP-20SS (Mitsubishi kasei corporation), followed by elution with water-acetonitrile. The effective fractions were combined and concentrated under reduced pressure. The residue was recrystallized from methanol-diethylether to afford the title compound (123 mg).

$^1$H-NMR(DMSO-d$_6$) δ:0.70–1.00(12H,m), 1.00–2.20 (4H,m), 2.50–2.80(2H,m), 2.86(3/2H,s), 2.89(3/2H,s), 3.00–5.30(9H,m), 7.10–7.40(5H,m).

EXAMPLE 96

(S)-3-[(2S,3R,4R,5S)-5-(N-((S)-2-amino-3-methylbutyl)-L-leucyl)amino-2,3,4,6-tetrahydroxyhexanoyl]amino-3-phenylpropionic acid To a solution of N-tert-butoxycarbonyl-L-valinal (240 mg) and diphenylmethyl (S)-3-[(2S,3R,4R,5S)-2,3,4,6-tetrahydroxy-5-(L-leucyl)aminohexanoyl]amino-3-phenylpropionate (278 mg) in methanol (10 ml) was added sodium cyanoborohydride (63 mg) at 0° C. and the mixture was stirred at 0° C. for 2 hours and at room temperature for 18 hours. After concentration under reduced pressure, the residue was subjected to flush silica gel column chromatography, followed by elution with ethyl acetate-methanol(20:1). The effective fractions were combined and concentrated under reduced pressure. To the residue was added 4N hydrogen chloride solution in ethyl acetate (10 ml) and the whole was stirred at room temperature for 1 hour. Removal of the organic solvent gave a residue, which was passed through a column of DIAION HP-20SS (Mitsubishi kasei corporation), followed by elution with water-acetonitrile. The effective fractions were combined and concentrated under reduced pressure. The residue was recrystallized from methanol-diethylether to afford the title compound (25 mg).

$^1$H-NMR(DMSO-d$_6$+3% TFA) δ:0.85–1.10(6H,m), 1.40–2.60(4H,m), 2.70–2.90(2H,m), 2.90–5.40(9H,m), 7.20–7.45(5H,m), 8.00–8.40(2H,m).

EXAMPLE 97

(S)-3-[(2S,3R,4R,5S)-2,3,4,6-tetrahydroxy-5-((S)-2-(L-norvarlyl)amino-4-pentenoyl)aminohexanoyl] amino-3-phenylpropionic acid To a solution of N-tert-butoxycarbonyl-L-norvalin (54 mg) in acetonitrile (1 ml) were added N-hydroxysuccinimide (29 mg) and N,N'-dicyclohexylcarbodiimide (52 mg) and the mixture was stirred at room temperature for 3 hours. The formed insoluble solid was filtrated off and the filtrate was concentrated under reduced pressure. The residue was dissolved in dimethylformamide (8 ml) and to the solution were added (S)-3-[(2S,3R,4R,5S)-5-((S)-2-amino-4-pentenoyl)amino-2, 3,4,6-tetrahydroxyhexanoyl]amino-3-phenylpropionic acid (110 mg) and triethylamine (0.035 ml). The mixtute was stirred at room temperature for 20 hours and concentrated under reduced pressure. To the residue was added 4N hydrogen chloride solution in ethyl acetate (10 ml) and the whole was stirred at room temperature for 1 hour. Removal of the organic solvent gave a residue, which was passed through a column of DIAION HP-20SS (Mitsubishi kasei corporation), followed by elution with water-acetonitrile. The effective fractions were combined and concentrated under reduced pressure. The residue was recrystallized from methanol-diethylether to afford the title compound (56 mg).

$^1$H-NMR(DMSO-d$_6$) δ:0.86(3H,t,J=7.0 Hz), 1.20–1.80 (4H,m), 2.20–2.90(4H,m), 3.30–5.90(12H,m), 7.10–7.45 (5H,m), 7.54(1H,d,J=7.8 Hz), 8.28(1H,d,J=12.8 Hz).

EXAMPLE 98

(S)-3-[(2S,3R,4R,5S)-2,3,4,6-tetrahydroxy-5-((S)-2-(L-isoleucyl )amino-4-pentenoyl)aminohexanoyl] amino-3-phenylpropionic acid Following the same procedure as described in example 97 with N-tert-butoxycarbonyl-L-isoleucine in place of N-tert-butoxycarbonyl-L-norvaline, the title compound was prepared.

$^1$H-NMR(DMSO-d$_6$) δ:0.75–0.95(6H,m), 0.95–1.80(3H, m), 2.10–2.90(4H,m), 3.10–4.50(8H,m), 4.95–5.90(4H,m), 7.15–7.20(5H,m).

EXAMPLE 99

(S)-3-[(2S,3R,4R,5S)-2,3,4,6-tetrahydroxy-5-((S)-2-(L-methionyl)amino-4-pentenoyl)aminohexanoyl] amino-$^3$-phenylpropionic acid Following the same procedure as described in example 97 with N-tert-butoxycarbonyl-L-methionine in place of N-tert-butoxycarbonyl-L-norvaline, the title compound was prepared.

$^1$H-NMR(DMSO-d$_6$) δ:1.50–2.10(2H,m), 2.10–3.00(6H, m), 2.03(3H,s), 3.20–5.90(9H,m), 7.15–7.40(5H,m).

EXAMPLE 100 ethyl (S)-3-[(2S,3R,4R,5S)-2,3,4,6-tetraacetoxy-5-(N-benzyloxycarbonyl-L-leucyl)aminohexanoyl]amino-3-(4-methylphenyl)propionate To a solution of [(2S,3R,4R,5S)-2,3,4,6-tetraacetoxy-5-(N-benzyloxycarbonyl-L-leucyl)aminohexanoic acid (250 mg) in acetonitrile (10 ml) were added N-hydroxy-5-norbornene-2,3-dicarboxyimide (110 mg) and N,N'-dicyclohexylcarbodimide (110 mg) and the mixture was stirred at room temperature for 1 hour. After addition of a solution of ethyl (S)-3-amino-3-(4-methylphenyl)propionate (150 mg) and triethylamine (0.13 ml) in acetonitrile (10 ml), the whole was stirred at room temperature for 18 hours. The formed insoluble solid was filtrated off and the filtrate was concentrated under reduced pressure. The residue was dissolved in ethyl acetate (100 ml) and washed with saturated brine (50 ml×2), followed by drying over anhydrous sodium sulfate. After concentration under reduced pressure, the residue was passed through silica gel column chromatography, followed by elution with ethyl acetate-hexane (2:1). The effective fractions were combined and concentrated under reduced pressure to afford the title compound (184 mg).

$^1$N-NMR(CD$_3$OD) δ:0.89–0.96(6H,m), 1.15(3H,q,J=7.2 Hz), 1.45–1.73(3H,m), 1.96(3H,s), 2.01(3H,s), 2.04(3H,s), 2.08(3H,s), 2.28(3H,s), 2.76(1H,dd,J=15.8 Hz,7.4 Hz), 2.88 (1H,dd,J=15.8 Hz,7.4 Hz), 3.80(1H,dd,J=11.0 Hz,7.2 Hz), 3.99–4.21(7H,m), 4.51(1H,t,J=7.4 Hz), 5.07(2H,s), 5.22 (1H,t,J=7.4 Hz), 5.37(2H,s), 7.10(2H,d,J=8.0 Hz), 7.18(2H, d,J=8.0 Hz), 7.30–7.36(5H,m).

EXAMPLE 101

(S)-3-[(2S,3R,4R,5S)-2,3,4,6-tetrahydroxy-5-(L-leucyl)aminohexanoyl]amino-3-(4-methylphenyl) propionic acid A solution of ethyl (S)-3-[(2S,3R,4 R,5S)-2,3,4,6-tetraacetoxy-5-(N-benzyloxycarbonyl-L-leucyl)aminohexanoyl]amino-3-(4-methylphenyl)propionate (184 mg) in methanol (10 ml) was stirred at room temperature with 10% palladium on activated carbon (100 mg) under hydrogen atmosphere for 2 hours. After filtration, the filtrate was concentrated under reduced pressure. The residue was dissolved in methanol (10 ml) and to the solution was added 1N aqueous sodium hydroxide solution (2.2 ml) under ice-cooling. The mixture was stirred under ice-cooling for 1hour, followed by addition of 1N hydrochloric acid (2.2 ml). After concentration under reduced pressure, the residue was passed through a column of DIAION HP-20SS (Mitsubishi kasei corporation), followed by elution with water-acetonitrile. The effective fractions were combined and concentrated under reduced pressure. The residue was recrystallized from methanol-ethyl acetate to afford the title compound (50 mg).

$^1$N-NMR(CD$_3$OD) δ:0.98–1.02(6H,m), 1.60–1.85(3H, m), 2.27(3H,s), 2.67(2H,d,J=6.4 Hz), 3.65–3.74(3H,m), 3.85–3.90(2H,m), 4.24–4.31(2H,m), 5.27(1H,t,J=6.4 Hz), 7.09(2H,d,J=8.0 Hz), 7.26(2H,d,J=8.0 Hz).

The structural formulas of compounds obtained in Reference Examples and Examples are shown below. Abbreviation "Ac" means acetyl.

Compound of Reference Example 2

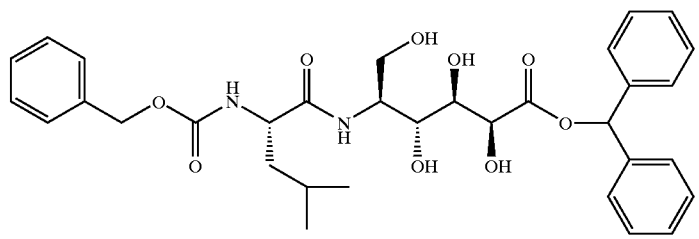

Compound of Reference Example 3

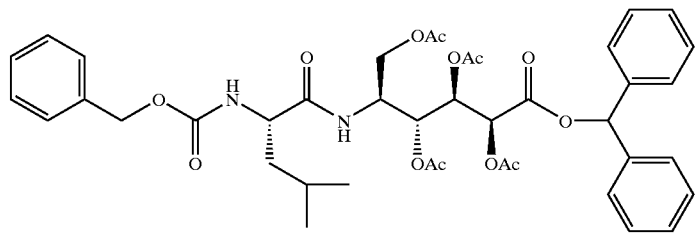

Compound of Reference Example 4

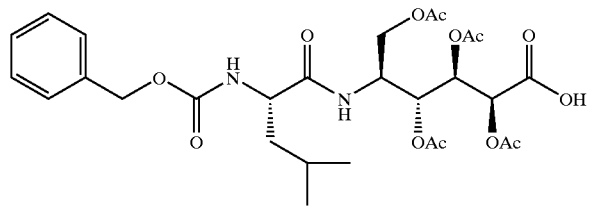

| | |
|---|---|
| Compound of Example 9 | 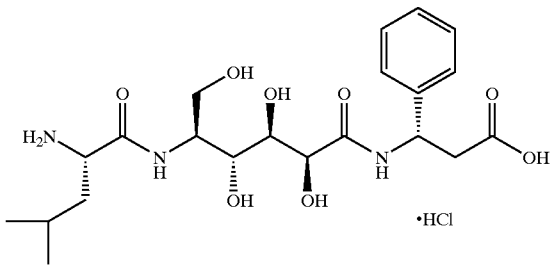 |
| Compound of Example 10 | 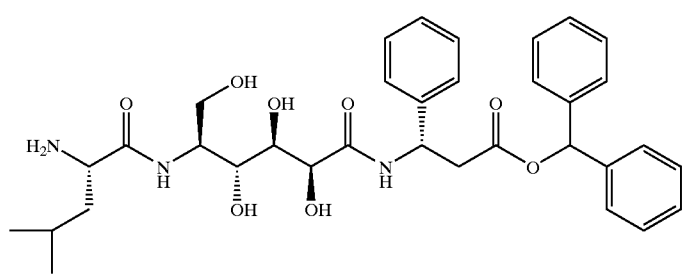 |
| Compound of Example 11 | 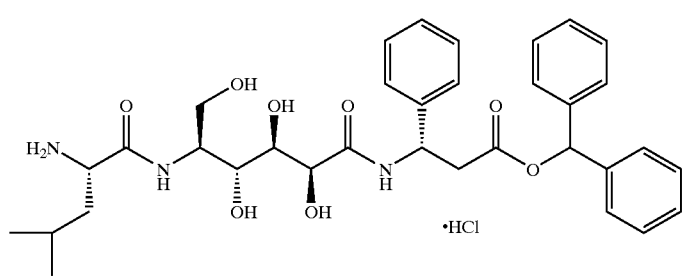 |
| Compound of Example 12 | 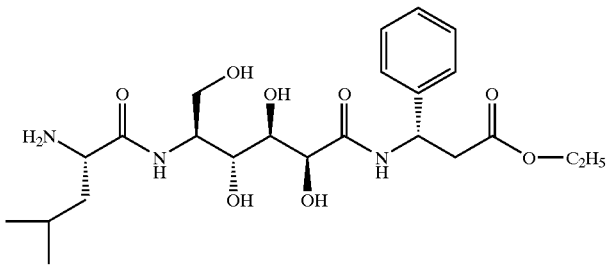 |
| Compound of Example 13 | 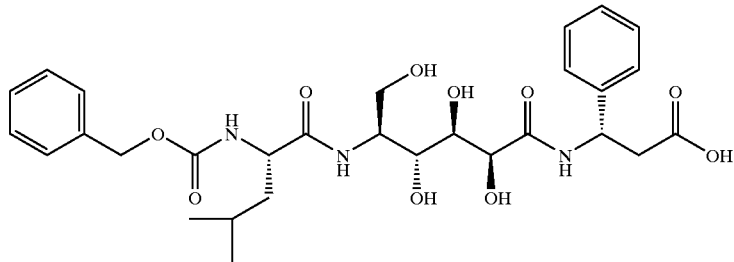 |

Compound of Example 14
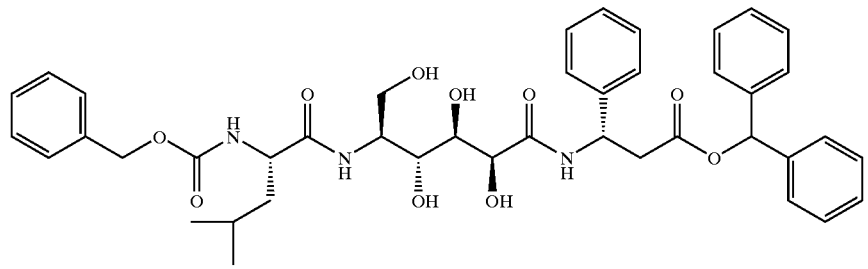
Compound of Example 15
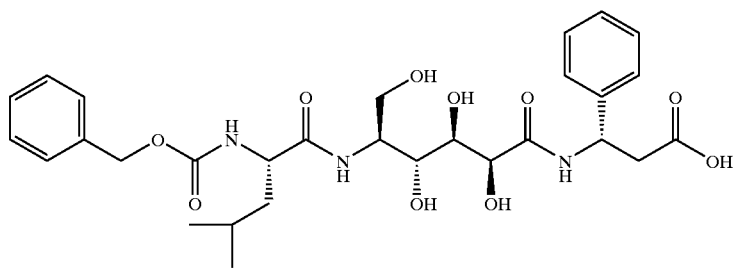
Compound of Example 16
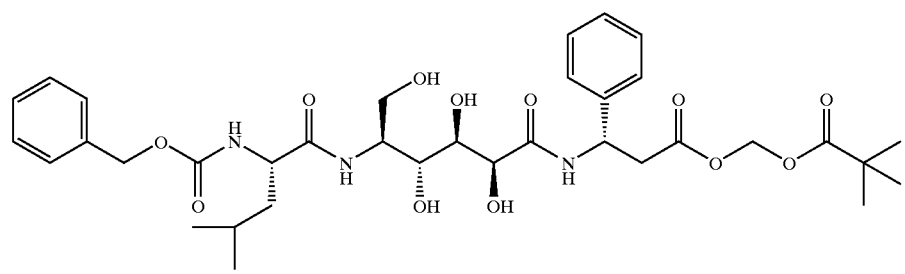
Compound of Example 17
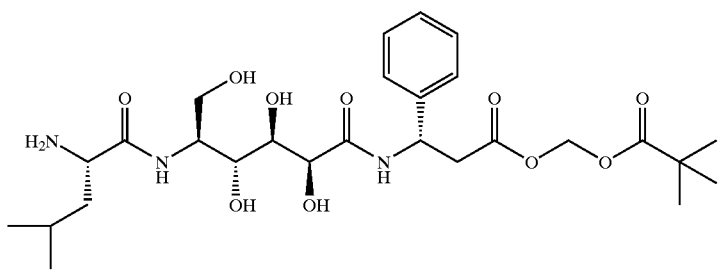
Compound of Example 18
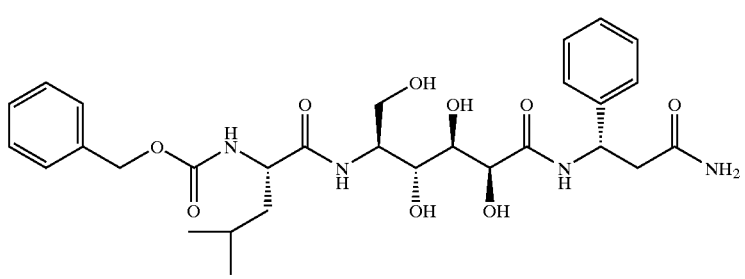

-continued
Compound of Example 19
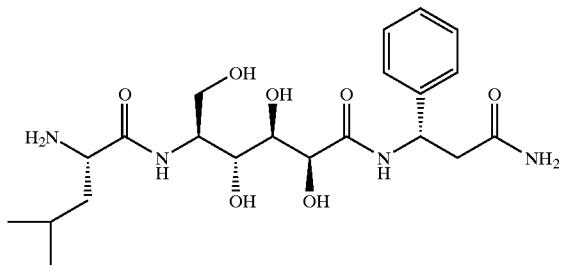
Compound of Example 20
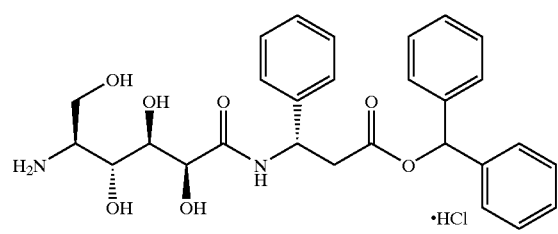
Compound of Example 21
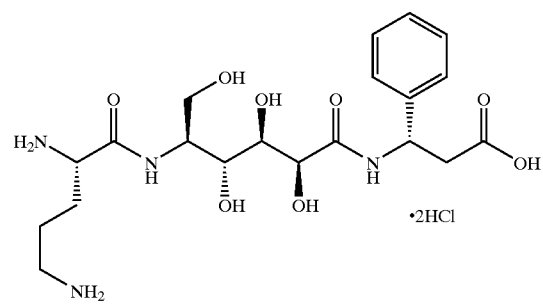
Compound of Example 22
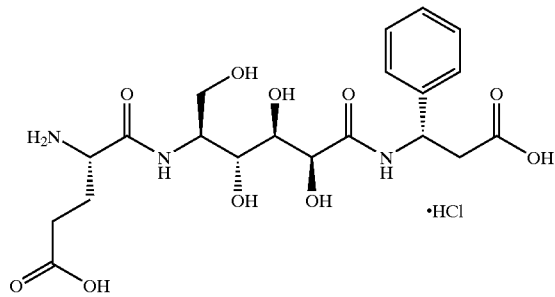
Compound of Example 23
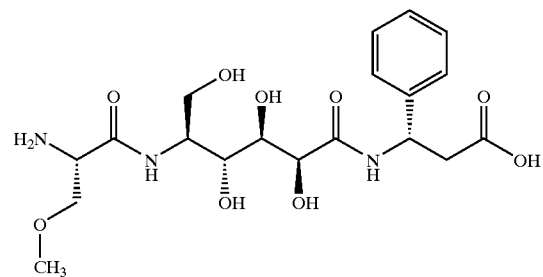

Compound of Example 24
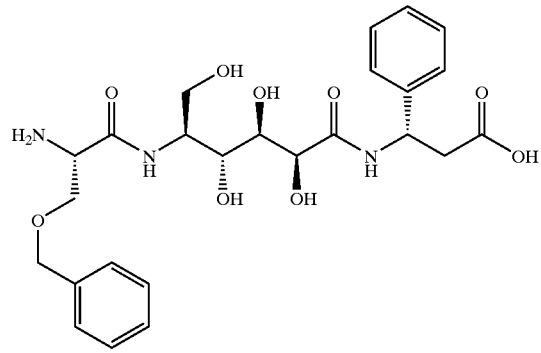
Compound of Example 25
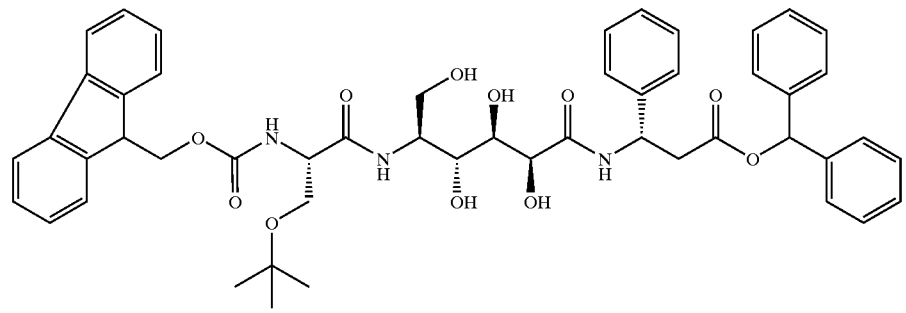
Compound of Example 26
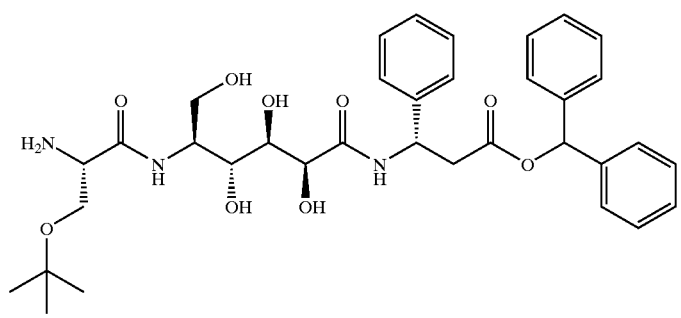
Compound of Example 27
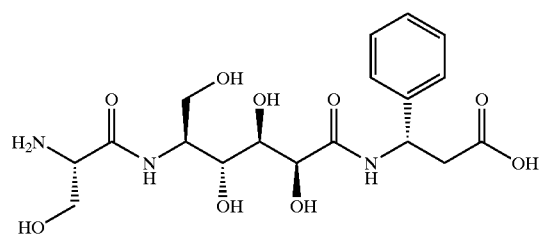
Compound of Example 28
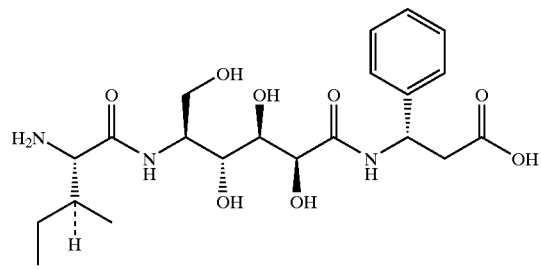

-continued
Compound of Example 29
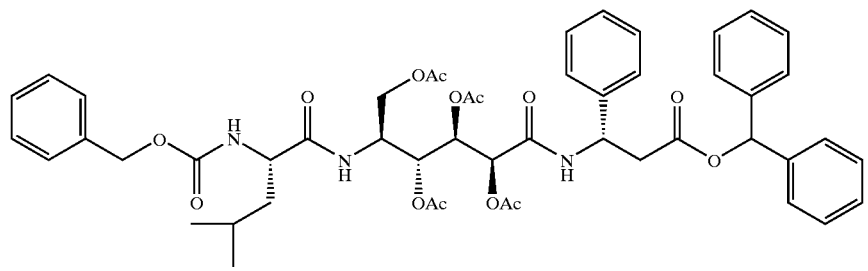
Compound of Example 30
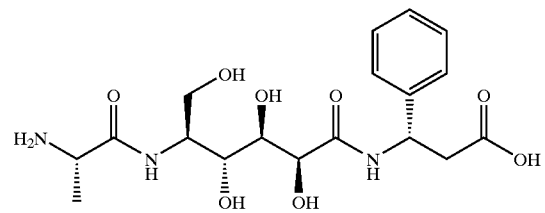
Compound of Example 31
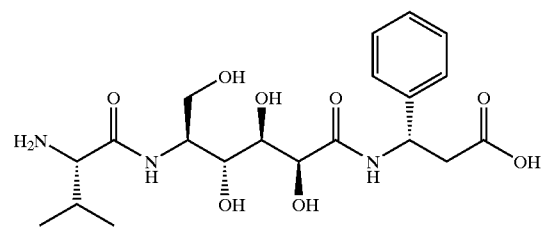
Compound of Example 32
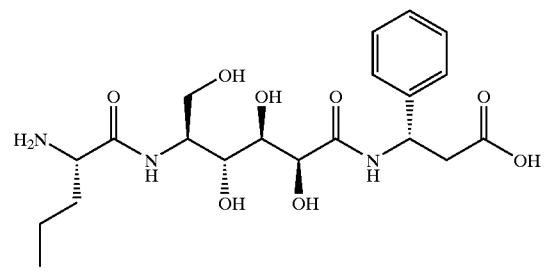
Compound of Example 33
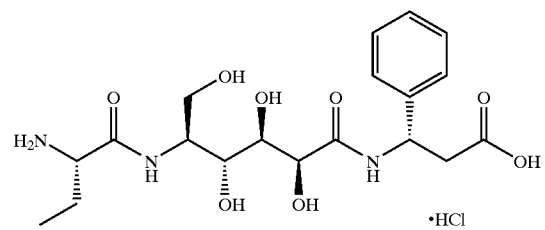
Compound of Example 34
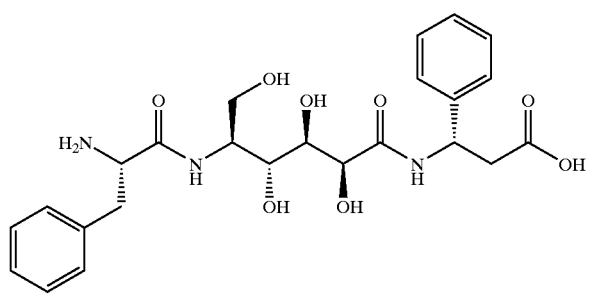

-continued
Compound of Example 35
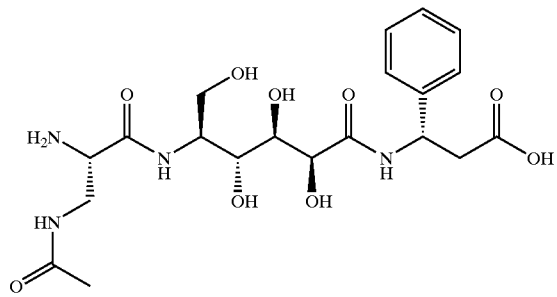
Compound of Example 36
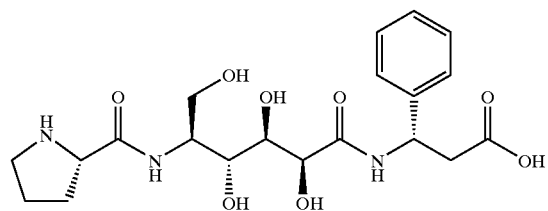
Compound of Example 37
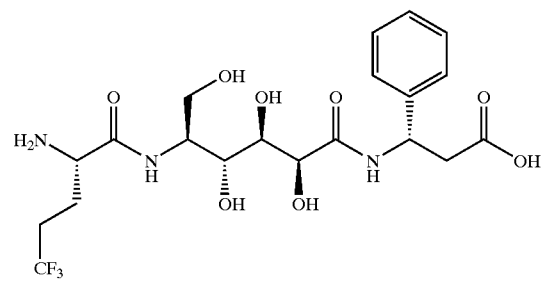
Compound of Example 38
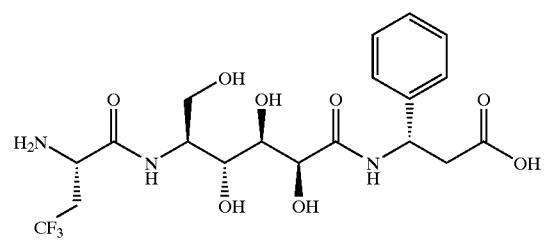
Compound of Example 39
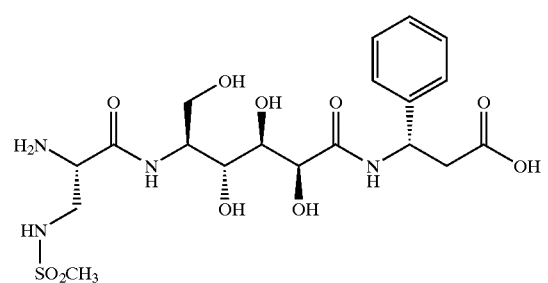

Compound of Example 40
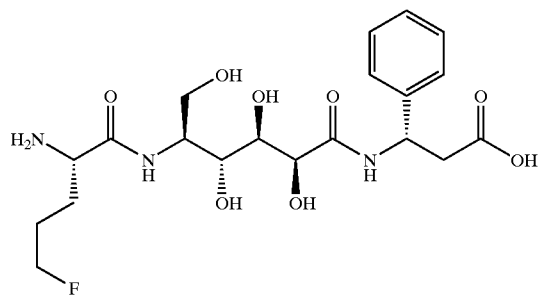
Compound of Example 41
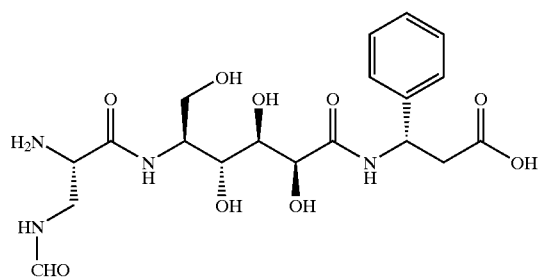
Compound of Example 42
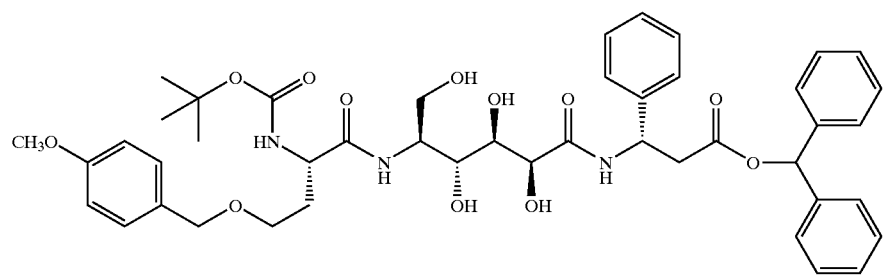
Compound of Example 43
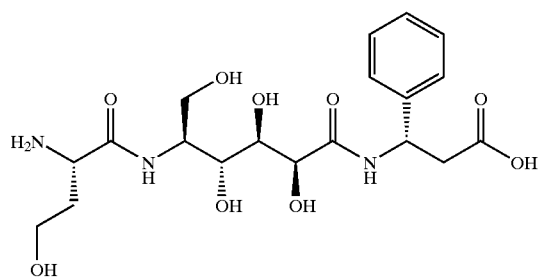
Compound of Example 44
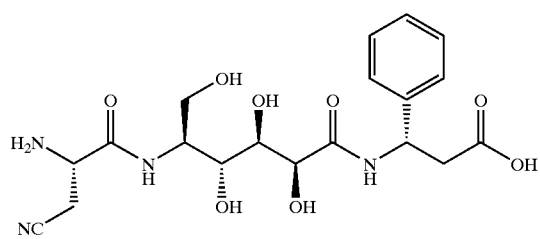

-continued
Compound of Example 45
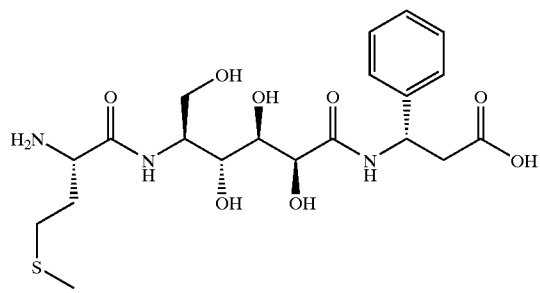
Compound of Example 46
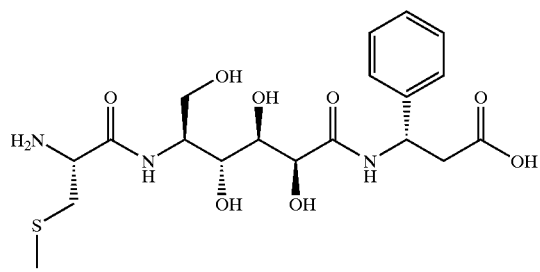
Compound of Example 47
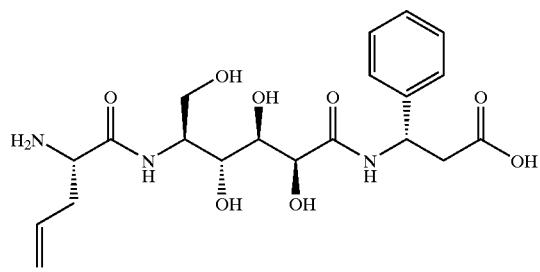
Compound of Example 48
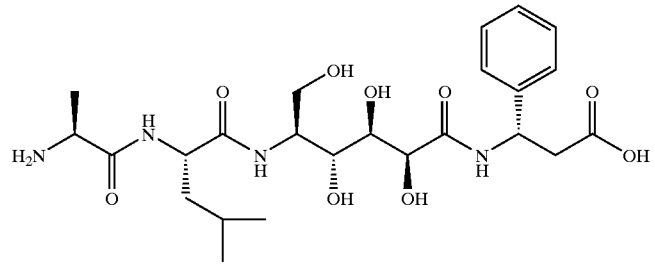
Compound of Example 49
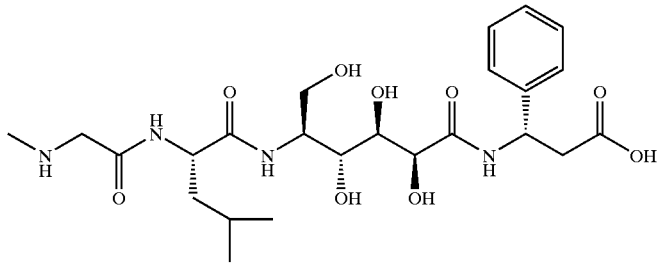

-continued
Compound of Example 50
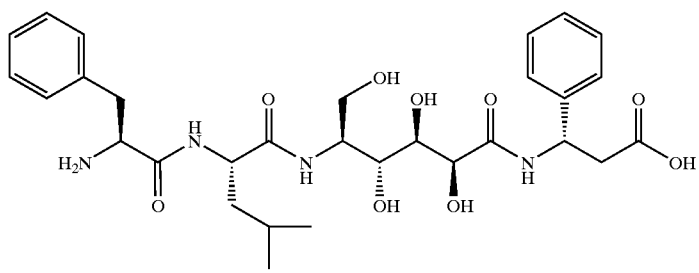
Compound of Example 51
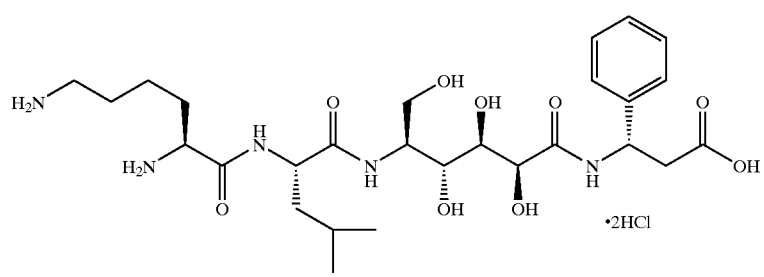
Compound of Example 52
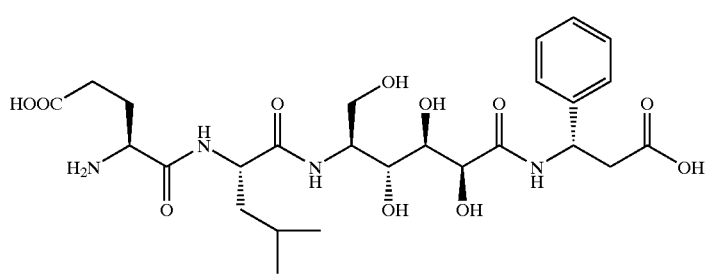
Compound of Example 53
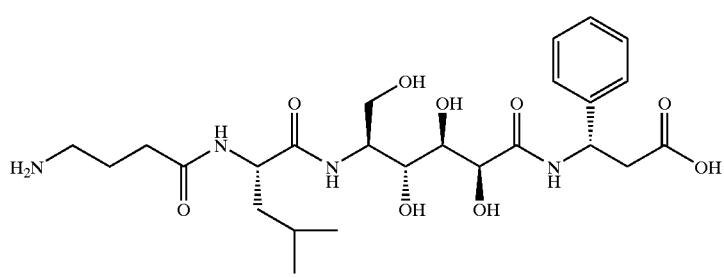
Compound of Example 54
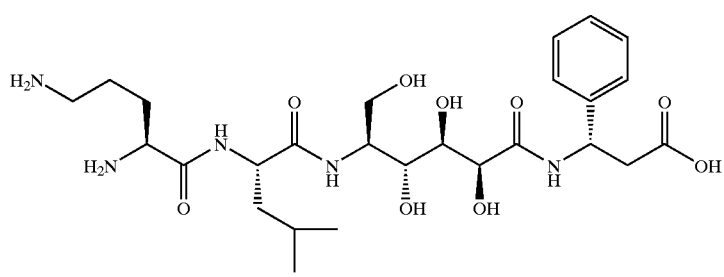

-continued
Compound of Example 55
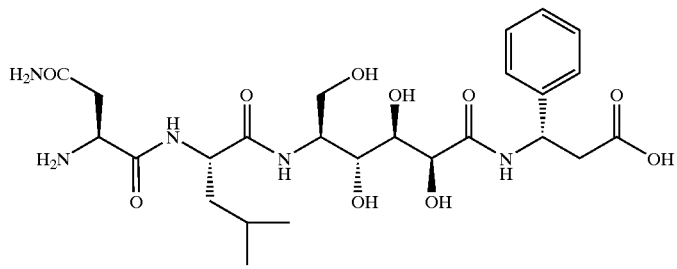
Compound of Example 56
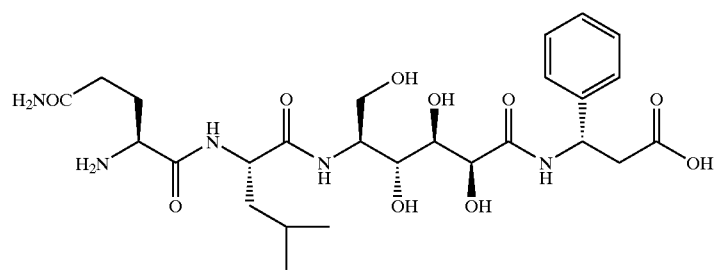
Compound of Example 57
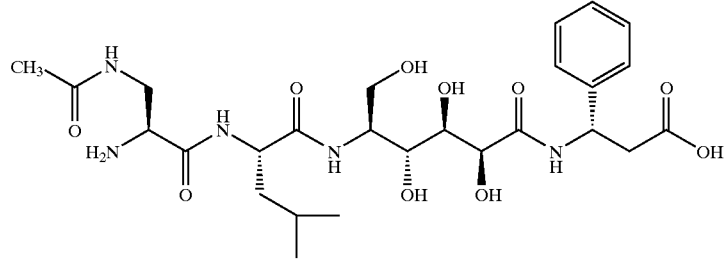
Compound of Example 58
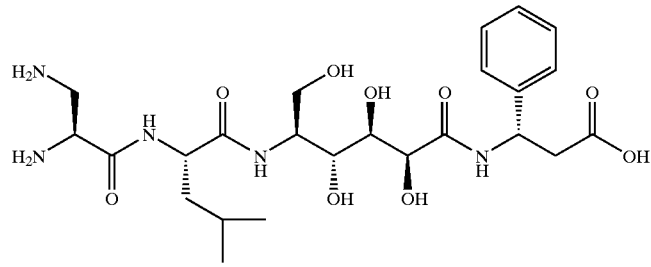
Compound of Example 59
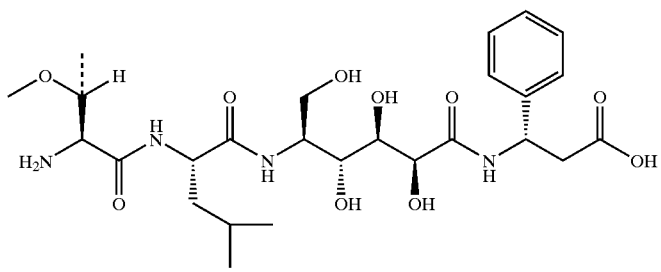

-continued
Compound of Example 60
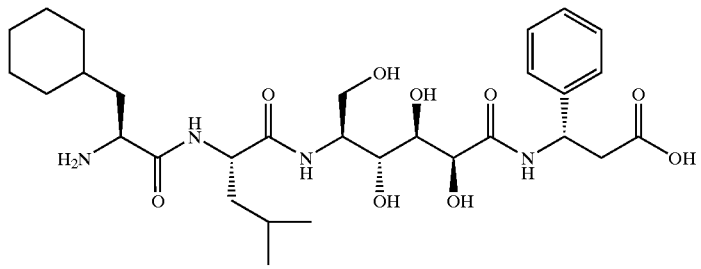
Compound of Example 61
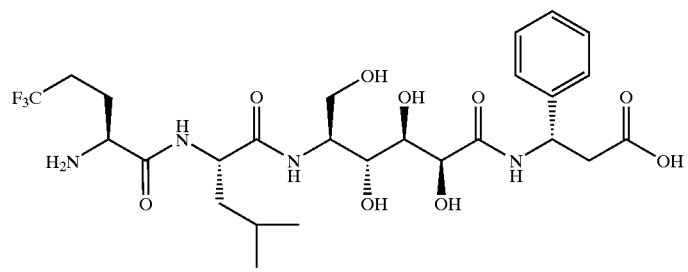
Compound of Example 62
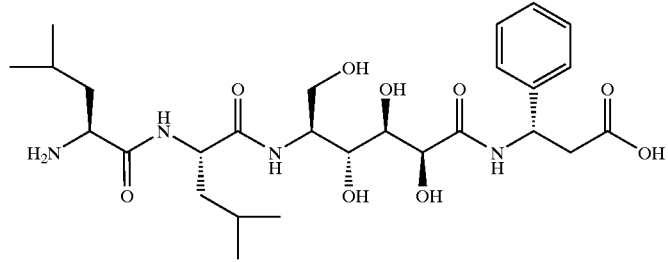
Compound of Example 63
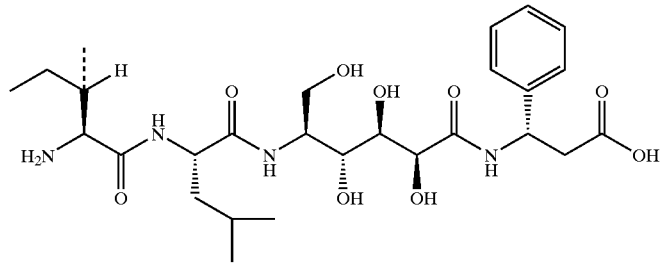
Compound of Example 64
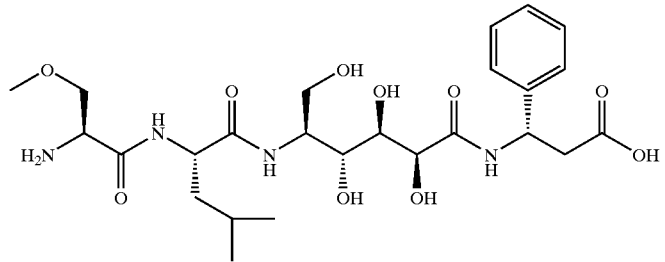

| | |
|---|---|
| Compound of Example 65 | 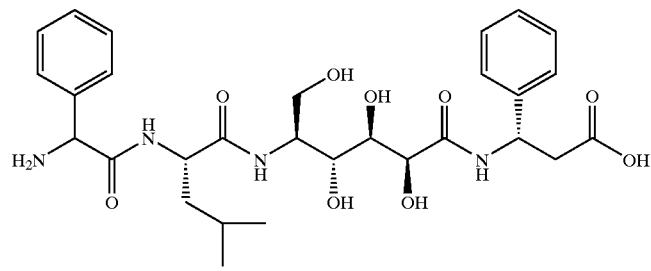 |
| Compound of Example 66 | 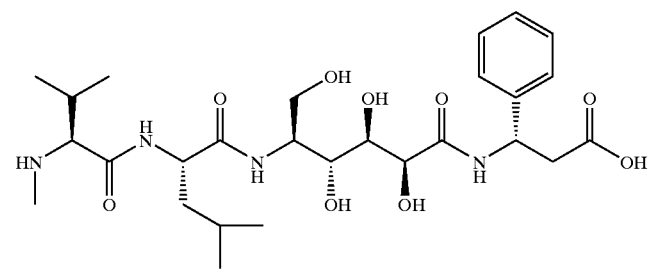 |
| Compound of Example 67 | 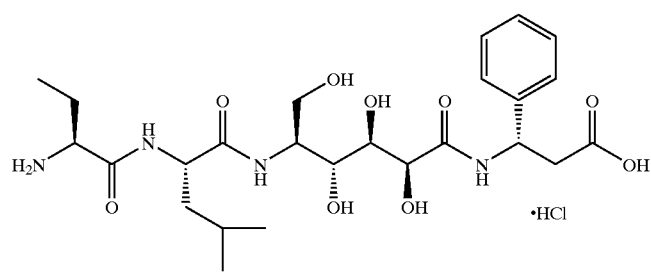 |
| Compound of Example 68 | 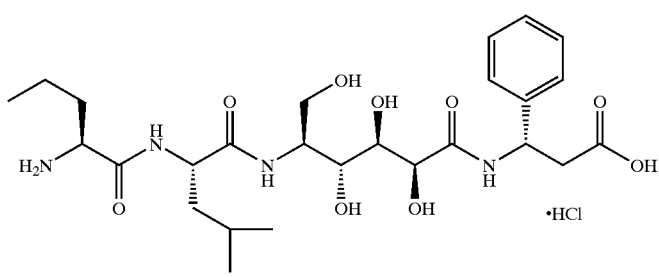 |
| Compound of Example 69 | 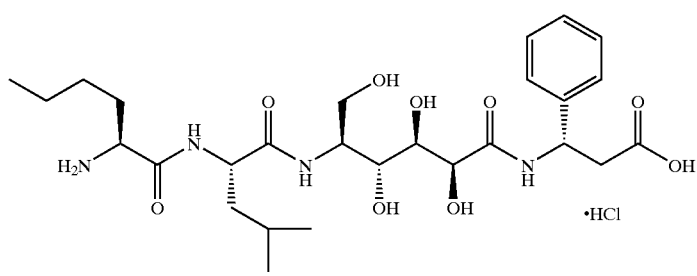 |

-continued
Compound of Example 70
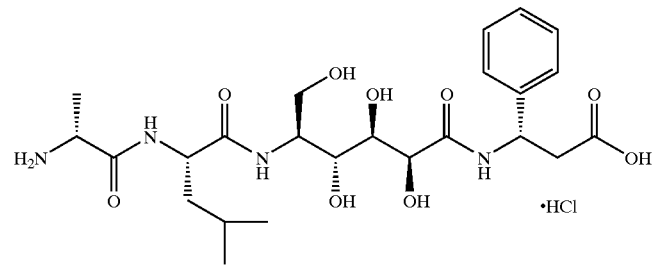
Compound of Example 71
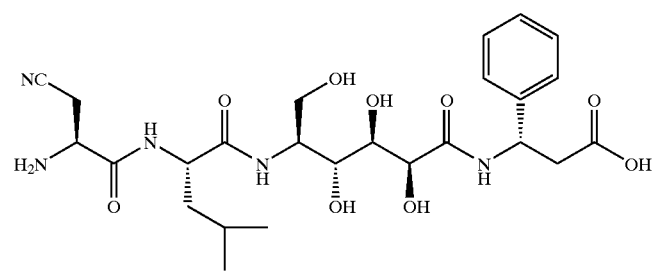
Compound of Example 72
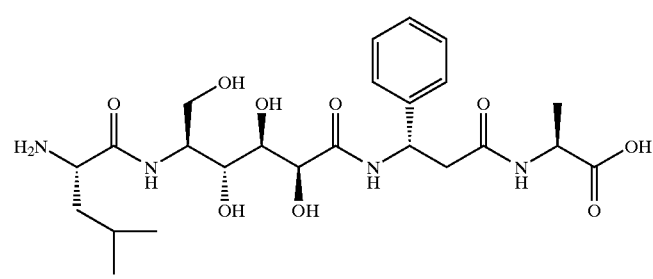
Compound of Example 73
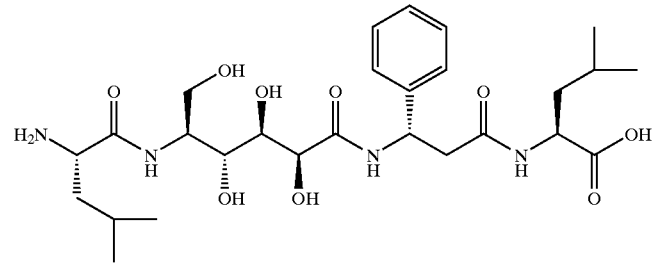
Compound of Example 74
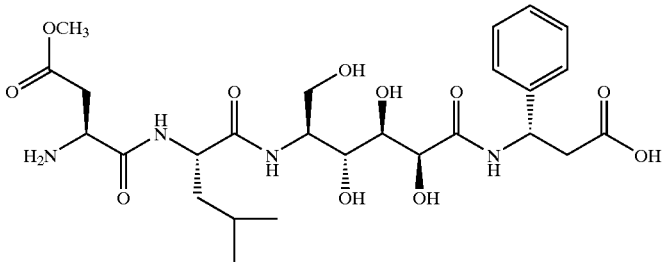

-continued
Compound of Example 75
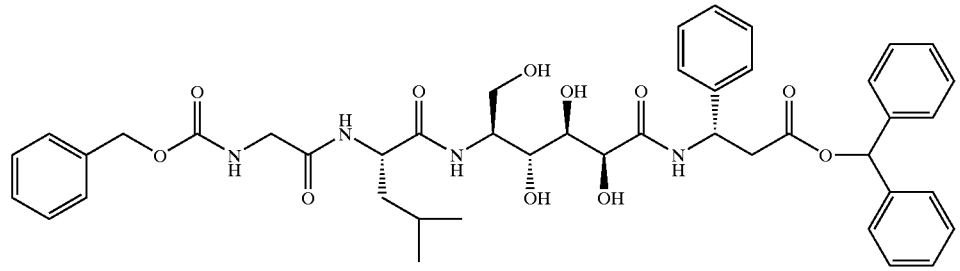
Compound of Example 76
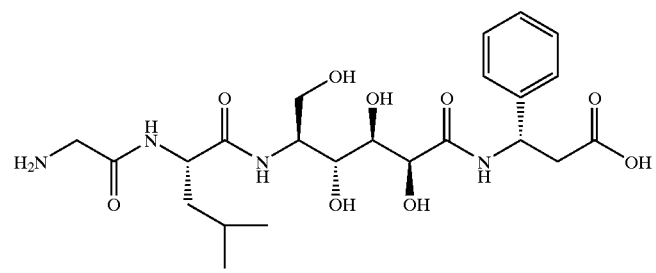
Compound of Example 77
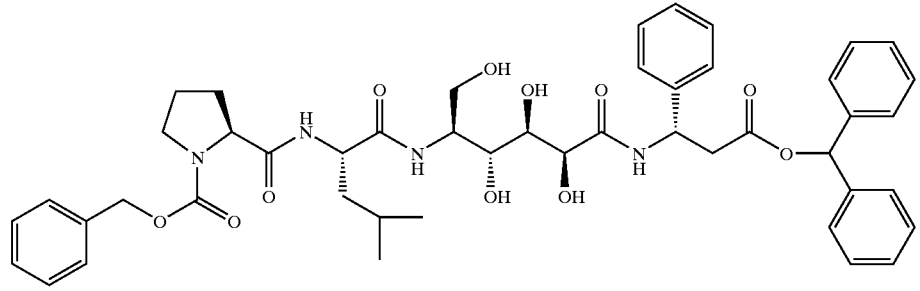
Compound of Example 78
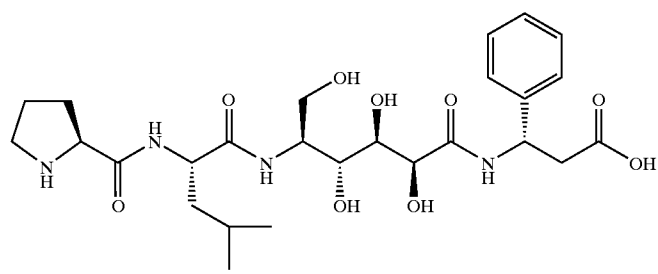
Compound of Example 79
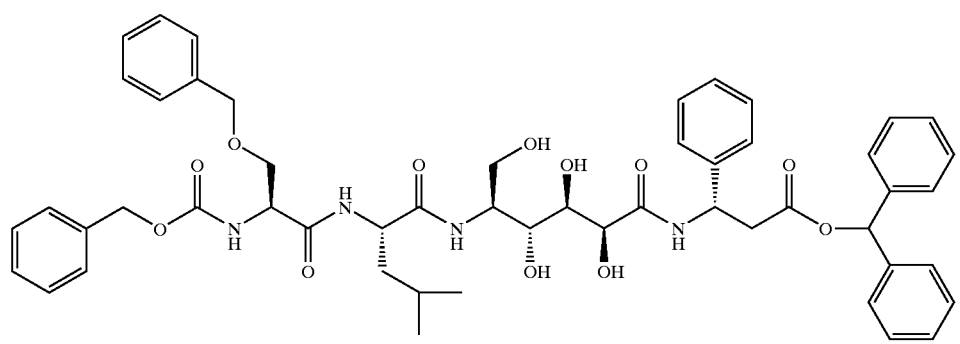

| | |
|---|---|
| Compound of Example 80 | 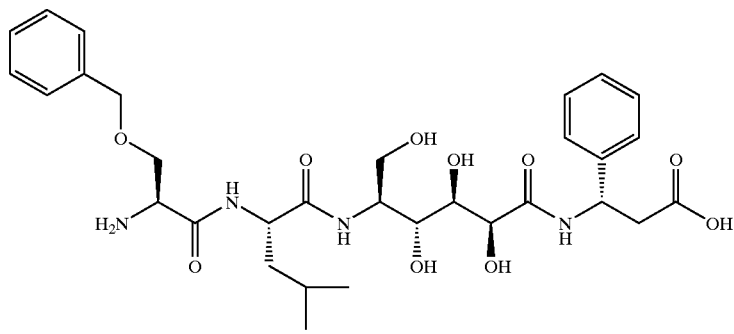 |
| Compound of Example 81 | 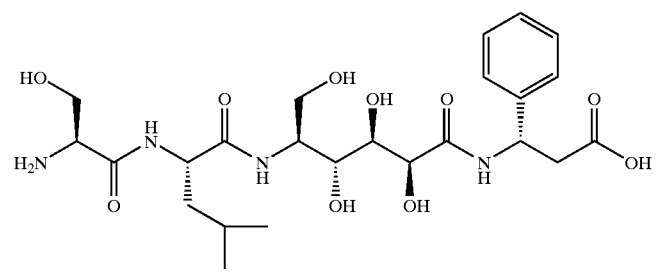 |
| Compound of Example 82 | 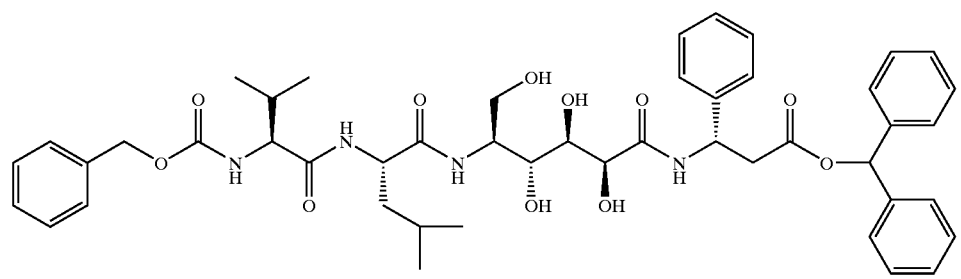 |
| Compound of Example 83 | 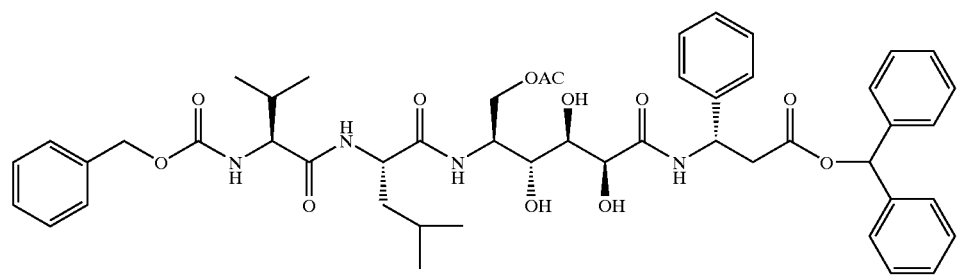 |
| Compound of Example 84 | 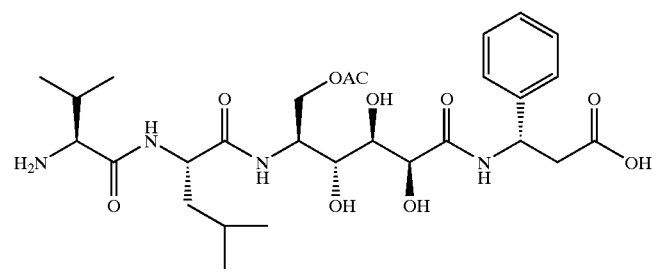 |

-continued
Compound of Example 85
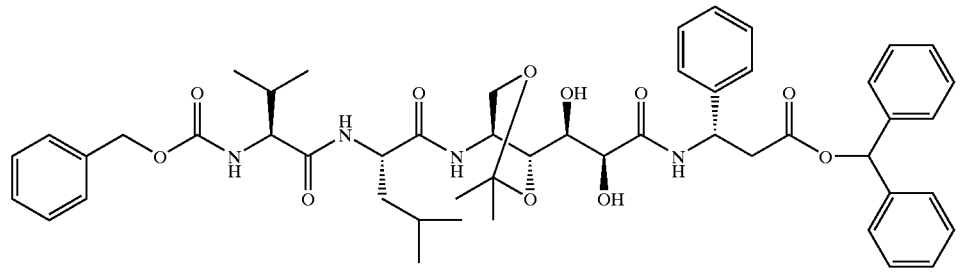
Compound of Example 86
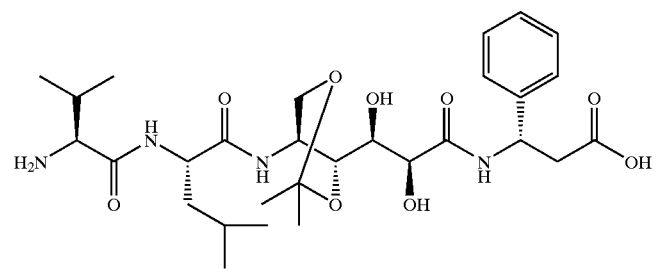
Compound of Example 87
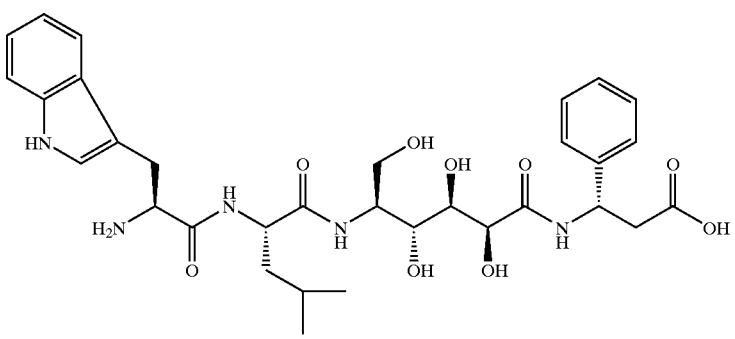
Compound of Example 88
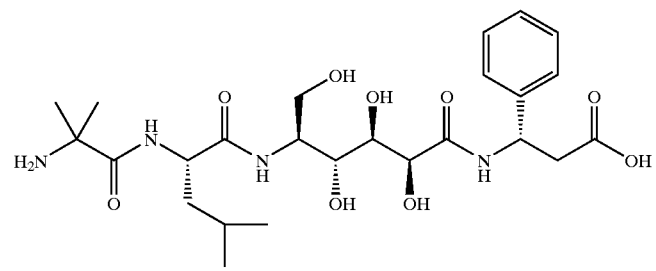
Compound of Example 89
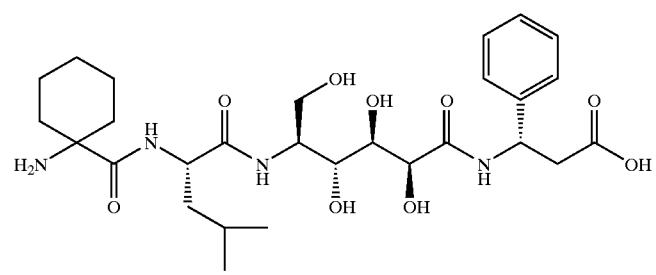

-continued
| | |
|---|---|
| Compound of Example 90 | 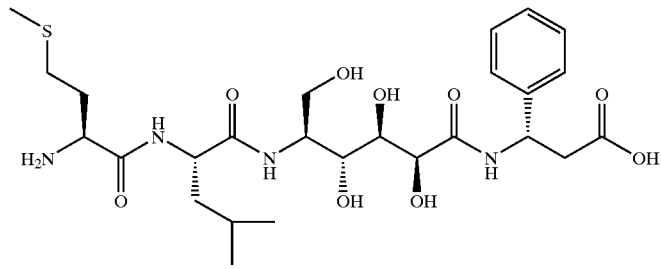 |
| Compound of Example 91 | 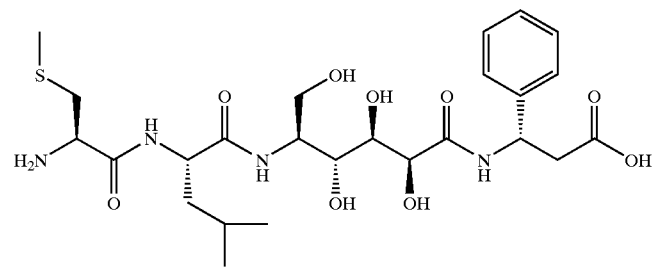 |
| Compound of Example 92 | 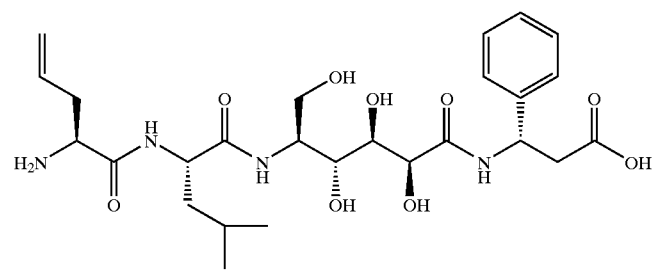 |
| Compound of Example 93 | 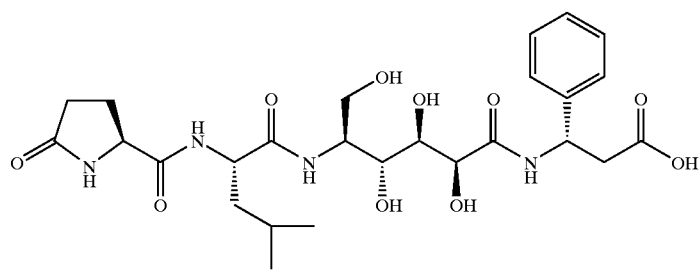 |
| Compound of Example 94 | 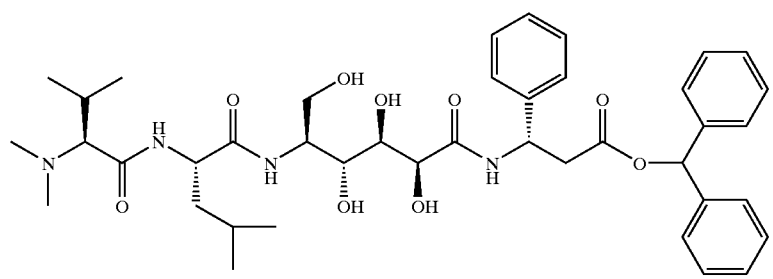 |

| | |
|---|---|
| Compound of Example 95 | 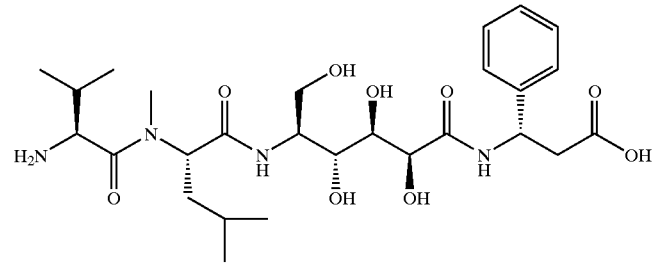 |
| Compound of Example 96 | 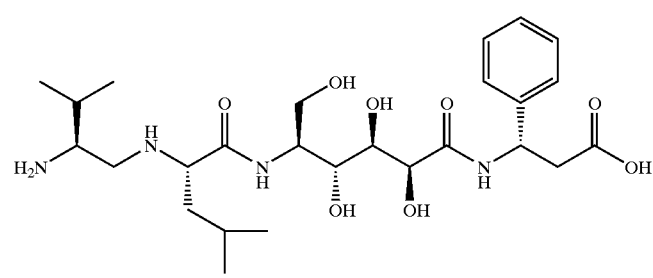 |
| Compound of Example 97 | 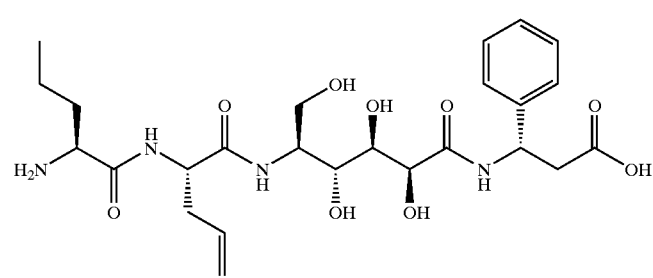 |
| Compound of Example 98 | 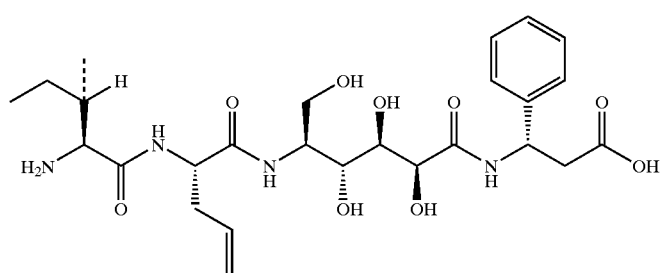 |
| Compound of Example 99 | 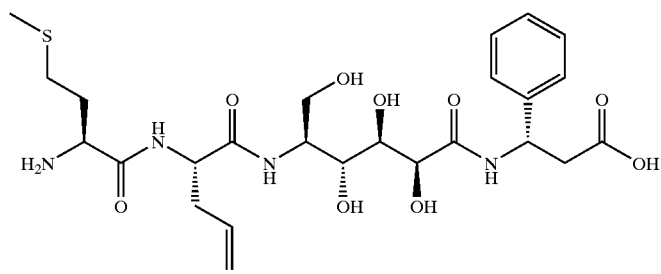 |

Compound of Example 100

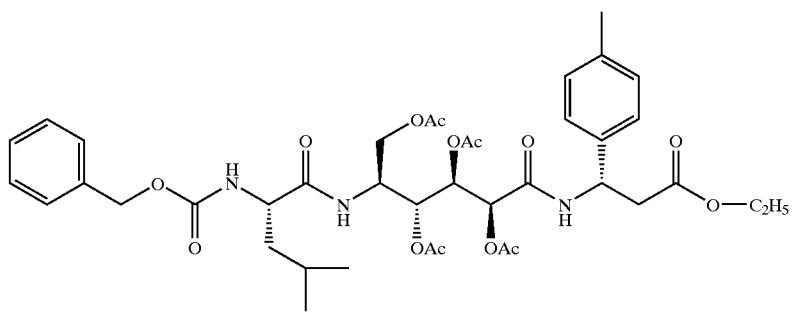

Compound of Example 101

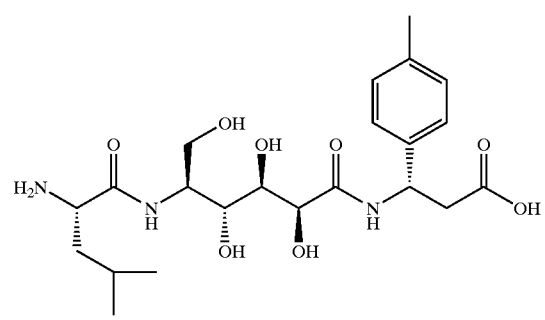

Test Example 1
In vitro Antibacterial Test: Antibacterial Activity Against *Helicobacter pylori* in vitro Using *Helicobacter pylori* (NCTC 11637) as the test strain, the antibacterial activity of HC-70I (Compound 1) and HC-70II (Compound 2) was assayed by the agar dilution method as follows. HC-70I and HC-70II were respectively dissolved in dimethyl sulfoxide, and using sterile distilled water, a doubling dilution series was prepared for use as samples. Using 7% horse blood-supplemented Brucella agar as the medium, plates were prepared by mixing 2 mL of each sample with 18 mL of the 7% horse blood-Brucella agar. To prepare an inoculum, *Helicobacter pylori* was shake-cultured in 2.5% fetal bovine serum-Brucella broth at 37° C. for 20 hours using a gas pak jar containing CampyPak™ [BBL Beckton Dickinson Microbiology Systems]. Assay plates were inoculated with 5 μL each of the respective cell suspensions adjusted to about $10^6$ CFU/mL with 2.5% fetal bovine serum-Brucella broth and were incubated at 37° C. for 4 days in the gas pak jar containing CampyPak™ and water-soaked sanitary cotton. After cultivation, the degree of bacterial growth was grossly evaluated and the minimal concentration at which no growth was observed was recorded as the MIC (minimal inhibitory concentration). The MIC value was 0.025 (μg/mL) for both HC-70I and HC-70II.

Test Example 2
In vivo Antibacterial Test

Mice (Crj: ICR, male, aged 5 weeks) were deprived of food for 20 hours and $6.17 \times 10^7$ CFU/mouse of *Helicobacter pylori* TN2F4 was inoculated into the stomach. Starting 11 days after infection, 50 mg/kg of the test compound suspended in 0.5% methyl cellulose/water was adminstered orally twice. daily, in the morning and evening, for 2 consecutive days. On the day following the last dose, the stomach was isolated from the infected mouse and homogenized and a 10-fold dilution series of the homogenate was inoculated on activated charcoal-modified Skirrow medium. Cultivation was carried out microaerobically at 37° C. for 4 days and the eradication rate was determined according to growth of the bacteria.

The results are presented in Table 1. The number of bacteria was expressed in mean±standard error and the statistical analysis was made in comparison with the control group by the Dunnett method.

TABLE 1

| Sample | Dose (mg/kg) | Clearance rate (%) | Bacteria retrieved (Log CFU/gastric wall) |
|---|---|---|---|
| Control (0.5% methylcellulose) | 0 | 0/4 (0) | 4.67 ± 0.06 |
| HC-70II.HCl | 50 | 4/4 (100) | ND |
| HC-70III | 50 | 4/4 (100) | ND |

ND: not detected

It can be seen from Table 1 that, at the dose level of 50 mg/kg, both HC-70II HCl (Compound 4) and HC-70III (Compound 3) accomplished 100% clearance. It is, therefore, clear that the medicinal composition of the invention is effective in the prevention and treatment of *Helicobacter pylori*-associated gastritis, gastric ulcer, duodenal ulcer, and cancer of the stomach.

Test Example 3

Five-week-old MON/Jms/Gbs mongolian gerbils were inoculated intragastrically with $10^{7.58}$ CFU of *Helicobacter pylori* TN2GF4. Four weeks after infection, a compound of the Example 47, suspended in 0.5% methyl cellulose, was administered orally at a dose of 30 mg/kg twice daily for 2 days. The animals were killed on the day after the final treatment. Stomachs were removed and homogenized with 3 ml of brucella broth, and the bacterial count in the homogenates was determined by serial dilution and titration on modified Skirrow's plates. The plates were incubated at 37° C. for 4 days in a microaerobic atmosphere prior to counting. No detectable *Helicobacter pylori* in the stomach on the day after final treatment was defined as clearance.

A compound of the Example 47 at a dose of 30 mg/kg twice daily for 2 days decreased the number of infecting organism; the clearance was attained in 2 out of 4 gerbils.
Table 2
Effect of repetitive administration of a compound of the Example 47 against gastric infection caused by *H. pylori* TN2GF4 in MON/JmsIGbs mongolian gerbils

| Compound | Dose (mg/kg) | Clearance rate Cleared/total(%) | Bacterial recovery Log CFU/gastric wall Mean ± SE |
|---|---|---|---|
| Vehicle control | 0 | 0/3 (0) | 6.05 ± 0.08 |
| compound of the Example 47 | 30 | 2/4 (50) | 2.23 ± 0.44** |

**p < 0.01 vs vehicle control by Dunnett's test.

Test Example 4

In vivo *Anti-Helicobacter pylori* Effect of the Gastric Mucosa Adhesive Preparation Mongolian gerbils (MON/Jms/Gbs) infected with H. pylori were orally dosed with the HC-70-II containing gastric mucosa adhesive preparation obtained in Formulation Example 3 (HC-70-II AdMMS-1 in Table 3), and a 0.5% methylcellulose suspension containing HC-70-II (HC-70-II suspension in Table 3), respectively at a dose of 3 mg/kg, 10 mg/kg as HC-70-II twice a day for 7 consecutive days. At 16 hours after the final dose, the stomach was excised and the gastric wall was homogenized and serial dilutions were plated on the *Helicobacter Pylori* selective medium. The inoculated medium was incubated for 4 days at 37° C. under microaerobic conditions and the number of viable cells was counted. The results are shown in Table 3.

TABLE 3

| Formulation | Dose (mg/kg) HC-70-II | Bacterial recovery Log CFU/gastric wall Mean ± SE |
|---|---|---|
| Control | 0 | 6.69 ± 0.19 |
| HC-70-II AdMMs-1 | 3 | 4.11 ± 1.08 |
| HC-70-II, suspension | 10 | 4.09 ± 0.80 |

Compared with the HC-70-II-suspension, the HC-70-II containing gastric mucosa adhesive preparation showed the same level of anti-Hebcobactor pylori activity as that of the HC-70-II suspension with one third of the dosage of the HC-70-II suspension.

Formulation Example 1

For use as a therapeutic agent for *Helicobacter pylori* infections, the compound or salt of the invention can be administered typically in the following dosage forms.

1. Capsules

| | |
|---|---|
| (1) HC-70I | 100 mg |
| (2) Lactose | 90 mg |
| (3) Microcrystalline cellulose | 70 mg |
| (4) Magnesium stearate | 10 mg |
| | 270 mg per capsule |

The whole amounts of (1), (2), and (3) and ½ of (4) are blended and granulated. To the granulation is added the remainder of (4) and the whole composition is filled into gelatin capsule shells.

2. Tablets

| | |
|---|---|
| (1) HC-70I | 100 mg |
| (2) Lactose | 35 mg |
| (3) Corn starch | 150 mg |
| (4) Microcrystalline cellulose | 30 mg |
| (5) Magnesium stearate | 5 mg |
| | 320 mg per tablet |

The whole amounts of (1), (2) and (3), ⅔ of (4), and ½ of (5) are blended and granulated. To the granulation are added the remainders of (4) and (5), and the whole composition is compressed.

Formulation Example 2

A mixture of hydrogenated caster oil (Lubri wax 101™, Freund Industrial Co. Ltd.) (40 g) and behenic acid hexa (tetra) glyceride (HB-310™, Sakamoto Yakuhin Kogyo Co. Ltd.)(39 g) was melted at 85° C. To this melt, 1 g of compound 2 (HC-70-II), 10 g of acrylic polymer (HIVISWAKO 104™, Wako Pure Chemical Industries, Ltd.) and 10 g of low substituted hydroxypropylcellulose (L-HPC™, Shin-Etsu Chemicals) were serially added and the mixture was stirred for dispersion at a constant temperature of 85° C. for 2 hours. This molten mixture was dropped onto a 15 cm (di.) aluminum disk rotating at 2700 rpm at a flow rate of 50 g/min, whereby spherical fine granules 42 mesh passing through were obtained.

Formulation Example 3

A mixture of hydrogenated caster oil (Lubri wax 101™, Freund Industrial Co. Ltd.) (20 g) and behenic acid hexa (tetra) glyceride (HB-310™, Sakamoto Yakuhin Kogyo Co. Ltd.)(59 g) was melted at 85° C. To this melt, 1 g of compound 2 (HC-70-II), 10 g of acrylic polymer (HIVISWAKO 104™, Wako Pure Chemical Industries, Ltd.) and 10 g of low substituted hydroxypropylcellulose (L-HPC™, Shin-Etsu Chemicals) were serially added and the mixture was stirred for dispersion at a constant temperature of 85° C. for 2 hours. This molten mixture was dropped onto a 15 cm (di.) aluminum disk rotating at 2700 rpm at a flow rate of 50 g/min, whereby spherical fine granules 42 mesh passing through were obtained.

Formulation Example 4

A mixture of behenic acid hexa (tetra) glyceride (HB-310™, Sakamoto Yakuhin Kogyo Co. Ltd.)(69 g) was melted at 80° C. To this melt, 1 g of compound 2 (HC-70-II), 10 g of acrylic polymer (HIVISWAKO 104™, Wako Pure Chemical Industries, Ltd.) and 20 g of low substituted hydroxypropylcellulose (L-HPC™, Shin-Etsu Chemicals) were serially added and the mixture was stirred for dispersion at a constant temperature of 80° C. for 2 hours. This molten mixture was dropped onto a 15 cm (di.) aluminum disk rotating at 2400 rpm at a flow rate of 50 g/min, whereby spherical fine granules 42 mesh passing through were obtained.

Formulation Example 5

A mixture of hydrogenated caster oil (Lubri wax 101™, Freund Industrial Co. Ltd.) (30 g) and behenic acid hexa (tetra) glyceride (HB-310™, Sakamoto Yakuhin Kogyo Co. Ltd.)(49 g) was melted at 85° C. To this melt, 1 g of compound 2 (HC-70-II), 10 g of acrylic polymer (HIVISWAKO 104™, Wako Pure Chemical Industries, Ltd.) and 10 g of low substituted hydroxypropylcellulose (L-HPC™, Shin-Etsu Chemicals) were serially added and the mixture was stirred for dispersion at a constant temperature of 85° C. for2 hours. This molten mixture was dropped onto a 15 cm (di.) aluminum disk rotating at 2700 rpm at a flow rate of 50 g/min, whereby spherical fine granules 42 mesh passing through were obtained.

Formulation Example 6

A mixture of hydrogenated caster oil (Lubri wax 101™, Freund Industrial Co. Ltd.) (20 g) and behenic acid hexa (tetra) glyceride (HB-310™, Sakamoto Yakuhin Kogyo Co. Ltd.)(59 g) was melted at 85° C. To this melt, 1 g of compound 2 (HC-70-II), 10.0 g of acrylic polymer (FX-214™, BF Goodrich Industries, Ltd.) and 10 g of low substituted hydroxypropylcellulose (L-HPC™, Shin-Etsu Chemicals), were serially added and the mixture was stirred for dispersion at a constant temperature of 85° C. for 2 hours. This molten mixture was dropped onto a 15 cm (di.) aluminum disk rotating at 2700 rpm at a flow rate of 50 g/min, whereby spherical fine granules 42 mesh passing through were obtained.

Formulation Example 7

A mixture of behenic acid hexa (tetra) glyceride (HB-310™, Sakamoto Yakuhin Kogyo Co. Ltd.)(60 g) was melted at 80° C. To this melt, 30 g of compound 2 (HC-70-II), 6 g of acrylic polymer (HIVISWAKO 104™, Wako Pure Chemical Industries, Ltd.) and 4 g of low substituted hydroxypropylcellulose (L-HPC™, Shin-Etsu Chemicals) were serially added and the mixture was stirred for dispersion at a constant temperature of 80° C. for 2 hours. This molten mixture was dropped onto a 15 cm (di.) aluminum disk rotating at 3960 rpm at a flow rate of 50 g/min, whereby spherical fine granules 42 mesh passing through were obtained.

Formulation-Example 8

A mixture of hydrogenated caster oil (Lubri wax 101™, Freund Industrial Co. Ltd.) (10 g) and behenic acid hexa (tetra) glyceride (HB-310™, Sakamoto Yakuhin Kogyo Co. Ltd.)(50 g) was melted at 85° C. To this melt, 30 g of compound 2 (HC-70-II), 6 g of acrylic polymer (HIVISWAKO 104™, Wako Pure Chemical Industries, Ltd.) and 4 g of low substituted hydroxypropylcellulose (L-HPC™, Shin-Etsu Chemicals) were serially added and the mixture was stirred for dispersion at a constant temperature of 85° C. for 2 hours. This molten mixture was dropped onto a 15 cm (di.) aluminum disk rotating at 3960 rpm at a flow rate of 50 g/min, whereby spherical fine granules 42 mesh passing through were obtained.

Formulation Example 9

A mixture of behenic acid hexa (tetra) glyceride (HB-310™, Sakamoto Yakuhin Kogyo Co. Ltd.)(60 g) was melted at 80° C. To this melt, 30 g of compound 2 (HC-70-II), 6 g of acrylic polymer (EX-214™, BF Goodrich Industries, Ltd.) and 4 g of low substituted hydroxypropylcellulose (L-HPC™, Shin-Etsu Chemicals) were serially added and the mixture was stirred for dispersion at a constant temperature of 80° C. for 2 hours. This molten mixture was dropped onto a 15 cm (di.) aluminum disk rotating at 3960 rpm at a flow rate of 50 g/min, whereby spherical fine granules 42 mesh passing through were obtained.

Formulation Example 10

A mixture of hydrogenated caster oil (Lubri wax 101™, Freund Industrial Co. Ltd.) (10 g) and behenic acid hexa (tetra) glyceride (HB-310™, Sakamoto Yakuhin Kogyo Co. Ltd.)(50 g) was melted at 85° C. To this melt, 30 g of compound 2 (HC-70-II), 6 g of acrylic polymer (EX-214™, BF Goodrich Industries, Ltd.) and 4 g of low substituted hydroxypropylcellulose (L-HPC™, Shin-Etsu Chemicals) were serially added and the mixture was stirred for dispersion at a constant temperature of 85° C. for 2 hours. This molten mixture was dropped onto a 15 cm (di.) aluminum disk rotating at 3960 rpm at a flow rate of 50 g/min, whereby spherical fine granules 42/119 mesh passing through were obtained.

INDUSTRIAL APPLICABILITY

Compound (I) of the invention has specific and high antibacterial activity against Helicobacter bacteria represented by *Helicobacter pylori*. Therefore, with this Compound (I), the desired anti-*Helicobacter Pylori* efficacy can be achieved at a remarkably reduced dose as compared with the conventional antibacterial agents available for control of Helicobacter bacteria (especially *Helicobacter pylori*).

Compound (I) is effective in the prevention or treatment of various diseases associated with Helicobacter bacteria, such as duodenal ulcer, gastric ulcer, chronic gastritis, and cancer of the stomach. Moreover, because *Helicobacter pylori* is a major factor in recurrences of ulcer, Compound (I) is effective in preventing recurrence of ulcers as well.

Furthermore, Compound (I) shows no activity against such gram-positive bacteria as those of the general Staphylococcus and Bacillus, or such gram-negative bacteria as those belonging to the genera Escherichia, Pseudomonas, Proteus, Klebsiella, Serratia, Salmonella, Citrobacter, Alcaligenes, etc. Therefore, Compound (I) is selectively effective in the prevention or treatment of diseases associated with Helicobacter bacteria, with minimal effects on other bacteria and fungi, and, therefore, can be used as a safe drug.

The gastric mucosa adhesive composition of the present invention can reduce the amount of the active ingredient at the dosage of half to one twentieth of the dosage of its suspension.

What is claimed is:

1. A compound of the formula (I):

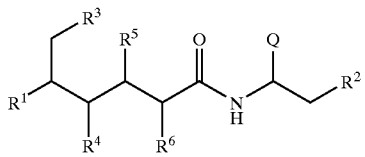

wherein $R^1$ represents amino which may be substituted;
$R^2$ represents carboxy which may be esterified or amidated;
$R^3$, $R^4$, $R^5$, and $R^6$ each represents hydroxy which may be protected;
Q represents aryl which may be substituted, wherein said compound exhibits anti-*Helicobacter pylori* activity;
or a salt thereof.

2. The compound according to claim 1, wherein $R^1$ is an acylamino group or an amino group substituted by a hydrocarbon group which may also be substituted.

3. The compound according to claim 2, wherein the acylamino group is an amino group substituted by an amino acid group.

4. The compound according to claim 3, wherein the amino acid group is an α-amino acid group.

5. The compound according to claim 1, wherein $R^1$ is an amino group or a group represented by the formula:

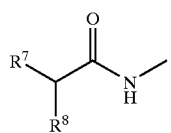

wherein $R^7$ is an amino group which is optionally substituted with an α-L-amino acid group, wherein said α-amino acyl group is optionally substituted with a second α-L-amino acid group,
$R^8$ is a hydrocarbon group which may be substituted;
$R^2$ represents a carboxy group;
$R^3$, $R^4$, $R^5$, and $R^6$ each represents a hydroxy group;
Q represents a phenyl group.

6. The compound according to claim 5, which is represented by the formula (V):

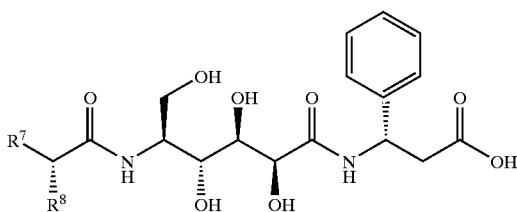

wherein $R^7$ is an amino group which may be substituted with an α-L-amino acid residue which may be substituted with an α-L-amino acid residue and $R^8$ is a hydrocarbon group which may be substituted.

7. The compound according to claim 5, wherein $R^8$ is a $C_{1-10}$ alkyl group, a $C_{6-14}$ aryl-$C_{1-6}$ alkyl group, a $C_{2-10}$ alkenyl group or a $C_{2-10}$ alkynyl group, each of which may be substituted.

8. The compound according to claim 7, wherein $R^8$ is a $C_{1-6}$ alkyl group or a $C_{2-6}$ alkenyl group.

9. The compound according to claim 7, wherein $R^7$ is an amino group which may be substituted with valyl group, a valyl-valyl group, a valyl-isoleucyl group or a valyl-leucyl group.

10. The compound according to claim 8, wherein $R^8$ is an isobutyl group or an allyl group.

11. The compound according to claim 1, wherein $R^1$ is an amino group.

12. (S)-3-[(2S,3R,4R,5S)-2,3,4,6-tetrahydroxy-5-(L-valyl-L-valyl-L-leucyl)aminohexanoyl]amino-3-phenylpropionic acid.

13. (S)-3-[(2S,3R,4R,5S)-2,3,4,6-tetrahydroxy-5-(L-valyl-L-isoleucyl-L-leucyl)aminohexanoyl]amino-3-phenylpropionic acid.

14. (S)-3-[(2S,3R,4R,5S)-2,3,4,6-tetrahydroxy-5-(L-valyl-L-leucyl-L-leucyl)aminohexanoyl]amino-3-phenylpropionic acid.

15. (S)-3-[(2S,3R,4R,5S)-2,3,4,6-tetrahydroxy-5-(L-valyl-L-leucyl)aminohexanoyl]amino-3-phenylpropionic acid.

16. (S)-3-[(2S,3R,4R,5S)-2,3,4,6-tetrahydroxy-5-(L-leucyl)aminohexanoyl]amino-3-phenylpropionic acid.

17. (S)-3-[(2S,3R,4R,5S)-5-((S)-2-amino-4-pentenoyl)amino-2,3,4,6-tetrahydroxyhexanoyl]amino-3-phenylpropionic acid.

18. (S)-3-[(2S,3R,4R,5S)-5-((S)-2-aminobutyryl)amino-2,3,4,6-tetrahydroxyhexanoyl]amino-3-phenylpropionic acid.

19. (S)-3-[(2S,3R,4R,5S)-2,3,4,6-tetrahydroxy-5-(L-isoleucyl-L-leucyl)aminohexanoyl]amino-3-phenylpropionic acid.

20. (S)-3-[(2S,3R,4R,5S)-2,3,4,6-tetrahydroxy-5-(L-methionyl-L-leucyl)aminohexanoyl]amino-3-phenylpropionic acid.

21. (S)-3-[(2S,3R,4R,5S)-2,3,4,6-tetrahydroxy-5-((S)-2-(L-norvalyl)amino-4-pentenoyl]amino-3-phenylpropionic acid.

22. A composition comprising the compound according to claim 1 and a carrier, diluent or excipient.

23. A composition according to claim 22, for inhibiting the growth of *Helicobacter pylori*, which comprises an effective *Helicobacter pylori* growth inhibiting amount of said compound.

24. A composition according to claim 23, where said *Helicobacter pylori* is found in the gastrointestinal tract of a mammal.

25. An anti-*Helicobacter pylori* agent comprising the compound according to claim 1 which is a first antibacterial agent, together with an agent selected from the group consisting of a second antibacterial agent, an antiulcerative agent, and a combination of a said second antibacterial agent and said antiulcerative agent.

26. The composition according to claim 22, which is a gastric mucosa adhesive composition.

27. The composition according to claim 26, which comprises (a) the compound according to claim 1, (b) a lipid and/or a polyglycerol fatty acid ester and (c) a viscogenic agent.

28. The composition according to claim 27, wherein (c) the viscogenic agent is an acrylic polymer or a salt thereof.

29. An anti-*Helicobacter pylori* composition which comprises (a) the compound according to claim 1, (b) a lipid and/or a polyglycerol fatty acid ester (c) a viscogenic agent and (d) a material which swells the viscogenic agent.

30. The composition according to claim 29, wherein the material which swells the viscogenic agent is a curdlan and/or a low-substituted hydroxypropylcellulose.

31. A method of producing the compound of formula (I):

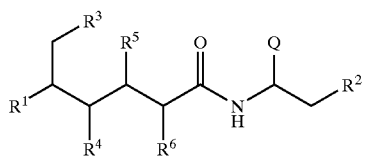

wherein $R^1$ represents amino which may be substituted;
$R^2$ represents carboxy which may be esterified or amidated;
$R^3$, $R^4$, $R^5$, $R^6$ each represents hydroxyl which may be protected;
Q represents aryl which may be substituted,
said method comprising
(a) reacting a carboxylic acid of formula (II):

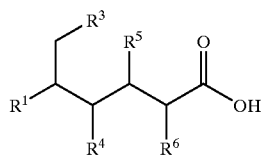

or a salt thereof, or a reactive derivative of a carboxylic acid of formula II with a compound of the formula (III):

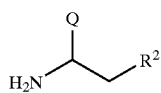

for a time and under conditions effective to produce a compound according to claim 1; and
(b) isolating the compound according to claim 1;
wherein $R^1$ represents an amino group which may be substituted, and
$R^3$, $R^4$, $R^5$ and $R^6$ each represent a hydroxy group which may be protected;
$R^2$ represents a carboxy group which may be esterified or amidated; and
Q represents an aryl group which may be substituted.
32. A method of producing the compound according to claim 1 comprising
(a) reacting a compound of the formula (IV):

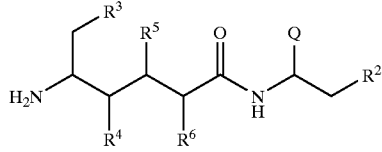

or a salt thereof, or a reactive derivative of a compound of formula (II) with a compound of the formula: $R^9$-X for a time and under conditions effective to produce a compound according to claim 1; and
(b) isolating the compound according to claim 1;
wherein $R^2$ represents a carboxyl group which may be esterified or amidated;

$R^3$, $R^4$, $R^5$ and $R^6$ each represent a hydroxy group which may be protected,
Q represents an aryl group which may be substituted;
$R^9$ represents an acyl group, or hydrocarbon group which may be substituted; and
X represents a leaving group.
33. A method of producing a compound according to claim 5 comprising
a) fermenting in a culture medium, a strain of Bacillus for a time and under conditions effective to produce a compound according to claim 5, and then
b) harvesting the compound according to claim 5.
34. The method according to claim 33, wherein the strain of microorganism is Bacillus HC-70 or *Bacillus insolitus* HC-72.
35. A culture of Bacillus HC-70 or *Bacillus insolitus* HC-72 which produces the compound according to claim 5.
36. A method for inhibiting growth of *Helicobacter pylori* in a mammal comprising administering to a mammal in need thereof a compound of the formula (I):

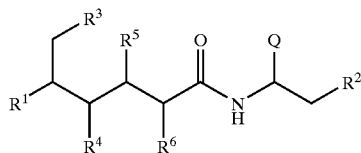

wherein $R^1$ represents amino which may be substituted;
$R^2$ represents carboxy which may be esterified or amidated;
$R^3$, $R^4$, $R^5$, and $R^6$ each represents hydroxy which may be protected;
Q represents aryl which may be substituted,
or salt thereof for a time and under conditions effective to inhibit growth of *Helicobacter pylori*.
37. A method for making a composition for inhibiting the growth of *Helicobacter pylori*, said method comprising combining a compound of the formula (I):

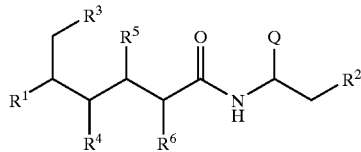

wherein $R^1$ represents amino which may be substituted;
$R^2$ represents carboxy which may be esterified or amidated;
$R^3$, $R^4$, $R^5$, and $R^6$ each represents hydroxy which may be protected;
Q represents aryl which may be substituted,
or a salt thereof with a carrier, diluent or excipient.
38. A method for inhibiting growth of *Helicobacter pylori* in a mammal afflicted with a gastric ulcer, comprising administering to a mammal in need thereof, a compound of claim 1 for a time and under conditions effective to inhibit growth of *Helicobacter pylori*.

* * * * *